US011813280B2

(12) United States Patent
Ganesh

(10) Patent No.: US 11,813,280 B2
(45) Date of Patent: Nov. 14, 2023

(54) REDUCING BETA-CATENIN AND IDO EXPRESSION TO POTENTIATE IMMUNOTHERAPY

(71) Applicant: Dicerna Pharmaceuticals, Inc., Lexington, MA (US)

(72) Inventor: Shanthi Ganesh, Shrewsbury, MA (US)

(73) Assignee: DICERNA PHARMACEUTICALS, INC., Lexington, MA (US)

(*) Notice: Subject to any disclaimer, the term of this patent is extended or adjusted under 35 U.S.C. 154(b) by 241 days.

(21) Appl. No.: 16/958,969

(22) PCT Filed: Jan. 3, 2019

(86) PCT No.: PCT/US2019/012193
§ 371 (c)(1),
(2) Date: Jun. 29, 2020

(87) PCT Pub. No.: WO2019/136157
PCT Pub. Date: Jul. 11, 2019

(65) Prior Publication Data
US 2020/0338110 A1 Oct. 29, 2020

Related U.S. Application Data

(60) Provisional application No. 62/614,206, filed on Jan. 5, 2018.

(51) Int. Cl.
| | | |
|---|---|---|
| *C07H 21/04* | (2006.01) | |
| *A61K 31/713* | (2006.01) | |
| *A61P 35/04* | (2006.01) | |
| *A61K 31/4245* | (2006.01) | |
| *C07K 16/28* | (2006.01) | |
| *C12N 9/02* | (2006.01) | |
| *C12N 15/113* | (2010.01) | |
| *C07K 14/47* | (2006.01) | |

(52) U.S. Cl.
CPC ........ *A61K 31/713* (2013.01); *A61K 31/4245* (2013.01); *A61P 35/04* (2018.01); *C07K 16/2818* (2013.01); *C07K 16/2827* (2013.01); *C12N 9/0069* (2013.01); *C12N 15/113* (2013.01); *C07K 14/47* (2013.01); *C12N 2310/14* (2013.01); *C12N 2320/31* (2013.01); *C12Y 113/11052* (2013.01)

(58) Field of Classification Search
None
See application file for complete search history.

(56) References Cited

U.S. PATENT DOCUMENTS

| | | | | |
|---|---|---|---|---|
| 8,815,825 B2 * | 8/2014 | Brown | ................. | C12N 15/113 514/44 A |
| 2016/0331844 A1 | 11/2016 | Fotin-Mleczek et al. | | |
| 2018/0038868 A1 * | 2/2018 | Gajewski | ............... | A61K 35/15 |

FOREIGN PATENT DOCUMENTS

| | | |
|---|---|---|
| WO | 2012/006243 A2 | 1/2012 |
| WO | 2016/141312 A1 | 9/2016 |
| WO | 2017160983 A1 | 9/2017 |

OTHER PUBLICATIONS

Yue, Eddy W., et al. "INCB24360 (Epacadostat), a highly potent and selective indoleamine-2, 3-dioxygenase 1 (IDO1) inhibitor for immuno-oncology." ACS medicinal chemistry letters 8.5 (2017): 486-491.*

International Search Report and Written Opinion dated Apr. 1, 2019 for International Application No. PCT/US2019/012193 (Authorized officer, Blaine R. Copenheaver), 12 pages.

Prendergast et al., "Indoleamine 2,3-Dioxygenase and Its Therapeutic Inhibition in Cancer", International Review of Cell and Molecular Biology, Sep. 2017, vol. 336, pp. 175-203.

Jochems et al., "The IDO1 selective inhibitor epacadostat enhances dendritic cell immunogenicity and lytic ability of tumor antigen-specific T cells", Oncotarget, Jun. 2016, vol. 7, No. 24, pp. 37762-37772.

Spranger et al., "Mechanism of tumor rejection with doublets of CTLA-4, PD-1/PD-L1, or IDO blockade involves restored IL-2 production and proliferation of CD8+ T cells directly within the tumor microenvironment", Journal for ImmunoTherapy of Cancer, Feb. 2014, vol. 2, No. 3, 14 pages.

Moon et al., "Targeting the indoleamine 2,3-dioxygenase pathway in cancer", Journal for ImmunoTherapy of Cancer, 2015, vol. 3, No. 51, 10 pages.

Thaker et al., "IDO1 Metabolites Activate β-catenin Signaling to Promote Cancer Cell Proliferation and Colon Tumorigenesis in Mice", Gastroenterology, 2013, vol. 145, No. 2, 18 pages.

Hennequart et al., "Constitutive IDO1 Expression in Human Tumors Is Driven by Cyclooxygenase-2 and Mediates Intrinsic Immune Resistance", Cancer Immunology Research, 2017, vol. 4, No. 8, pp. 695-709.

Holmgaard et al., "Tumor-Expressed IDO Recruits and Activates MDSCs in a Treg-Dependent Manner", Cell Reports, 2015, vol. 13, pp. 412-424.

(Continued)

Primary Examiner — Kimberly Chong
(74) Attorney, Agent, or Firm — MH2 TECHNOLOGY LAW GROUP, LLP

(57) ABSTRACT

Provided herein are methods and compositions for treating cancer, including cancer that is not responsive to immunotherapy. In one aspect, the methods of treatment comprise administering to the subject a therapeutically effective amount of a β-catenin inhibitor, a therapeutically effective amount of an IDO inhibitor, and a therapeutically effective amount of an immunotherapeutic agent. Another aspect is directed to pharmaceutical compositions comprising a β-catenin inhibitor for use in treating cancer, wherein the composition is administered in combination with an IDO inhibitor and an immunotherapeutic agent. Yet another aspect is directed to a method of potentiating the therapeutic effect of immunotherapy against a cancer using a β-catenin inhibitor, such as a β-catenin nucleic acid inhibitor molecule, in combination with an IDO inhibitor.

40 Claims, 23 Drawing Sheets

Specification includes a Sequence Listing.

(56) References Cited

OTHER PUBLICATIONS

Gajewski et al., "Innate and adaptive immune cells in the tumor microenvironment", Nat Immunol., 2013, vol. 14, No. 10, pp. 1014-1022.
Sprenger et al., "Melanoma-intrinsic b-catenin signalling prevents anti-tumour immunity", Nature, 2015, vol. 523, 18 pages.
Ganesh et al., "Direct Pharmacological Inhibition of β-Catenin by RNA Interference in Tumors of Diverse Origin", Molecular Cancer Therapeutics, 2016, vol. 15, No. 9, pp. 2143-2154.
Ganesh et al., "Effect of RNAI-based β-catennin inhibition on immunosuppressive Wnt-activated tumors in combination with IDOi/PD-1 immunotherapy", Journal of Clinical Oncology, 2018, vol. 36, No. 15, Abstract, 2 pages.
Office Action dated Jan. 25, 2023 for corresponding Japanese Application No. 2020-536970, 9 pages including English translation.
Extended European Search Report dated Jul. 13, 2021 for corresponding European Patent Application No. 19735939.1, 9 pages.
Office Action and Search Report dated Aug. 8, 2023 for corresponding Chinese Application No. 201980007306.0, 24 pages, including English translation.
Zhang Maoyu, Industrial Patent Analysis Report No. 52, Tumor Immunotherapy, Jun. 30, 2017, pp. 56-57 (See p. 9 (paragraph 1) of the translation of Chinese Office Action dated Aug. 8, 2023 for a concise explanation of the relevance of this document).

\* cited by examiner

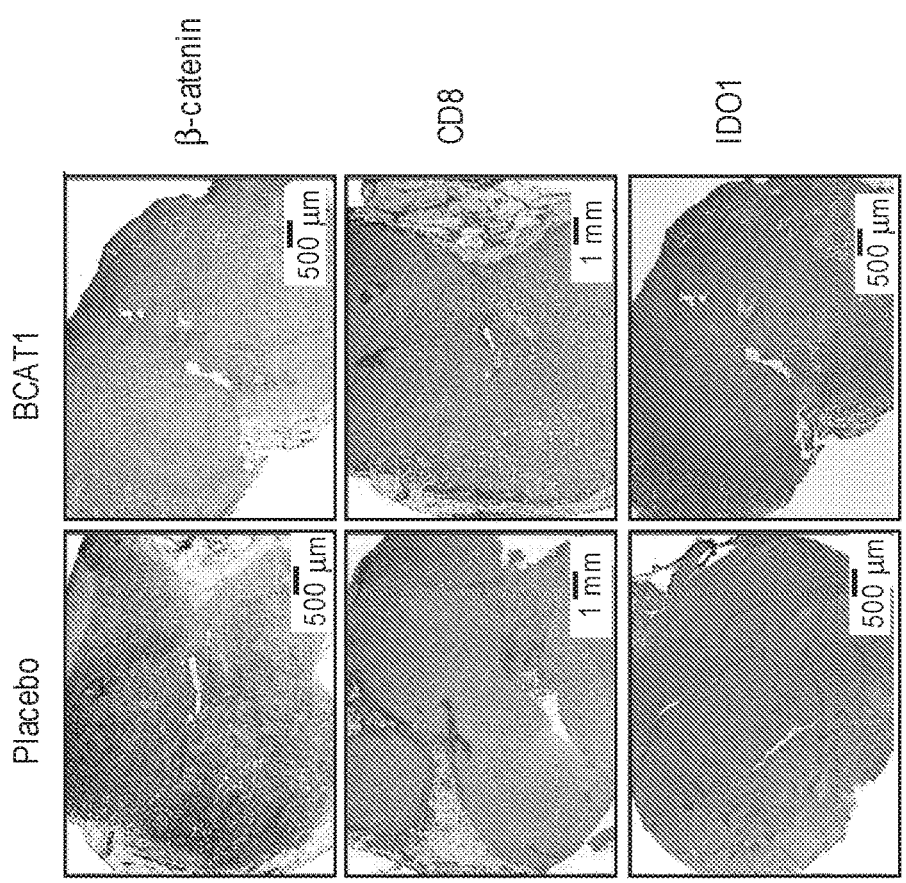
FIG. 1B
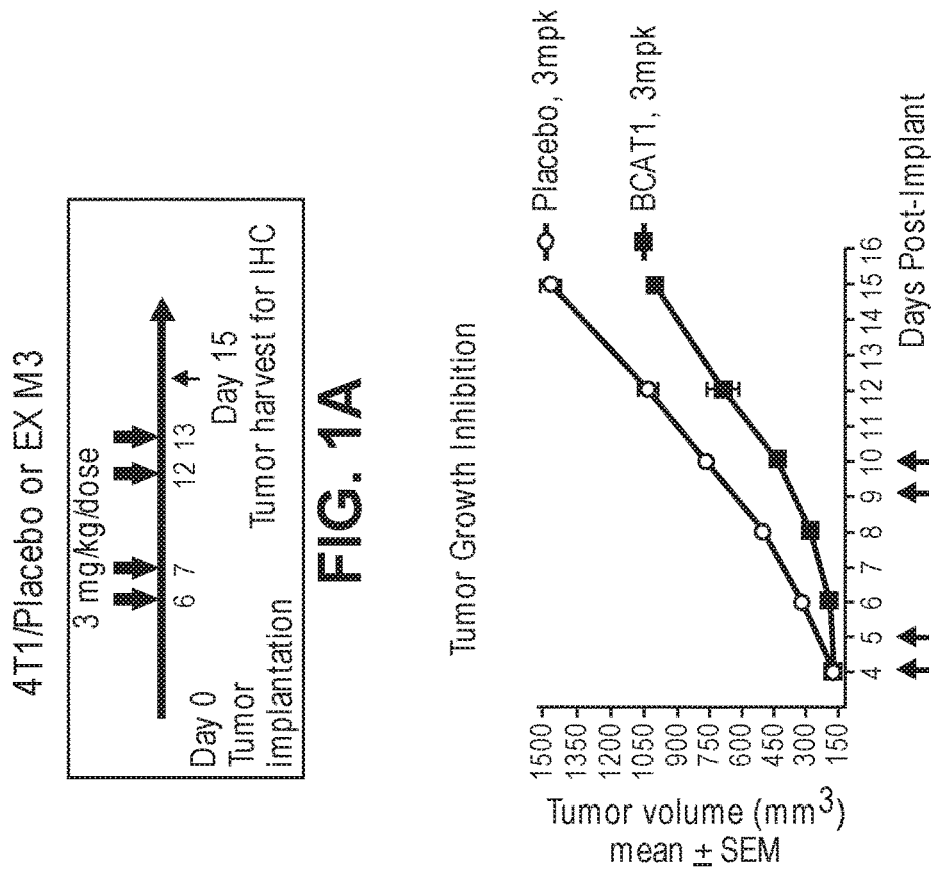
FIG. 1A
FIG. 1C

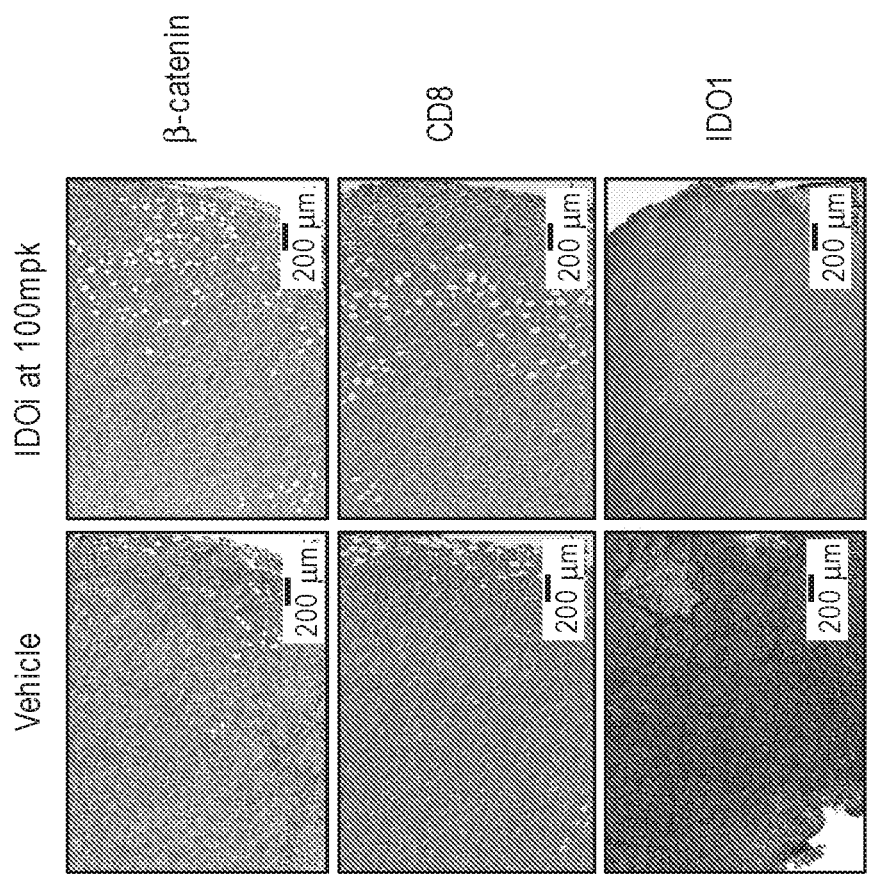
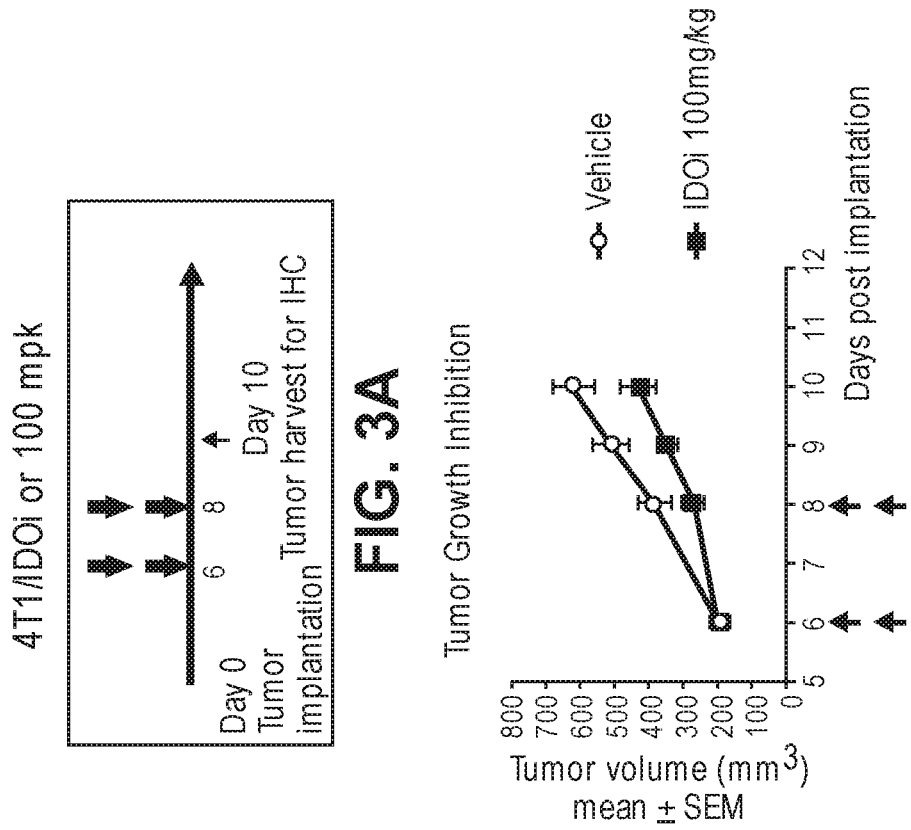
FIG. 3A
FIG. 3B
FIG. 3C

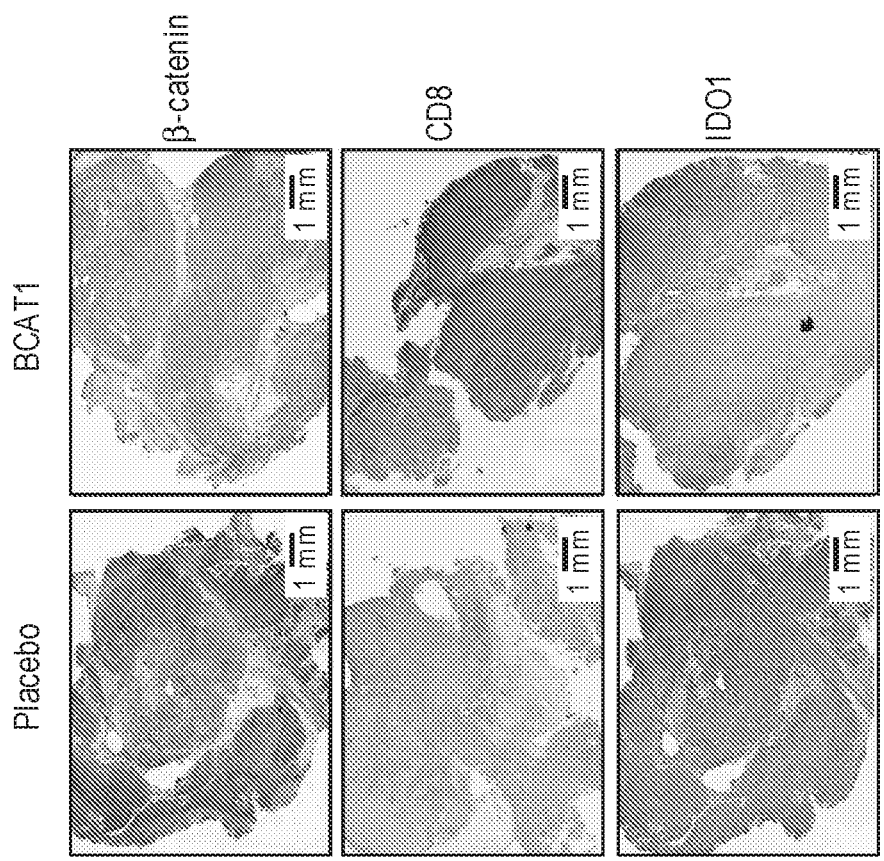
FIG. 6B
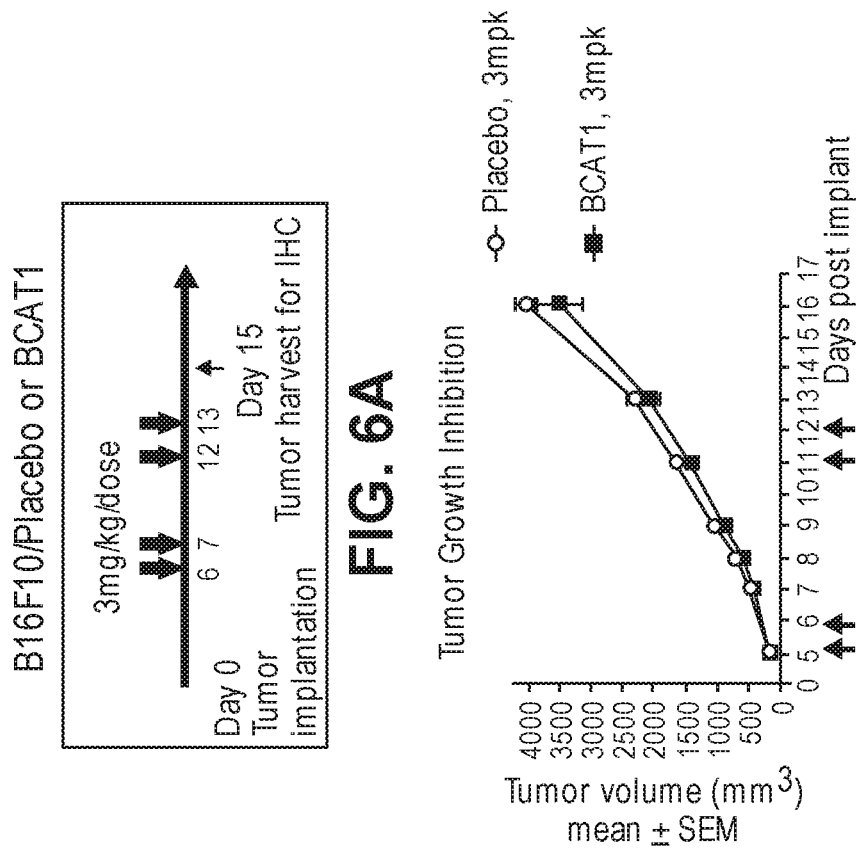
FIG. 6A
FIG. 6C

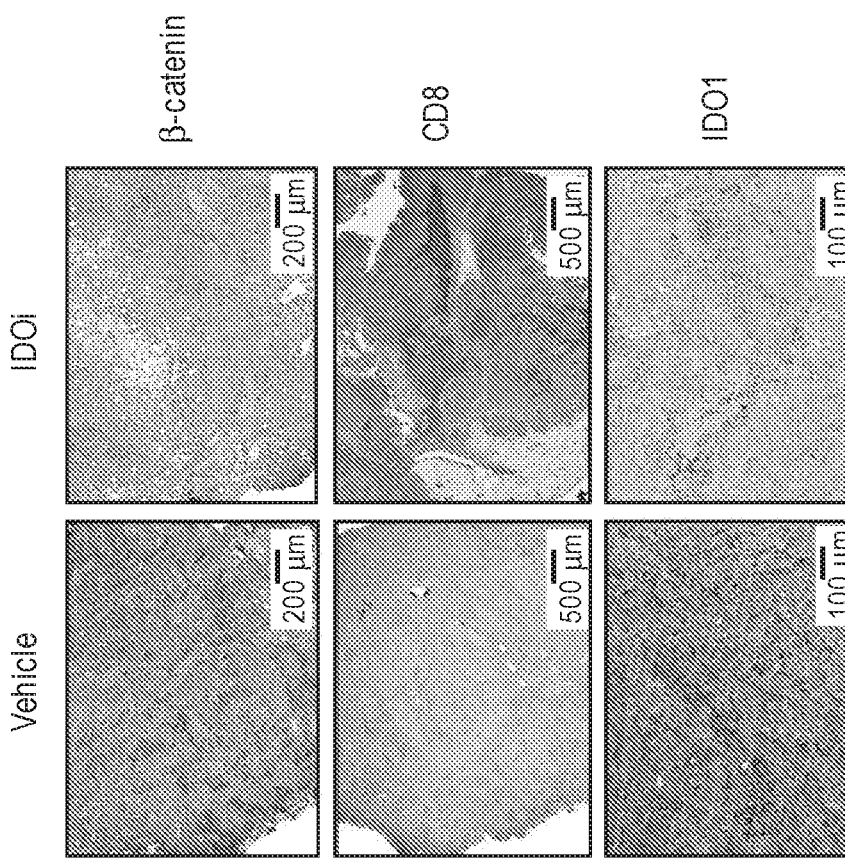
FIG. 8B
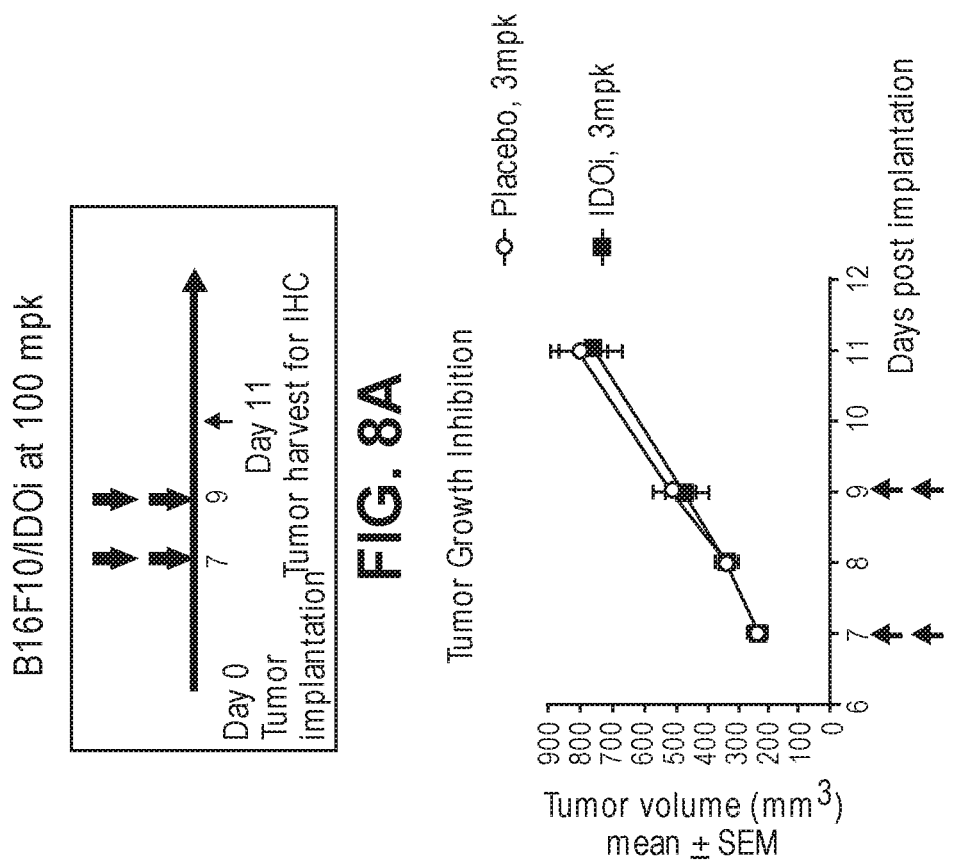
FIG. 8A
FIG. 8C

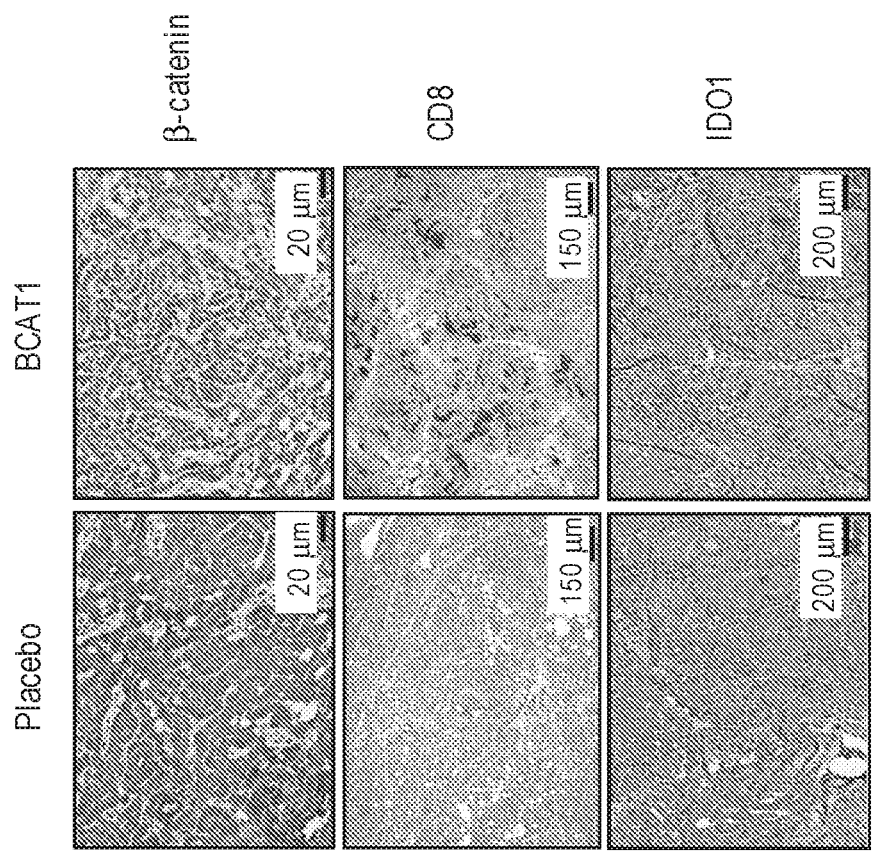
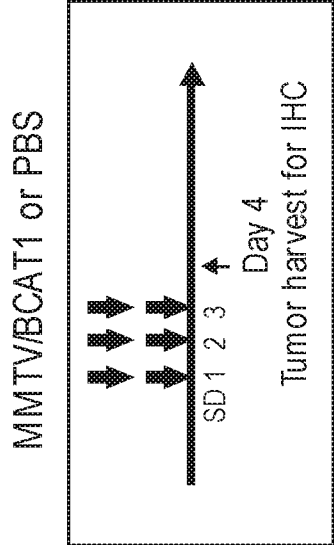
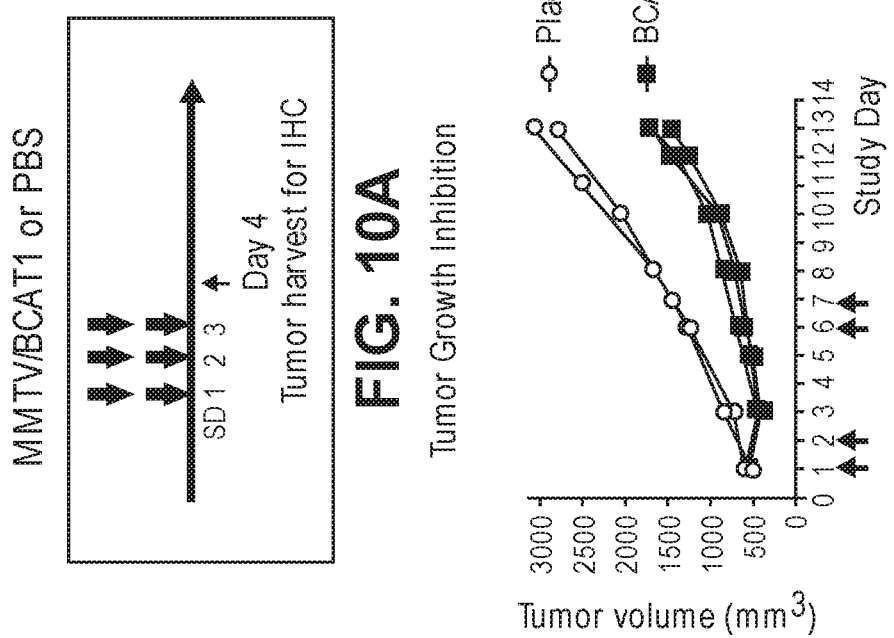
FIG. 10A
FIG. 10B
FIG. 10C

REDUCING BETA-CATENIN AND IDO EXPRESSION TO POTENTIATE IMMUNOTHERAPY

CROSS REFERENCE TO RELATED APPLICATIONS

This application is a U.S. National Stage application of PCT/US2019/012193, filed on Jan. 3, 2019, which claims priority to U.S. Provisional Patent Application No. 62/614,206, filed on Jan. 5, 2018. The entire contents of each related application referenced in this paragraph is incorporated herein by reference in its entirety.

SEQUENCE LISTING

The instant application contains a Sequence Listing which has been filed electronically in ASCII format and is hereby incorporated by reference in its entirety. Said ASCII copy, created on 18 Dec. 2018, is named 0243_0028-PCT_SL.txt and is 2 kilobytes in size.

BACKGROUND

The immune system uses certain molecules on the surface of immune cells as checkpoints to control T cell activation and prevent the immune system from targeting healthy cells and inducing autoimmunity. Certain cancer cells are able to take advantage of these immune checkpoint molecules to evade the immune system. In recent years, immunotherapeutic strategies to block immune checkpoint molecules, such as cytotoxic T-lymphocyte-associated protein-4 (CTLA-4) and programmed cell death receptor 1 (PD-1), have shown success against certain cancers. An anti-CTLA-4 monoclonal antibody (ipilimumab) was approved for the treatment of patients with advanced melanoma in 2011. Two anti-PD-1 monoclonal antibodies (nivolumab and pembrolizumab) were approved for the treatment of patients with certain advanced cancers in 2014. Three anti PD-L1 monoclonal antibodies (atezolizumab, avelumab, and durvalumab) have been approved for advanced cancers since 2016. Antibodies that block immune checkpoint molecules like CTLA-4, PD-1, and PD-L1 appear to release the brakes on T cell activation and promote potent anti-tumor immune responses. However, only a subset of patients responds to this immunotherapy.

At least in certain instances, the tumors that respond to immunotherapy have a pre-existing T cell inflamed phenotype, with infiltrating T cells, a broad chemokine profile that recruits T cells to the tumor microenvironment, and high levels of IFN gamma secretion (also called hot or inflamed tumors). Gajewski et al., Nat Immunol., 2013, 14(10):1014-22; Ji et al., Cancer Immunol Immunother, 2012, 61:1019-31. Conversely, certain tumors that do not respond to immunotherapy have been shown to not have a T cell inflamed phenotype (also known as cold or non-inflamed tumors). Id.

Tumor cells have developed different strategies for evading the immune system. One such strategy involves the expression of the enzyme indoleamine 2,3-dioxygenase-1 (IDO1). IDO1 is an intracellular heme-containing enzyme that catalyzes the degradation of the essential amino acid tryptophan to kynurenine and its downstream catabolites. IDO1 expression promotes an immunosuppressive tumor microenvironment (i.e., cold or non-inflamed tumors) with reduced T-cell infiltration. IDO1 is expressed in many cancers and overexpression of IDO1 is associated with advanced disease stage and tumor metastasis in a variety of cancer types. Munn, Front. Biosci., 2012, (Elite Ed.) 4:734-45. In cancer, IDO1 can be expressed directly by the tumor cells or induced indirectly by antigen-presenting cells in the surrounding microenvironment. Holmgaard et al., Cell Reports, 2015, 13:412-24. Although the mechanisms by which IDO overexpression promotes resistance to immunotherapy is not completely understood, IDO1 is known to inhibit the activation of effector T cells through depletion of the essential amino acid tryptophan and to promote the differentiation and activation of FoxP3 regulatory T cells (Tregs) through production of kynurenine (Munn and Mellor, J. Clin. Invest., 2007, 117:1147-54). Another indoleamine 2,3-dioxygenase isoform (IDO2) is overexpressed in certain solid tumors has also been implicated in immunoresistance, as has tryptophan 2,3-dioxygenase (TDO), which, like IDO1 and IDO2, is a tryptophan catabolic enzyme. Pendergast et al., Cancer Research, 2017, 77(24):6795-6811.

Recently, IDO inhibitors have been shown to boost the effectiveness of certain immunotherapies that target the PD-1/PD-L1 pathway. Phase I/II trials using a combination of the IDO inhibitor, epacadostat (Incyte), with the PD-1 inhibitors, prembrolizumab (Keytruda®) and nivolumab (Opdivo®), have shown positive early results in patients with melanoma. Gangadhar et al., Presented at 2016 European Society for medical Oncology Congress, Oct. 7-11, 2016, Abstract, 1110PD; Perez et al., J. Clin. Oncol., 2017, ASCO abstract, 3003. The combination has also shown efficacy in other tumors, including metastatic or recurrent squamous cell carcinoma of the head and neck, advanced urothelial cell carcinoma, and advanced renal cell carcinoma. Updated Data from ECHO-202 Trial of Incyte's Epacadostat in Combination with Merck's KEYTRUDA® (Pembrolizumab) Demonstrate Clinical Activity across Multiple Tumor Types, joint Incyte and Merck press release from Merck website dated Jun. 5, 2017. A Phase III study of epacadostat and prembrolizumab for unresectable or metastatic melanoma is currently underway. ClinicalTrials.gov Identifier: NCT02752074.

The small molecule IDO inhibitor, indoximod (NewLink Genetics), has shown efficacy in a Phase II study when combined with pembrolizumab in patients with advanced melanoma. Updated Data for Indoximod Plus KEYTRUDA® (pembrolizumab) Demonstrate Improvement of Response Rate for Patients with Advanced Melanoma, press release from NewLink Genetics dated Aug. 7, 2017. Indoximod is also being evaluated in patients with advanced melanoma in combination with the one of the following FDA-approved checkpoint inhibitors: ipilimumab, nivolumab, or pembrolizumab. ClinicalTrials.gov Identifier: NCT02073123. Another IDO inhibitor, BMS-986205, has been shown to be safely tolerated in patients with advanced cancers and studies are being expanded to assess combination therapy with nivolumab and/or ipilimumab. Siu et al., AACR abstract CT116, 2017, 77 (13 suppl). Other IDO inhibitors, like NLG802 (NewLink Genetics) and HTI-1090 (Atridia Pty Ltd), are being evaluated in Phase I studies.

There remains a need in the art to develop new cancer treatment options, including options that would enhance the responsiveness of non-inflamed tumors to immunotherapy.

SUMMARY

This application discloses that reducing β-catenin and IDO expression can significantly enhance the responsiveness of certain tumors to immunotherapy. Without intending to be bound by any theory, it appears that reducing β-catenin and IDO expression can convert certain non-inflamed or cold tumors that are resistant to immunotherapy into inflamed or hot tumors, with increased CD8 T cell infiltration and reduced levels of the immunosuppressive, Foxp3+ regulatory T cells (Tregs). Once converted, the inflamed or hot tumors become responsive to immunotherapy (e.g., blockcade of immune checkpoint molecules). Thus, this application provides methods for converting certain non-inflamed tumors into tumors that are responsive to immunotherapy by reducing both β-catenin and IDO expression.

Typically, expression of β-catenin is reduced by administering a β-catenin nucleic acid inhibitor molecule, including, but not limited to, nucleic acid inhibitor molecules, such as short interfering RNA (siRNA), conventional antisense oligonucleotides, microRNA (miRNA), ribozymes, and aptamers. However, any β-catenin inhibitor can be used in the methods and compositions described herein. As disclosed herein, treating cancer with a combination of β-catenin and IDO inhibitors and immunotherapy not only slows tumor growth, but actually induces tumor regression in an in vivo tumor model.

One aspect is directed to a method of treating cancer in a subject, comprising administering to the subject a therapeutically effective amount of a β-catenin inhibitor, a therapeutically effective amount of an IDO inhibitor, and a therapeutically effective amount of an immunotherapeutic agent. In certain embodiments, the subject is a human.

Another aspect is directed to a pharmaceutical composition comprising a β-catenin inhibitor for use in treating cancer, wherein the composition is administered in combination with an IDO inhibitor and an immunotherapeutic agent.

In certain embodiments of the method or composition, the cancer is a Wnt activated cancer. In certain embodiments of the method or composition, the cancer is a Wnt activated cancer that overexpresses IDO1.

In certain embodiments of the method or composition, the IDO inhibitor comprises epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan. In certain embodiments of the method or composition, the IDO inhibitor comprises epacadostat.

In certain embodiments of the method of composition, the β-catenin inhibitor is a β-catenin nucleic acid inhibitor molecule, including, but not limited to, siRNA, conventional antisense oligonucleotides, miRNA, ribozymes, and aptamers. In certain embodiments of the method of composition, the β-catenin nucleic acid inhibitor molecule is a double stranded RNAi inhibitor molecule comprising a sense strand and an antisense strand that form a region of complementarity, optionally wherein the region of complementarity between the sense strand and the antisense strand is about 15-45 nucleotides.

In certain embodiments of the method of composition, the β-catenin nucleic acid inhibitor molecule is a double stranded RNAi inhibitor molecule comprising a sense stand and an antisense strand and a region of complementarity between the sense strand and the antisense strand of about 15-45, 18-26, or 19-21 nucleotides. In certain embodiments, the sense strand is 15-66 nucleotides and the antisense strand is 15-66 nucleotides. In certain embodiments, the sense strand is 25-40 nucleotides or 19-25 nucleotides. In certain embodiments, the antisense strand is 25-40 nucleotides or 19-25 nucleotides. In certain embodiments, the sense strand is 19-25 nucleotides and the antisense strand is 19-25 nucleotides. In certain embodiments, the sense strand is 26-30 or 34-40 nucleotides and contains a stem and a tetraloop and the antisense strand is 18-24 nucleotides, wherein the sense strand and antisense strand form a duplex region of 18-24 nucleotides. In certain embodiments, the sense strand is 27-29 or 33-39 nucleotides and contains a stem and a triloop and the antisense strand is 18-24 nucleotides, wherein the sense strand and antisense strand form a duplex region of 18-24 nucleotides.

In certain embodiments of the method or composition, the β-catenin nucleic acid inhibitor molecule is a double stranded RNAi inhibitor molecule comprising a sense and an antisense strand and a region of complementarity between the sense strand and the antisense strand of 18-34 nucleotides, wherein the sense strand is 25-36 nucleotides in length and the antisense strand is 26-38 nucleotides in length and comprises a single-stranded overhang of 1-5 nucleotides at its 3'-terminus. In certain embodiments, the antisense strand of the double stranded RNAi inhibitor molecule further comprises a single-stranded overhang of 1-10 nucleotides at its 5'-terminus In certain embodiments of the method or composition, the β-catenin nucleic acid inhibitor molecule is a double stranded RNAi inhibitor molecule comprising a sense and an antisense strand and a region of complementarity between the sense strand and the antisense strand of 20-30, 21-26, 19-24, or 19-21 nucleotides. In certain embodiments, the sense strand has 21 nucleotides and includes a single-stranded overhang of 2 nucleotides at its 3'-terminus, the antisense strand is 21 nucleotides and has a single-stranded overhang of 2 nucleotides at its 3'-end, and sense strand and antisense strand form a duplex region of 19 nucleotides. In certain embodiments, the sense strand is 21 nucleotides, the antisense strand is 23 nucleotides and has a single-stranded overhang of 2 nucleotides at its 3'-end, and sense strand and antisense strand form a duplex region of 21 nucleotides.

In certain embodiments of the method or composition, the β-catenin nucleic acid inhibitor molecule is a double stranded RNAi inhibitor molecule comprising a sense and an antisense strand and a region of complementarity between the sense strand and the antisense strand of 26 nucleotides, wherein the sense strand is 26 nucleotides in length and wherein the antisense strand is 38 nucleotides in length and includes a single-stranded overhang of 2 nucleotides at its 3'-terminus and a single-stranded overhang of 10 nucleotides at its 5'-terminus.

In certain embodiments of the double stranded RNAi inhibitor molecule, the sense strand comprises or consists of the sequence of SEQ ID NO: 1. In certain embodiments of the double stranded RNA inhibitor molecule, the antisense strand comprises or consists of the sequence of SEQ ID NO: 2.

In certain embodiments of the method or composition, the β-catenin nucleic acid inhibitor molecule contains a tetraloop. In certain embodiments of the method or composition, the β-catenin nucleic acid inhibitor molecule contains a triloop.

In certain embodiments of the method or composition, the β-catenin nucleic acid inhibitor molecule is a single-stranded oligonucleotide. In certain embodiments of the method or composition, the β-catenin nucleic acid inhibitor molecule is a conventional antisense oligonucleotide that has a nucleotide sequence in the 5' to 3' direction that comprises the reverse complement of a segment of a human β-catenin gene and is 12-30, 12-25, 12-22, 14-20, or 18-22 nucleotides in length. In certain embodiments, the conventional antisense oligonucleotide is 16-18 or 18-20 nucleotides in length.

In certain embodiments of the method or composition, the immunotherapeutic agent is an antagonist of an inhibitory immune checkpoint molecule or an agonist of a co-stimulatory checkpoint molecule. In certain embodiments, the immunotherapeutic agent is an antagonist of an inhibitory check point, and the inhibitory check point is PD-1 or PD-L1. In certain embodiments, the antagonist of the inhibitory immune checkpoint molecule or the agonist of the co-stimulatory checkpoint molecule is a monoclonal antibody. In certain embodiments, the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

In other embodiments, the immunotherapeutic agent is an antagonist of an inhibitory immune checkpoint molecule, wherein the inhibitory immune checkpoint molecule is a ligand for PD-1, such as PD-L1 or PD-L2; a ligand for CTLA4, such as CD80 or CD86; or a lymphocyte activation gene 3 (LAG3), killer cell immunoglobulin like receptor (KIR), T cell membrane protein 3 (TIM3), galectin 9 (GAL9), or adenosine A2a receptor (A2aR). In certain embodiments, the immunotherapeutic agent is an agonist of a co-stimulatory molecule, wherein the co-stimulatory molecule is CD28, inducible T cell co-stimulator (ICOS), CD137, OX40, or CD27. In other embodiments, the immunotherapeutic agent is an agonist of a ligand of a co-stimulatory molecule, including, for example, CD80, CD86, B7RP1, B7-H3, B7-H4, CD137L, OX40L, or CD70.

In one embodiment, the method of treating cancer in a human subject, comprises administering to the human subject:

a therapeutically effective amount of a β-catenin nucleic acid inhibitor molecule, wherein the β-catenin nucleic acid inhibitor molecule is a double stranded RNAi inhibitor molecule comprising a sense and an antisense strand and a region of complementarity between the sense strand and the antisense strand of 18-34 nucleotides, wherein the sense strand is 19-36 nucleotides in length and the antisense strand is 18-38 nucleotides in length and comprises 1-5 single-stranded nucleotides at its 3'-terminus;

a therapeutically effective amount of an IDO inhibitor, wherein the IDO inhibitor comprises epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan; and a therapeutically effective amount of an immunotherapeutic agent, wherein the immunotherapeutic agent comprises an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody. In one embodiment, the IDO inhibitor comprises epacadostat. In certain embodiments, the cancer is a Wnt activated cancer. In certain embodiments, the cancer is a Wnt activated cancer and that overexpresses IDO1.

In one embodiment, the pharmaceutical composition comprises a β-catenin nucleic acid inhibitor molecule for use in treating cancer, wherein the composition is administered in combination with an IDO inhibitor and an immunotherapeutic agent, wherein the β-catenin nucleic acid inhibitor molecule is a double stranded RNAi inhibitor molecule comprising a sense and an antisense strand and a region of complementarity between the sense strand and the antisense strand of 18-34 nucleotides, wherein the sense strand is 19-36 nucleotides in length and the antisense strand is 19-38 nucleotides in length and comprises 1-5 single-stranded nucleotides at its 3'-terminus, wherein the IDO inhibitor comprises epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan, and wherein the immunotherapeutic agent is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody. In certain embodiments, the IDO inhibitor comprises epacadostat. In certain embodiments, the cancer is a Wnt activated cancer. In certain embodiments, the cancer is a Wnt activated cancer that overexpresses IDO1.

In one embodiment of the method or composition, the region of complementarity between the sense strand and the antisense strand is 21-26 nucleotides, wherein the sense strand is 21-26 nucleotides in length and wherein the antisense strand is 23-38 nucleotides in length and includes a single-stranded overhang of 1-2 nucleotides at its 3'-terminus. In certain embodiments, the antisense strand further comprises a single-stranded overhang of 1-10 nucleotides at its 5'-terminus.

In one embodiment of the method or composition, the region of complementarity between the sense strand and the antisense strand is 19 nucleotides, wherein the sense strand is 21 nucleotides in length and includes a single-stranded overhang of 2 nucleotides at its 3'-terminus and wherein the antisense strand is 21 nucleotides in length and includes a single-stranded overhang of 2 nucleotides at its 3'-terminus. In another embodiment, the region of complementarity between the sense strand and the antisense strand is 21 nucleotides, wherein the sense strand is 21 nucleotides in length and wherein the antisense strand is 23 nucleotides in length and includes a single-stranded overhang of 2 nucleotides at its 3'-terminus.

In certain embodiments of the method or composition, the β-catenin nucleic acid inhibitor molecule is a double stranded RNAi inhibitor molecule comprising a sense and an antisense strand and a region of complementarity between the sense strand and the antisense strand of 26 nucleotides, wherein the sense strand is 26 nucleotides in length and wherein the antisense strand is 38 nucleotides in length and includes a single-stranded overhang of 2 nucleotides at its 3'-terminus and a single-stranded overhang of 10 nucleotides at its 5'-terminus.

In certain embodiments of the method or composition, the sense strand comprises or consists of the sequence of SEQ ID NO: 1 and the antisense strand comprises of consists of the sequence of SEQ ID NO: 2.

In certain embodiments of the method or composition, the sense strand is 34-36 nucleotides and contains a stem and a tetraloop, and the antisense strand is 18-24 nucleotides, wherein the sense strand and antisense strand form a duplex region of 18-24 nucleotides. In certain embodiments of the method or composition, the sense strand is 26-30 nucleotides and contains a stem and a tetraloop, and the antisense strand is 18-24 nucleotides, wherein the sense strand and antisense strand form a duplex region of 18-24 nucleotides, and wherein the stem contains 1, 2, or 3 base pairs and at least one bicyclic nucleotide.

In certain embodiments of the method or composition, the sense strand is 33-35 nucleotides and contains a stem and a triloop, and the antisense strand is 18-24 nucleotides, wherein the sense strand and antisense strand form a duplex region of 18-24 nucleotides. In certain embodiments of the method or composition, the sense strand is 27-29 nucleotides and contains a stem and a triloop, and the antisense strand is 18-24 nucleotides, wherein the sense strand and antisense strand form a duplex region of 18-24 nucleotides, and wherein the stem contains 2 or 3 base pairs and at least one bicyclic nucleotide.

In certain embodiments of the method or composition, the β-catenin nucleic acid inhibitor molecule is formulated with a lipid nanoparticle. In certain embodiments, the lipid nanoparticle comprises a cationic lipid and a pegylated lipid.

In certain embodiments of the method, administering the β-catenin nucleic acid inhibitor molecule, the IDO inhibitor, and the immunotherapeutic agent reduces the amount of cancer in the subject.

In certain embodiments of the method, the subject has been identified as having the non-Wnt activated cancer and/or a cancer that overexpresses IDO1 before the administering step.

In certain embodiments, the method further comprises before the administering step, a step of analyzing a tumor sample from the subject to determine if the subject has the non-Wnt activated cancer.

In certain embodiments of the method or composition, the Wnt activated cancer is resistant to treatment with the immunotherapeutic agent when the immunotherapeutic agent is not administered in combination with the β-catenin nucleic acid inhibitor molecule and the IDO inhibitor.

Another aspect is directed to a method of potentiating a therapeutic effect of an immunotherapeutic agent against a cancer, comprising administering to a subject having the cancer a β-catenin nucleic acid inhibitor molecule, such as the double stranded RNAi inhibitor molecules described herein, and an IDO inhibitor in an amount sufficient to potentiate the therapeutic effect of the immunotherapeutic agent against the cancer. In certain embodiments, the cancer is a Wnt activated cancer. In certain embodiments, the cancer is a Wnt activated cancer that overexpresses IDO1.

In certain embodiments of the method, prior to administering the β-catenin nucleic acid inhibitor molecule and IDO inhibitor, the cancer is associated with a non-T cell inflamed phenotype that is resistant to immunotherapy and wherein administering the β-catenin nucleic acid inhibitor molecule and IDO inhibitor converts the non-T cell inflamed phenotype into a T cell-inflamed phenotype that is responsive to an immunotherapeutic agent.

In certain embodiments, the IDO inhibitor comprises epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan. In certain embodiments, the IDO inhibitor comprises epacadostat.

In certain embodiments, the immunotherapeutic agent is an antagonist of an inhibitory immune checkpoint molecule or an agonist of a co-stimulatory checkpoint molecule. In certain embodiments, the immunotherapeutic agent is an antagonist of an inhibitory check point, and the inhibitory check point is PD-1 or PD-L1. In certain embodiments, the antagonist of the inhibitory immune checkpoint molecule or the agonist of the co-stimulatory checkpoint molecule is a monoclonal antibody. In certain embodiments, the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

In other embodiments, the immunotherapeutic agent is an antagonist of an inhibitory immune checkpoint molecule, wherein the inhibitory immune checkpoint molecule is a ligand for PD-1, such as PD-L1 or PD-L2; a ligand for CTLA4, such as CD80 or CD86; or a lymphocyte activation gene 3 (LAG3), killer cell immunoglobulin like receptor (KIR), T cell membrane protein 3 (TIM3), galectin 9 (GAL9), or adenosine A2a receptor (A2aR). In certain embodiments, the immunotherapeutic agent is an agonist of a co-stimulatory molecule, wherein the co-stimulatory molecule is CD28, inducible T cell co-stimulator (ICOS), CD137, OX40, or CD27. In other embodiments, the immunotherapeutic agent is an agonist of a ligand of a co-stimulatory molecule, including, for example, CD80, CD86, B7RP1, B7-H3, B7-H4, CD137L, OX40L, or CD70.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 1A shows the treatment schedule for Balb/C mice that were implanted with Wnt-activated, 4T1 tumors and treated with placebo or BCAT1, as described in Example 3.

FIG. 1B shows by immunohistochemistry that BCAT1 treatment decreases β-catenin levels and increases CD8 T-cell infiltration but does not significantly reduce IDO1 levels in 4T1 tumors.

FIG. 1C shows that two cycles of BCAT1 treatment inhibits tumor growth as compared to placebo in 4T1 tumors that were implanted into Balb/C mice.

FIG. 3A shows the treatment schedule for Balb/C mice that were implanted with 4T1 tumors and treated with vehicle or an IDO inhibitor (IDOi) called epacadostat, as described in Example 4.

FIG. 3B shows by immunohistochemistry that IDOi treatment decreases β-catenin levels, increases CD8 T-cell infiltration, and decreases IDO1 levels in 4T1 tumors.

FIG. 3C shows that two cycles of IDOi treatment inhibits tumor growth as compared to placebo in 4T1 tumors that were implanted into Balb/C mice.

FIG. 6A shows the treatment schedule for C57BL/6 mice that were implanted with non-Wnt activated, B16F10 tumors and treated with placebo or BCAT1, as described in Example 6.

FIG. 6B shows by immunohistochemistry that BCAT1 treatment decreases β-catenin levels, increases CD8 T-cell infiltration, and reduces IDO1 levels in B16F10 tumors.

FIG. 6C shows that two cycles of BCAT1 treatment does not significantly inhibit tumor growth as compared to placebo in B16F10 tumors that were implanted into C57BL/6 mice.

FIG. 8A shows the treatment schedule for C57BL/6 mice that were implanted with B16F10 tumors and treated with vehicle or an IDO inhibitor (IDOi) called epacadostat, as described in Example 7.

FIG. 8B shows by immunohistochemistry that IDOi treatment decreases β-catenin levels, increases CD8 T-cell infiltration, and decreases IDO1 levels in B16F10 tumors.

FIG. 8C shows that two cycles of IDOi treatment does not significantly inhibit tumor growth as compared to placebo in B16F10 tumors that were implanted in C57BL/6 mice.

FIG. 10A shows the treatment schedule for MMTV-Wnt tumor-bearing mice that were treated with placebo or BCAT1, as described in Example 9.

FIG. 10B shows by immunohistochemistry that BCAT1 treatment decreases β-catenin levels and increases CD8 T-cell infiltration but does not significantly reduce IDO1 levels in MMTV-Wnt tumors.

FIG. 10C shows that two cycles of BCAT1 treatment inhibits tumor growth as compared to placebo in MMTV-Wnt tumor-bearing mice.

DEFINITIONS

Figure 2A:
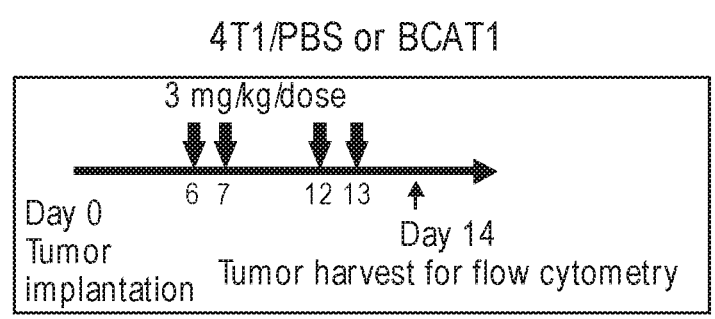
FIG. 2A shows the treatment schedule for Balb/C mice that were implanted with 4T1 tumors and treated with PBS or BCAT1, as described in Example 3.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

Administer: As used herein, "administering" a composition to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Acyl: As used herein, the term "acyl" refers to an alkylcarbonyl, cycloalkylcarbonyl and arylcarbonyl moiety.

Alkoxy: As used herein, the term "alkoxy" refers to an alkyl group attached to a molecular moiety through an oxygen atom.

Alkenyl: As used herein, the term "alkenyl" refers to straight or branched chain hydrocarbyl groups having at least one carbon-carbon double bond, and having in the range of about 2 to about 20 carbon atoms. "Substituted alkenyl" refers to alkenyl groups further bearing one or more substituents. As used herein, "lower alkenyl" refers to alkenyl moieties having from 2 to about 6 carbon atoms.

Alkyl: As used herein, the term "alkyl" refers to straight or branched chain hydrocarbyl groups having from 1 up to about 20 carbon atoms. Whenever it appears herein, a numerical range, such as "$C_1$-$C_6$ alkyl" means that an alkyl group may comprise only 1 carbon atom, 2 carbon atoms, 3 carbon atoms, etc., up to and including 6 carbon atoms, although the term "alkyl" also includes instances where no numerical range of carbon atoms is designated. For example, the term "alkyl" can refer to a sub-range between $C_1$-$C_{10}$ (e.g. $C_1$-$C_6$). "Substituted alkyl" refers to alkyl moieties bearing substituents. As used herein, "lower alkyl" refers to alkyl moieties having from 1 to about 6 carbon atoms.

Alkynyl: As used herein, "alkynyl" refers to straight or branched chain hydrocarbyl groups having at least one carbon-carbon triple bond, and having in the range of about 2 to about 20 carbon atoms. "Substituted alkynyl" refers to alkynyl groups further bearing one or more substituents. As used herein, "lower alkynyl" refers to alkynyl moieties having from about 2 to about 6 carbon atoms.

Antibody: As used herein, the term "antibody" refers to an immunoglobulin or an antigen-binding domain thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

Antigen-Binding Domain: As used herein, the term "antigen-binding domain" refers to a part of an antibody molecule that comprises amino acids responsible for the specific binding between antibody and antigen. For certain antigens, the antigen-binding domain may only bind to a part of the antigen. The part of the antigen that is specifically recognized and bound by the antibody is referred to as the "epitope" or "antigenic determinant." Antigen-binding domains include Fab (Fragment antigen-binding); a F(ab')$_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Nat. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The Fv fragment is smaller and has $V_H$ and $V_L$ domains non-covalently linked. To overcome the tendency of non-covalently linked domains to dissociate, a scFv can be constructed. The scFv contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide may be used as a linker, but other linkers are known in the art. These antibody fragments are obtained using conventional techniques known to those with skill in the art, and the fragments are evaluated for function in the same manner as are intact antibodies.

Antisense strand: A dsRNAi inhibitor molecule comprises two oligonucleotide strands: an antisense strand and a sense strand. The antisense strand or a region thereof is partially, substantially or fully complementary to a corresponding region of a target nucleic acid. In addition, the antisense strand of the double stranded RNAi inhibitor molecule or a region thereof is partially, substantially or fully complementary to the sense strand of the double stranded RNAi inhibitor molecule or a region thereof. In certain embodiments, the antisense strand may also contain nucleotides that are non-complementary to the target nucleic acid sequence. The non-complementary nucleotides may be on either side of the complementary sequence or may be on both sides of the complementary sequence. In certain embodiments, where the antisense strand or a region thereof is partially or substantially complementary to the sense strand or a region thereof, the non-complementary nucleotides may be located between one or more regions of complementarity (e.g., one or more mismatches). The antisense strand of a double stranded RNAi inhibitor molecule is also referred to as the guide strand.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aryl: As used herein, the term "aryl" refers to an aromatic monocyclic or multicyclic groups having in the range of 5 up to 19 carbon atoms. "Substituted aryl" refers to aryl groups further bearing one or more substituents.

β-catenin: As used herein, "β-catenin" refers either to a polypeptide or a nucleic acid sequence encoding such a β-catenin protein. When referring to a polypeptide, "β-catenin" refers to the polypeptide gene product of a β-catenin gene/transcript (CTNNB1) (Genbank Accession Nos. NM_001904.3 (human β-catenin transcript variant 1), NM_001098209.1 (human β-catenin transcript variant 2), NM_001098210.1 (human β-catenin transcript variant 3), and NM_007614.2 & NM_007614.3 (mouse β-catenin).

BCAT: As used herein "BCAT1" refers to a nucleic acid inhibitor molecule that targets the β-catenin gene and has a sense strand with a nucleic acid sequence consisting of SEQ ID NO:1 and an antisense strand with a nucleic acid sequence consisting of SEQ ID NO:2.

Bicyclic nucleotide: As used herein, the term "bicyclic nucleotide" refers to a nucleotide comprising a bicyclic sugar moiety.

Bicyclic sugar moiety: As used herein, the term "bicyclic sugar moiety" refers to a modified sugar moiety comprising a 4 to 7 membered ring (including but not limited to a furanosyl) comprising a bridge connecting two atoms of the 4 to 7 membered ring to form a second ring, resulting in a bicyclic structure. Typically, the 4 to 7 membered ring is a sugar. In some embodiments, the 4 to 7 member ring is a furanosyl. In certain embodiments, the bridge connects the 2'-carbon and the 4'-carbon of the furanosyl.

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. "Fully complementary" or 100% complementarity refers to the situation in which each nucleotide monomer of a first oligonucleotide strand or of a segment of a first oligonucleotide strand can form a base pair with each nucleotide monomer of a second oligonucleotide strand or of a segment of a second oligonucleotide strand. Less than 100% complementarity refers to the situation in which some, but not all, nucleotide monomers of two oligonucleotide strands (or two segments of two oligonucleotide strands) can form base pairs with each other. "Substantial complementarity" refers to two oligonucleotide strands (or segments of two oligonucleotide strands) exhibiting 90% or greater complementarity to each other. "Sufficiently complementary" refers to complementarity between a target mRNA and a nucleic acid inhibitor molecule, such that there is a reduction in the amount of protein encoded by a target mRNA.

Complementary strand: As used herein, the term "complementary strand" refers to a strand of a double stranded nucleic acid inhibitor molecule that is partially, substantially or fully complementary to the other strand.

Conventional antisense oligonucleotide: As used herein, the term "conventional antisense oligonucleotide" refers to single stranded oligonucleotides that inhibit the expression of a targeted gene by one of the following mechanisms: (1) Steric hindrance, e.g., the antisense oligonucleotide interferes with some step in the sequence of events involved in gene expression and/or production of the encoded protein by directly interfering with, for example, transcription of the gene, splicing of the pre-mRNA and translation of the mRNA; (2) Induction of enzymatic digestion of the RNA transcripts of the targeted gene by RNase H; (3) Induction of enzymatic digestion of the RNA transcripts of the targeted gene by RNase L; (4) Induction of enzymatic digestion of the RNA transcripts of the targeted gene by RNase P: (5) Induction of enzymatic digestion of the RNA transcripts of the targeted gene by double stranded RNase; and (6) Combined steric hindrance and induction of enzymatic digestion activity in the same antisense oligo. Conventional antisense oligonucleotides do not have an RNAi mechanism of action like RNAi inhibitor molecules. RNAi inhibitor molecules can be distinguished from conventional antisense oligonucleotides in several ways including the requirement for Ago2 that combines with an RNAi antisense strand such that the antisense strand directs the Ago2 protein to the intended target(s) and where Ago2 is required for silencing of the target.

Cycloalkyl: As used herein, the term "cycloalkyl" refers to cyclic (i.e., ring-containing) hydrocarbon groups containing 3 to 12 carbons, for example, 3 to 8 carbons and, for example, 3 to 6 carbons.

Deoxyribofuranosyl: As used herein, the term "deoxyribofuranosyl" refers to a furanosyl that is found in naturally occurring DNA and has a hydrogen group at the 2'-carbon, as illustrated below:

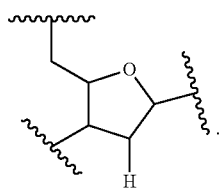 [SMILES: *CC1OC(*)CC1*]

Deoxyribonucleotide: As used herein, the term "deoxyribonucleotide" refers to a natural nucleotide (as defined herein) or modified nucleotide (as defined herein) which has a hydrogen group at the 2'-position of the sugar moiety.

Duplex: As used herein, the term "duplex," in reference to nucleic acids (e.g., oligonucleotides), refers to a structure formed through complementary base pairing of two antiparallel sequences of nucleotides.

Excipient: As used herein, the term "excipient" refers to a non-therapeutic agent that may be included in a composition, for example to provide or contribute to a desired consistency or stabilizing effect.

Furanosyl: As used herein, the term "furanosyl" refers to a structure comprising a 5-membered ring with four carbon atoms and one oxygen atom.

Halogen: As used herein, the term "halogen" refers to an atom selected from fluorine, chlorine, bromine and iodine.

Heterocycle: As used herein, the terms "heterocycle" or "heterocyclic" refer to non-aromatic cyclic (i.e., ring-containing) groups containing one or more heteroatoms (e.g., N, O, S, or the like) as part of the ring structure, and having in the range of 3 up to 14 carbon atoms. "Substituted heterocyclic" or "substituted heterocycle" refer to heterocyclic groups further bearing one or more substituents.

IDO inhibitor: As used herein, the term "IDO inhibitor" refers to a compound or agent that reduces an activity of an indoleamine 2,3-dioxygenase ("IDO") enzyme.

Internucleotide linking group: As used herein, the term "internucleotide linking group" or "internucleotide linkage" refers to a chemical group capable of covalently linking two nucleoside moieties. Typically, the chemical group is a phosphorus-containing linkage group containing a phospho or phosphite group. Phospho linking groups are meant to include a phosphodiester linkage, a phosphorodithioate linkage, a phosphorothioate linkage, a phosphotriester linkage, a thionoalkylphosphonate linkage, a thionalkylphosphotriester linkage, a phosphoramidite linkage, a phosphonate linkage and/or a boranophosphate linkage. Many phosphorus-containing linkages are well known in the art, as disclosed, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050. In other embodiments, the oligonucleotide contains one or more internucleotide linking groups that do not contain a phosphorous atom, such short chain alkyl or cycloalkyl internucleotide linkages, mixed heteroatom and alkyl or cycloalkyl internucleotide linkages, or one or more short chain heteroatomic or heterocyclic internucleotide linkages, including, but not limited to, those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; and amide backbones. Non-phosphorous containing linkages are well known in the art, as disclosed, for example, in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Immune checkpoint molecules: As used herein, the term "immune checkpoint molecule" refers to molecules on immune cells, such as T cells, that are important under normal physiological conditions for the maintenance of self-tolerance (or the prevention of autoimmunity) and the protection of host cells and tissue when the immune system responds to a foreign pathogen. Certain immune checkpoint molecules are co-stimulatory molecules that amplify a signal involved in the T cell response to antigen while certain immune checkpoint molecules are inhibitory molecules (e.g., CTLA-4 or PD-1) that reduce a signal involved in the T cell response to antigen.

Loop: As used herein, the term "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins, tetraloops, and triloops.

Modified nucleobase: As used herein, the term "modified nucleobase" refers to any nucleobase that is not a natural nucleobase or a universal nucleobase. Suitable modified nucleobases include diaminopurine and its derivatives, alkylated purines or pyrimidines, acylated purines or pyrimidines thiolated purines or pyrimidines, and the like. Other suitable modified nucleobases include analogs of purines and pyrimidines. Suitable analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, hypoxanthine, xanthine, 2-aminopurine, 6-hydroxyaminopurine, nitropyrrolyl, nitroindolyl and difluorotolyl, 6-thiopurine and 2,6-diaminopurine nitropyrrolyl, nitroindolyl and difluorotolyl. Typically a nucleobase contains a nitrogenous base. In certain embodiments, the nucleobase does not contain a nitrogen atom. See e.g., U.S. Published Patent Application No. 20080274462.

Modified nucleoside: As used herein, the term "modified nucleoside" refers to a heterocyclic nitrogenous base in N-glycosidic linkage with a sugar (e.g., deoxyribose or ribose or analog thereof) that is not linked to a phosphate group or a modified phosphate group (as defined herein) and that contains one or more of a modified nucleobase (as defined herein), a universal nucleobase (as defined herein) or a modified sugar moiety (as defined herein). The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). Suitable modified or universal nucleobases or modified sugars in the context of the present disclosure are described herein.

Modified nucleotide: As used herein, the term "modified nucleotide" refers to a heterocyclic nitrogenous base in N-glycosidic linkage with a sugar (e.g., ribose or deoxyribose or analog thereof) that is linked to a phosphate group or a modified phosphate group (as defined herein) and contains one or more of a modified nucleobase (as defined herein), universal nucleobase (as defined herein), a modified sugar moiety (as defined herein), or a modified phosphate group (as defined herein). The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). Suitable modified or universal nucleobases, modified sugar moieties, or modified phosphate groups in the context of the present disclosure are described herein.

Modified phosphate group: As used herein, the term "modified phosphate group" refers to a modification of the phosphate group that does not occur in natural nucleotides and includes non-naturally occurring phosphate mimics as described herein, including phosphate mimics that include a phosphorous atom and anionic phosphate mimics that do not include phosphate (e.g. acetate). Modified phosphate groups also include non-naturally occurring internucleotide linking groups, including both phosphorous-containing internucleotide linking groups including, for example, phosphorothioate, and non-phosphorous containing linking groups, as described herein. Suitable modified or universal nucleobases, modified sugar moieties, or modified phosphates in the context of the present disclosure are described herein.

Modified sugar moiety: As used herein, a "modified sugar moiety" refers to a substituted sugar moiety (as defined herein) or a sugar analog (as defined herein).

Naked oligonucleotide: As used herein, the term "naked oligonucleotide" refers to an oligonucleotide that is not formulated in a protective lipid nanoparticle or other protective formulation and is thus exposed to the blood and endosomal/lysosomal compartments when administered in vivo.

Natural nucleobase: As used herein, the term "natural nucleobase" refers to the five primary, naturally occurring heterocyclic nucleobases of RNA and DNA, i.e., the purine bases: adenine (A) and guanine (G), and the pyrimidine bases: thymine (T), cytosine (C), and uracil (U).

Natural sugar moiety: As used herein, the term "natural sugar moiety" refers to a ribofuranosyl (as defined herein) or a deoxyribofuranosyl (as defined herein).

Natural nucleoside: As used herein, the term "natural nucleoside" refers to a natural nucleobase (as defined herein) in N-glycosidic linkage with a natural sugar moiety (as defined herein) that is not linked to a phosphate group.

Natural nucleotide: As used herein, the term "natural nucleotide" refers to a natural nucleobase (as defined herein) in N-glycosidic linkage with a natural sugar moiety that is linked to a phosphate group.

non-T cell inflamed phenotype: As used herein, "non-T cell inflamed phenotype" refers to a tumor microenvironment without a pre-existing T cell response against the tumor, as evidenced by little to no accumulation of infiltrating CD8+ T cells in the tumor microenvironment. Typically, the non-T cell inflamed phenotype is also characterized by a limited chemokine profile that does not promote the recruitment and accumulation of CD8+ T cells in the tumor microenvironment and/or a minimal or absent type I IFN gene signature.

non-Wnt activated disease or disorder: As used herein, a "non-Wnt activated" disease or disorder refers to a disease or disorder that is not associated with activation of the Wnt/β-catenin pathway. A "non-Wnt activated" disease or disorder includes certain cancer and/or proliferative diseases, conditions, or disorders, including certain colorectal, desmoid, endometrial, gastric, hepatocellular, hepatoblastoma, kidney (Wilms' tumor), medulloblastoma, melanoma, neuroblastoma, ovarian (endometrioid), pancreatic, pilomatricoma, prostate, renal, thyroid (anaplastic) and uterine (endometrium) cancers. In one embodiment, the "non-Wnt activated" disease or disorder is colorectal cancer, hepatocellular carcinoma, or melanoma. In one embodiment, the "non-Wnt activated" disease or disorder is neuroblastoma, renal cancer, or melanoma. It is understood that a disease or disorder, including the cancer and/or proliferative diseases listed above, may include both a non-Wnt activated sub-type of the disease or disorder and a Wnt activated sub-type of the disease or disorder, consistent with the definition of Wnt activated disease or disorder provided below.

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. The nucleic acid inhibitor molecule may include ribonucleotides, deoxyribonucleotides, and/or modified nucleotides.

Nucleobase: As used herein, the term "nucleobase" refers to a natural nucleobase (as defined herein), a modified nucleobase (as defined herein), or a universal nucleobase (as defined herein).

Nucleoside: As used herein, the term "nucleoside" refers to a natural nucleoside (as defined herein) or a modified nucleoside (as defined herein).

Nucleotide: As used herein, the term "nucleotide" refers to a natural nucleotide (as defined herein) or a modified nucleotide (as defined herein).

Overhang: As used herein, the term "overhang" refers to terminal non-base pairing nucleotide(s) at either end of either strand of a double-stranded nucleic acid inhibitor molecule. In certain embodiments, the overhang results from one strand or region extending beyond the terminus of the complementary strand to which the first strand or region forms a duplex. One or both of two oligonucleotide regions that are capable of forming a duplex through hydrogen bonding of base pairs may have a 5'- and/or 3'-end that extends beyond the 3'- and/or 5'-end of complementarity shared by the two polynucleotides or regions. The single-stranded region extending beyond the 3'- and/or 5'-end of the duplex is referred to as an overhang.

Pharmaceutical composition: As used herein, the term "pharmaceutical composition" comprises a pharmacologically effective amount of a β-catenin nucleic acid inhibitor molecule, an IDO inhibitor, or an immunotherapeutic agent, such as an antibody (including, for example, one or more of an anti-CTLA-4, anti-PD-1, or anti-PD-L1 antibody) and a pharmaceutically acceptable excipient. As used herein, "pharmacologically effective amount," "therapeutically effective amount" or "effective amount" refers to that amount of a β-catenin nucleic acid inhibitor molecule, an IDO inhibitor, or an immunotherapeutic agent, such as an antibody (including, for example, one or more of an anti-CTLA-4, anti-PD-1, or anti-PD-L1 antibody) effective to produce the intended pharmacological, therapeutic or preventive result.

Pharmaceutically acceptable excipient: As used herein, the term "pharmaceutically acceptable excipient" means that the excipient is one that is suitable for use with humans and/or animals without undue adverse side effects (such as toxicity, irritation, and allergic response) commensurate with a reasonable benefit/risk ratio.

Phosphate mimic: As used herein, the term "phosphate mimic" refers to a chemical moiety at the 5'-terminal end of an oligonucleotide that mimics the electrostatic and steric properties of a phosphate group. Many phosphate mimics have been developed that can be attached to the 5'-end of an oligonucleotide (see, e.g., U.S. Pat. No. 8,927,513; Prakash et al. *Nucleic Acids Res.*, 2015, 43(6):2993-3011). Typically, these 5'-phosphate mimics contain phosphatase-resistant linkages. Suitable phosphate mimics include 5'-phosphonates, such as 5'-methylenephosphonate (5'-MP) and 5'-(E)-vinylphosphonate (5'-VP) and 4'-phosphate analogs that are bound to the 4'-carbon of the sugar moiety (e.g., a ribose or deoxyribose or analog thereof) of the 5'-terminal nucleotide of an oligonucleotide, such as 4'-oxymethylphosphonate, 4'-thiomethylphosphonate, or 4'-aminomethylphosphonate, as described in PCT International Publication No. WO 2018/045317, which is hereby incorporated by reference in its entirety. In certain embodiments, the 4'-oxymethylphosphonate is represented by the formula —O—CH$_2$—PO(OH)$_2$ or —O—CH$_2$—PO(OR)$_2$, where R is independently selected from H, C$_H$3, an alkyl group, or a protecting group. In certain embodiments, the alkyl group is CH$_2$CH$_3$. More typically, R is independently selected from H, CH$_3$, or CH$_2$CH$_3$. Other modifications have been developed for the 5'-end of oligonucleotides (see, e.g., WO 2011/133871).

Potentiate: The term "potentiate" or "potentiating" as used herein refers to the ability of one or more therapeutic agents (e.g., a β-catenin nucleic acid inhibitor molecule and IDO inhibitor) to increase or enhance the therapeutic effect of another therapeutic agent (e.g., an antagonist of an inhibitory immune checkpoint molecule, such as CTLA-4 or PD-1, or an agonist of a co-stimulatory checkpoint molecule).

Protecting group: As used herein, the term "protecting group" is used in the conventional chemical sense as a group which reversibly renders unreactive a functional group under certain conditions of a desired reaction. After the desired reaction, protecting groups may be removed to deprotect the protected functional group. All protecting groups should be removable under conditions which do not degrade a substantial proportion of the molecules being synthesized.

Reduce(s): The term "reduce" or "reduces" as used herein refers to its meaning as is generally accepted in the art. With reference to exemplary nucleic acid inhibitor molecules (e.g., β-catenin RNAi inhibitor molecules), the term generally refers to the reduction in the expression of a gene, or level of RNA molecules or equivalent RNA molecules encoding one or more proteins or protein subunits, or activity of one or more proteins or protein subunits, below that observed in the absence of the nucleic acid inhibitor molecules.

Resistance: The term "resistance" or "resistant" as used in relation to immunotherapy refers to a cancer and/or proliferative disease, condition or disorder that does not show a medically significant response to immunotherapy. As disclosed herein, resistance to immunotherapy can be reversed by reducing β-catenin and IDO expression.

Ribofuranosyl: As used herein, the term "ribofuranosyl" refers to a furanosyl that is found in naturally occurring RNA and has a hydroxyl group at the 2'-carbon, as illustrated below:

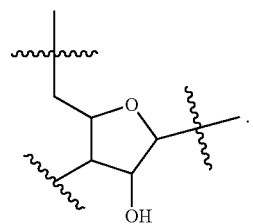 [SMILES: *CC1OC(*)C(O)C1*]

Ribonucleotide: As used herein, the term "ribonucleotide" refers to a natural nucleotide (as defined herein) or a modified nucleotide (as defined herein) which has a hydroxyl group at the 2'-position of the sugar moiety.

RNAi inhibitor molecule: As used herein, the term "RNAi inhibitor molecule" refers to either (a) a double stranded nucleic acid inhibitor molecule ("dsRNAi inhibitor molecule") having a sense strand (passenger) and antisense strand (guide), where the antisense strand or part of the antisense strand is used by the Argonaute 2 (Ago2) endonuclease in the cleavage of a target mRNA or (b) a single stranded nucleic acid inhibitor molecule ("ssRNAi inhibitor molecule") having a single antisense strand, where the antisense strand (or part of the antisense strand) is used by the Ago2 endonuclease in the cleavage of a target mRNA.

Sense strand: A dsRNAi inhibitor molecule comprises two oligonucleotide strands: an antisense strand and a sense strand. The sense strand or a region thereof is partially, substantially or fully complementary to the antisense strand of the dsRNAi inhibitor molecule or a region thereof. In certain embodiments, the sense strand may also contain nucleotides that are non-complementary to the antisense strand. The non-complementary nucleotides may be on either side of the complementary sequence or may be on both sides of the complementary sequence. In certain embodiments, where the sense strand or a region thereof is partially or substantially complementary to the antisense strand or a region thereof, the non-complementary nucleotides may be located between one or more regions of complementarity (e.g., one or more mismatches). The sense strand is also called the passenger strand.

Subject: As used herein, the term "subject" means any mammal, including mice, rabbits, and humans. In one embodiment, the subject is a human. The terms "individual" or "patient" are intended to be interchangeable with "subject."

Substituent or substituted: The terms "substituent" or "substituted" as used herein refer to the replacement of hydrogen radicals in a given structure with the radical of a substituent. When more than one position in any given structure may be substituted with more than one substituent, the substituent may be either the same or different at every position unless otherwise indicated. As used herein, the term "substituted" is contemplated to include all permissible substituents that are compatible with organic compounds. The permissible substituents include acyclic and cyclic, branched and unbranched, carbocyclic and heterocyclic, aromatic and nonaromatic substituents of organic compounds. This disclosure is not intended to be limited in any manner by the permissible substituents of organic compounds.

Substituted sugar moiety: As used herein, a "substituted sugar moiety" includes furanosyls comprising one or more modifications. Typically, the modifications occur at the 2'-, 3'-, 4'-, or 5'-carbon position of the sugar. In certain embodiments, the substituted sugar moiety is a bicyclic sugar moiety comprising a bridge that connects the 2'-carbon with the 4-carbon of the furanosyl.

Sugar analog: As used herein, the term "sugar analog" refers to a structure that does not comprise a furanosyl and that is capable of replacing the naturally occurring sugar moiety of a nucleotide, such that the resulting nucleotide is capable of (1) incorporation into an oligonucleotide and (2) hybridization to a complementary nucleotide. Such structures typically include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties. Sugar analogs also include more complex sugar replacements (e.g., the non-ring systems of peptide nucleic acid). Sugar analogs include without limitation morpholinos, cyclohexenyls and cyclohexitols.

Sugar moiety: As used herein, the term "sugar moiety" refers to a natural sugar moiety or a modified sugar moiety of a nucleotide or nucleoside.

Target site: As used herein, the term "target site" "target sequence," "target nucleic acid", "target region," "target gene" are used interchangeably and refer to a RNA or DNA sequence that is "targeted," e.g., for cleavage mediated by an RNAi inhibitor molecule that contains a sequence within its guide/antisense region that is partially, substantially, or perfectly or sufficiently complementary to that target sequence.

T cell-inflamed tumor phenotype: As used herein, "T cell-inflamed phenotype" refers to a tumor microenvironment with a pre-existing T cell response against the tumor, as evidenced by an accumulation of infiltrating CD8+ T cells in the tumor microenvironment. Typically, the T cell-inflamed phenotype is also characterized by a broad chemokine profile capable of recruiting CD8+ T cells to the tumor microenvironment (including CXCL9 and/or CXCL10) and/or a type I IFN gene signature.

TDO Inhibitor: As used herein, the term "TDO inhibitor" refers to a compound or agent that reduces an activity of a tryptophan 2,3-dioxygenase ("TDO") enzyme.

Tetraloop: As used herein, the term "tetraloop" refers to a loop (a single stranded region) that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the nucleotides in a tetraloop include but are not limited to non-Watson-Crick base pairing, stacking interactions, hydrogen bonding, and contact interactions (Cheong et al., *Nature*, 1990, 346(6285):680-2; Heus and Pardi, *Science*, 1991, 253(5016):191-4). A tetraloop confers an increase in the melting temperature (Tm) of an adjacent duplex that is higher than expected from a simple model loop sequence consisting of random bases. For example, a tetraloop can confer a melting temperature of at least 50° C., at least 55° C., at least 56° C., at least 58° C., at least 60° C., at least 65° C. or at least 75° C. in 10 mM NaHPO4 to a hairpin comprising a duplex of at least 2 base pairs in length. A tetraloop may contain ribonucleotides, deoxyribonucleotides, modified nucleotides, and combinations thereof. In certain embodiments, a tetraloop consists of four nucleotides. In certain embodiments, a tetraloop consists of five nucleotides.

Examples of RNA tetraloops include the UNCG family of tetraloops (e.g., UUCG), the GNRA family of tetraloops (e.g., GAAA), and the CUUG tetraloop. (Woese et al., *PNAS*, 1990, 87(21):8467-71; Antao et al., *Nucleic Acids Res.*, 1991, 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). (Nakano et al. *Biochemistry*, 2002, 41(48):14281-14292. Shinji et al., *Nippon Kagakkai Koen Yokoshu*, 2000, 78(2):731).

Therapeutically effective amount: As used herein, a "therapeutically effective amount" or "pharmacologically effective amount" means an amount of a compound or compounds effective to produce the intended pharmacological, therapeutic or preventive result.

Triloop: As used herein, the term "triloop" refers to a loop (a single stranded region) that forms a stable secondary structure that contributes to the stability of an adjacent Watson-Crick hybridized nucleotides and consists of three nucleotides. Without being limited to theory, a triloop may be stabilized by non-Watson-Crick base pairing of nucleotides within the triloop and base-stacking interactions. (Yoshizawa et al., Biochemistry 1997; 36, 4761-4767). A triloop can also confer an increase in the melting temperature (Tm) of an adjacent duplex that is higher than expected from a simple model loop sequence consisting of random bases. A triloop may contain ribonucleotides, deoxyribonucleotides, modified nucleotides, and combinations thereof. Examples of triloops include the GNA family of triloops (e.g., GAA, GTA, GCA, and GGA). (Yoshizawa 1997). In certain embodiments, the triloop has a nucleotide sequence of GAA.

Universal nucleobase: As used herein, a "universal nucleobase" refers to a base that can pair with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. The universal nucleobase may base pair by forming hydrogen bonds via Watson-Crick or non-Watson-Crick interactions (e.g., Hoogsteen interactions). Representative universal nucleobases include inosine and its derivatives.

Wnt activated disease or disorder: As used herein, a "Wnt activated" disease or disorder refers to a disease or disorder that is associated with an activated Wnt/β-catenin pathway. A "Wnt-associated" disease or disorder includes cancer and/or proliferative diseases, conditions, or disorders, including colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers. In one embodiment, the "Wnt activated" disease or disorder is colorectal cancer, hepatocellular carcinoma, or melanoma. It is understood that a disease or disorder, including the cancer and/or proliferative diseases listed above, may include both a Wnt activated version of the disease or disorder and a non-Wnt activated version of the disease or disorder, consistent with the definition of non-Wnt activated disease or disorder provided above.

Figure 14:
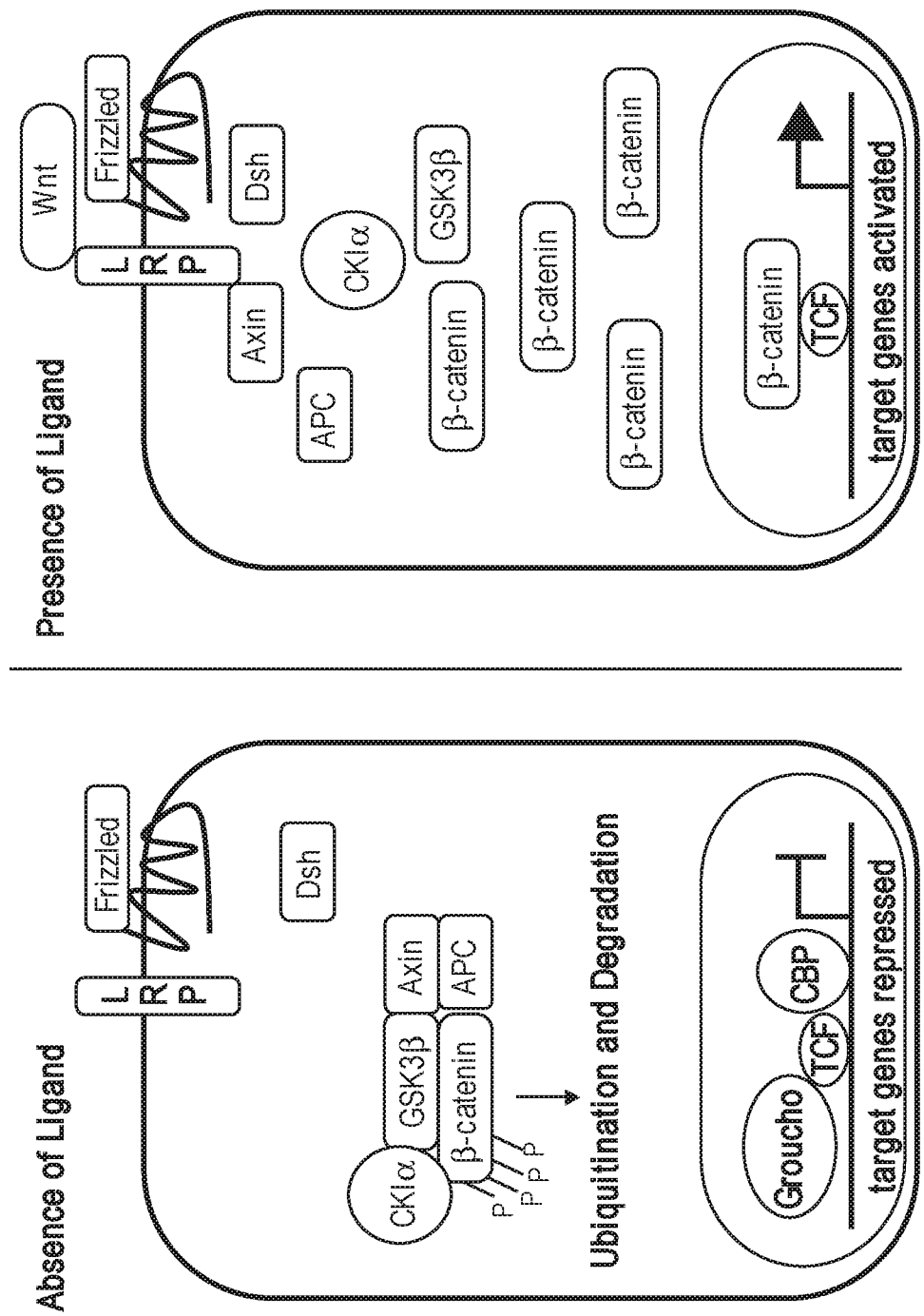
FIG. 14 shows a simplified diagram of the Wnt signaling pathway. The left side depicts a cell where the Wnt ligand is not bound to its surface receptor, β-catenin is sequestered in a destruction complex and targeted for ubiquitination and degradation, and target genes are repressed. The right side depicts a cell after the Wnt ligand has bound its surface receptor, where the destruction complex disassembles, stabilized β-catenin is released and travels to the nucleus, and target genes are activated.

Wnt/β-catenin pathway: As used herein the "Wnt/β-catenin pathway" refers to a molecular signaling pathway in cells that is mediated through a combination of Wnt ligands, receptors, and co-receptors, which initiate a downstream signaling pathway that involves β-catenin (see e.g., FIG. 14). In the absence of Wnt signaling, β-catenin is targeted for degradation via ubiquitination in the cellular cytoplasm. In the presence of Wnt ligand and Wnt signaling, β-catenin is stabilized and travels to the cell nucleus where it can interact with transcription factors, such as T cell transcription factor (TCF) and lymphoid enhanced transcription factor (LEF), and activate gene transcription. Deregulation and activation of the Wnt/β-catenin pathway is most often caused by mutations in the β-catenin gene or the gene encoding adenomatous polyposis coli (APC), which negatively regulates β-catenin function, but can also be caused by a mutation in a gene encoding other components of the Wnt/β-catenin pathway, such as Axin, LEF, and ICAT.

DETAILED DESCRIPTION

This application provides new methods and compositions for treating cancer, including cancer that is not responsive to immunotherapy (e.g., blockade of immune checkpoint molecules). Typically, cancer that is not responsive to immunotherapy is characterized by a non-T cell inflamed phenotype (also known as cold or non-inflamed tumors), with little to no infiltrating CD8+ T cells in the tumor microenvironment. As disclosed in PCT International Publication No. WO 2018/183420, reducing β-catenin expression can convert a cold or non-inflamed tumor into a hot or inflamed tumor and potentiate the effect of immunotherapy, even in tumors that do not have an activated Wnt/β-catenin pathway. In other words, by combining a β-catenin inhibitor, such as a β-catenin nucleic acid inhibitor molecule, with immunotherapy, it is possible to treat cold or non-inflamed tumors that normally do not respond to immunotherapy. As disclosed in PCT International Publication No. WO 2018/183420, this combination therapy approach was used to inhibit tumor growth in vivo across a broad variety of cancers, including cancers with and without an activated Wnt/β-catenin pathway.

This application demonstrates that reducing both IDO expression and β-catenin expression is another strategy for converting certain cold or non-inflamed tumors into hot or inflamed tumors and potentiating the effect of immunotherapy. While the combination of a β-catenin inhibitor and immunotherapy was shown to significantly slow tumor growth in a mouse model of cancer, the triple combination of a β-catenin inhibitor, an IDO inhibitor and immunotherapy actually induced tumor regression in the same mouse model. Thus, reducing both β-catenin and IDO expression can enhance the susceptibility of certain non-inflamed or cold tumors to immunotherapy and provides improved methods for treating certain cold or non-inflamed tumors that normally do not respond to immunotherapy.

Typically, a β-catenin nucleic acid inhibitor molecule is used to reduce β-catenin expression. However, any β-catenin inhibitor or Wnt/β-catenin pathway inhibitor that reduces β-catenin expression can be used in the methods and compositions described herein, including, but not limited to small molecules, peptides, and antibodies that target β-catenin or a component of the Wnt/β-catenin pathway.

Nucleic Acid Inhibitor Molecules

In certain embodiments, β-catenin expression is reduced using a nucleic acid inhibitor molecule. Various oligonucleotide structures have been used as nucleic acid inhibitor molecules, including single stranded and double stranded oligonucleotides.

In certain embodiments, the nucleic acid inhibitor molecule is a double-stranded RNAi inhibitor molecule comprising a sense (or passenger) strand and an antisense (or guide) strand. A variety of double stranded RNAi inhibitor molecule structures are known in the art. For example, early work on RNAi inhibitor molecules focused on double-stranded nucleic acid molecules with each strand having sizes of 19-25 nucleotides with at least one 3'-overhang of 1 to 5 nucleotides (see, e.g., U.S. Pat. No. 8,372,968). Subsequently, longer double-stranded RNAi inhibitor molecules that get processed in vivo by the Dicer enzyme to active RNAi inhibitor molecules were developed (see, e.g., U.S. Pat. No. 8,883,996). Later work developed extended double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, WO 2010/033225, and WO 2016/100401, which are incorporated by reference for their disclosure of these double-stranded nucleic acid inhibitor molecules). Those structures include single-stranded extensions (on one or both sides of the molecule) and double-stranded extensions.

In some embodiments, the sense and antisense strands range from 15-66, 25-40, or 19-25 nucleotides. In some embodiments, the sense strand is less than 30 nucleotides, such as 19-24 nucleotides, such as 21 nucleotides. In some embodiments, the antisense strand is less than 30 nucleotides, such as 19-24 nucleotides, such as 21, 22, or 23 nucleotides. Typically, the duplex structure is between 15 and 50, such as between 15 and 30, such as between 18 and 26, more typically between 19 and 23, and in certain instances between 19 and 21 base pairs in length.

In some embodiments, the dsRNAi inhibitor molecule may further comprise one or more single-stranded nucleotide overhang(s). Typically, the dsRNAi inhibitor molecule has a single-stranded overhang of 1-10, 1-4, or 1-2 nucleotides. The single stranded overhang is typically located at the 3'-end of the sense strand and/or the 3'-end of the antisense strand. In certain embodiments, a single-stranded overhang of 1-10, 1-4, or 1-2 nucleotides is located at the 5'-end of the antisense strand. In certain embodiments, a single-stranded overhang of 1-10, 1-4, or 1-2 nucleotides is located at the 5'-end of the sense strand. In certain embodiments, the single-stranded overhang of 1-2 nucleotides is located at the 3'-end of the antisense strand. In certain embodiments, the dsRNA inhibitor molecule has a blunt end, typically at the 5'-end of the antisense strand.

In certain embodiments, the dsRNAi inhibitor molecule has a guide strand of 21 nucleotides in length and a passenger strand of 21 nucleotides in length, where there is a two nucleotide 3'-passenger strand overhang on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 19 base pair duplex region.

In certain embodiments, the dsRNAi inhibitor molecule has a guide strand of 23 nucleotides in length and a passenger strand of 21 nucleotides in length, where there is a blunt end on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 21 base pair duplex region.

In some embodiments, the dsRNAi inhibitor molecules include a stem and loop. Typically, a 3'-terminal region or 5'-terminal region of a passenger strand of a dsRNAi inhibitor molecule form a single stranded stem and loop structure.

In some embodiments, the dsRNAi inhibitor molecule contains a stem and a tetraloop or a triloop. In certain embodiments, the dsRNAi inhibitor molecule comprises a guide strand and a passenger strand, wherein the passenger strand contains a stem and tetraloop or triloop and ranges from 20-66 nucleotides in length. Typically, the guide and passenger strands are separate strands, each having a 5'- and 3'-end, that do not form a contiguous oligonucleotide (sometimes referred to as a "nicked" structure).

In certain of those embodiments, the guide strand is between 15 and 40 nucleotides in length. In certain embodiments, the extended part of the passenger strand that contains the stem and tetraloop or triloop is on 3'-end of the strand. In certain other embodiments, the extended part of the passenger strand that contains the stem and tetraloop or triloop is on 5'-end of the strand.

In certain embodiments, the passenger strand of a dsRNAi inhibitor molecule containing a stem and tetraloop is between 26-40 nucleotides in length and the guide strand of the dsRNAi inhibitor molecule contains between 20-24 nucleotides, wherein the passenger strand and guide strand form a duplex region of 18-24 nucleotides. In certain embodiments, the passenger strand is 26-30 nucleotides in length and the stem is 1, 2, or 3 base pairs in length and contains one or more bicyclic nucleotides.

In certain embodiments, the passenger strand of a dsRNAi inhibitor molecule containing a stem and triloop is between 27-39 nucleotides in length and the guide strand of the dsRNAi inhibitor molecule contains between 20-24 nucleotides, wherein the passenger strand and guide strand form a duplex region of 18-24 nucleotides. In certain embodiments, the passenger strand is 27-29 nucleotides in length and the stem is 2 or 3 base pairs in length and contains one or more bicyclic nucleotides.

In certain embodiments, the dsRNAi inhibitor molecule comprises (a) a passenger strand that contains a stem and tetraloop and is 36 nucleotides in length, wherein the first 20 nucleotides of the passenger strand from the 5'-end are complementary to the guide strand and the following 16 nucleotides of the passenger strand form the stem and tetraloop and (b) a guide strand that is 22 nucleotides in length and has a single-stranded overhang of two nucleotides at its 3'-end, wherein the guide and passenger strands are separate strands that do not form a contiguous oligonucleotide.

In certain embodiments, the dsRNAi inhibitor molecule comprises (a) a passenger strand that contains a stem and triloop and is 35 nucleotides in length, wherein the first 20 nucleotides of the passenger strand from the 5'-end are complementary to the guide strand and the following 16 nucleotides of the passenger strand form the stem and triloop and (b) a guide strand that is 22 nucleotides in length and has a single-stranded overhang of two nucleotides at its 3'-end, wherein the guide and passenger strands are separate strands that do not form a contiguous oligonucleotide.

In certain embodiments, the nucleic acid inhibitor molecule is a single-stranded nucleic acid inhibitor molecule. Single stranded nucleic acid inhibitor molecules are known in the art. For example, recent efforts have demonstrated activity of ssRNAi inhibitor molecules (see, e.g., Matsui et al., *Molecular Therapy,* 2016, 24(5):946-55). And, antisense molecules have been used for decades to reduce expression of specific target genes. Pelechano and Steinmetz, *Nature Review Genetics,* 2013, 14:880-93. A number of variations on the common themes of these structures have been developed for a range of targets. Single stranded nucleic acid inhibitor molecules include, for example, conventional antisense oligonucleotides, microRNA, ribozymes, aptamers, and ssRNAi inhibitor molecules, all of which are known in the art.

In certain embodiments, the nucleic acid inhibitor molecule is a ssRNAi inhibitor molecule having 14-50, 16-30, or 15-25 nucleotides. In other embodiments, the ssRNAi inhibitor molecule has 18-22 or 20-22 nucleotides. In certain embodiments, the ssRNAi inhibitor molecule has 20 nucleotides. In other embodiments, the ssRNAi inhibitor molecule has 22 nucleotides. In certain embodiments, the nucleic acid inhibitor molecule is a single-stranded oligonucleotide that inhibits exogenous RNAi inhibitor molecules or natural miRNAs.

In certain embodiments, the nucleic acid inhibitor molecule is a single-stranded antisense oligonucleotide having 8-80, 12-50, 12-30, or 12-22 nucleotides. In certain embodiments, the single-stranded antisense oligonucleotide has 16-20, 16-18, 18-22 or 18-20 nucleotides.

Modifications

Typically, multiple nucleotide subunits of the nucleic acid inhibitor molecule are modified to improve various characteristics of the molecule such as resistance to nucleases or lowered immunogenicity. See, e.g., Bramsen et al. (2009), Nucleic Acids Res., 37, 2867-2881. Many nucleotide modifications have been used in the oligonucleotide field, particularly for nucleic acid inhibitor molecules. Such modifications can be made on any part of the nucleotide, including the sugar moiety, the phosphoester linkage, and the nucleobase. In certain embodiments of the nucleic acid inhibitor molecule, from one to every nucleotide is modified at the 2'-carbon of the sugar moiety, using, for example, 2'-carbon modifications known in the art and described herein. Typical examples of 2'-carbon modifications include, but are not limited to, 2'-F, 2'-O-methyl ("2'-OMe" or "2'-OCH$_3$"), 2'-O-methoxyethyl ("2'-MOE" or "2'-OCH$_2$CH$_2$OCH$_3$"). Modifications can also occur at other parts of the sugar moiety of the nucleotide, such as the 5'-carbon, as described herein.

In certain embodiments, the ring structure of the sugar moiety is modified, including, but not limited to, Locked Nucleic Acids ("LNA") (see, e.g., Koshkin et al. (1998), *Tetrahedron,* 54, 3607-3630), bridged nucleic acids ("BNA") (see, e.g., U.S. Pat. No. 7,427,672 and Mitsuoka et al. (2009), *Nucleic Acids Res.,* 37(4):1225-38); and Unlocked Nucleic Acids ("UNA") (see, e.g., Snead et al. (2013), *Molecular Therapy—Nucleic Acids,* 2, e103 (doi: 10.1038/mtna.2013.36)).

Modified nucleobases include nucleobases other than adenine, guanine, cytosine, thymine and uracil at the 1'-position, as known in the art and as described herein. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleobase does not contain a nucleobase (abasic). A typical example of a modified nucleobase is 5'-methylcytosine.

The natural occurring internucleotide linkage of RNA and DNA is a 3' to 5' phosphodiester linkage. Modified phosphodiester linkages include non-naturally occurring internucleotide linking groups, including internucleotide linkages that contain a phosphorous atom and internucleotide linkages that do not contain a phosphorous atom, as known in the art and as described herein. Typically, the nucleic acid inhibitor molecule contains one or more phosphorous-containing internucleotide linking groups, as described herein. In other embodiments, one or more of the internucleotide linking groups of the nucleic acid inhibitor molecule is a non-phosphorus containing linkage, as described herein. In certain embodiments, the nucleic acid inhibitor molecule contains one or more phosphorous-containing internucleotide linking groups and one or more non-phosphorous containing internucleotide linking groups.

In certain embodiments, the double-stranded nucleic acid inhibitor molecule contains at least one phosphorothioate internucleotide linking group. In certain embodiments, the double-stranded nucleic acid inhibitor molecule contains less than 10, such as less than 5 phosphorothioate internucleotide linking groups. In certain embodiments, the double-stranded nucleic acid inhibitor molecule contains 4 phosphorothioate internucleotide linking groups.

The 5'-end of the nucleic acid inhibitor molecule can include a natural substituent, such as a hydroxyl or a phosphate group. In certain embodiments, a hydroxyl group is attached to the 5'-terminal end of the nucleic acid inhibitor molecule. In certain embodiments, a phosphate group is attached to the 5'-terminal end of the nucleic acid inhibitor molecule. Typically, the phosphate is added to a monomer prior to oligonucleotide synthesis. In other embodiments, 5'-phosphorylation is accomplished naturally after a nucleic acid inhibitor molecule is introduced into the cytosol, for example, by a cytosolic Clp1 kinase. In some embodiments, the 5'-terminal phosphate is a phosphate group, such as 5'-monophosphate [(HO)$_2$(O)P—O-5'], 5'-diphosphate [(HO)$_2$(O)P—O—P(HO)(O)—O-5'] or a 5'-triphosphate [(HO)$_2$(O)P—O—(HO)(O)P—O—P(HO)(O)-0-5'].

The 5'-end of the nucleic acid inhibitor molecule can also be modified. For example, in some embodiments, the 5'-end of the nucleic acid inhibitor molecule is attached to a phosphoramidate [(HO)$_2$(O)P—NH-5', (HO)(NH$_2$)(O)P—O-5']. In certain embodiments, the 5'-terminal end of the nucleic acid inhibitor molecule is attached to a phosphate mimic. Suitable phosphate mimics include 5'-phosphonates, such as 5'-methylenephosphonate (5'-MP), 5'-(E)-vinylphosphonate (5'-VP). Lima et al., Cell, 2012, 150-883-94; WO2014/130607. Other suitable phosphate mimics include 4'-phosphate analogs that are bound to the 4'-carbon of the sugar moiety (e.g., a ribose or deoxyribose or analog thereof) of the 5'-terminal nucleotide of an oligonucleotide as described in PCT International Publication No. WO 2018/045317, which is hereby incorporated by reference in its entirety. For example, in some embodiments, the 5'-end of the nucleic acid inhibitor molecule is attached to an oxymethylphosphonate, where the oxygen atom of the oxymethyl group is bound to the 4'-carbon of the sugar moiety or analog thereof. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, the nucleic acid inhibitor molecule includes one or more deoxyribonucleotides. Typically, the nucleic acid inhibitor molecules contain fewer than 5 deoxyribonucleotides. In certain embodiments, the nucleic acid inhibitor molecules include one or more ribonucleotides. In certain embodiments, all of the nucleotides of the nucleic acid inhibitor molecule are ribonucleotides.

In certain embodiments one or two nucleotides of a nucleic acid inhibitor molecule are reversibly modified with a glutathione-sensitive moiety. Typically, the glutathione-sensitive moiety is located at the 2'-carbon of the sugar moiety and comprises a sulfonyl group. In certain embodiment, the glutathione-sensitive moiety is compatible with phosphoramidite oligonucleotide synthesis methods, as described, for example, in PCT International Publication No. WO 2018/039364, which is hereby incorporated by reference in its entirety. In certain embodiments, more than two nucleotides of a nucleic acid inhibitor molecule are reversibly modified with a glutathione-sensitive moiety. In certain embodiments, most of the nucleotides are reversibly modified with a glutathione-sensitive moiety. In certain embodiments, all or substantially all the nucleotides of a nucleic acid inhibitor molecule are reversibly modified with a glutathione-sensitive moiety.

The at least one glutathione-sensitive moiety is typically located at the 5'- or 3'-terminal nucleotide of a single-stranded nucleic acid inhibitor molecule or the 5'- or 3'-terminal nucleotide of the passenger strand or the guide strand of a double-stranded nucleic acid inhibitor molecule. However, the at least one glutathione-sensitive moiety may be located at any nucleotide of interest in the nucleic acid inhibitor molecule.

In certain embodiments, a nucleic acid inhibitor molecule is fully modified, wherein every nucleotide of the sense and/or antisense strand is modified; typically every nucleotide is modified at the 2'-position of the sugar moiety. In certain embodiments, the fully modified nucleic acid inhibitor molecule does not contain a reversible modification. In some embodiments, at least one, such as at least two, three, four, five, six, seven, eight, nine, 10, 11, 12, 13, 14, 15, 16, 17, 18, 19, or 20 nucleotides of a single stranded nucleic acid inhibitor molecule or the guide strand of a double stranded nucleic acid inhibitor molecule are modified. In some embodiments, at least one, such as at least two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, or 36 nucleotides of the passenger strand of the double-stranded nucleic acid inhibitor molecule are modified.

In certain embodiments, the fully modified nucleic acid inhibitor molecule is modified with one or more reversible, glutathione-sensitive moieties. In certain embodiments, substantially all of the nucleotides of a nucleic acid inhibitor molecule are modified. In certain embodiments, more than half of the nucleotides of a nucleic acid inhibitor molecule are modified with a chemical modification other than a reversible modification. In certain embodiments, less than half of the nucleotides of a nucleic acid inhibitor molecule are modified with a chemical modification other than a reversible modification. Modifications can occur in groups on the nucleic acid inhibitor molecule or different modified nucleotides can be interspersed.

In certain embodiments of the nucleic acid inhibitor molecule, from one to every nucleotide is modified at the 2'-carbon. In certain embodiments, the nucleic acid inhibitor molecule (or the sense strand and/or antisense strand thereof) is partially or fully modified with 2'-F, 2'-O-Me, and/or 2'-MOE. In certain embodiments of the nucleic acid inhibitor molecule, from one to every phosphorous atom is modified and from one to every nucleotide is modified at the 2'-carbon of the sugar moiety.

In certain embodiments, the nucleic acid inhibitor molecule contains one or more bicyclic nucleotides. The triloop- and tetraloop-containing double-stranded nucleic acid inhibitor molecules disclosed herein contain a sense strand and an antisense strand and, in certain embodiments, may contain at least one bicyclic nucleotide in the stem portion of a stem loop structure that is present in the sense strand, as described in U.S. Provisional Application No. 62/657,428, filed 13 Apr. 2018; U.S. Provisional Application No. 62/778,755, filed 12 Dec. 2018; and U.S. Provisional Application No. 62/778,759, filed 12 Dec. 2018, each of which is hereby incorporated by reference in its entirety.

The bicyclic nucleotide comprises a bicyclic sugar moiety. In certain embodiments, the bicyclic sugar moiety comprises a first ring of 4 to 7 members and a bridge forming a North-type sugar confirmation that connects any two atoms of the first ring of the sugar moiety to form a second ring. In certain embodiments, the bridge connects the 2'-carbon and the 4'-carbon of the first ring to form a second ring.

Typically, the bridge contains 2 to 8 atoms. In certain embodiments, the bridge contains 3 atoms. In certain embodiments, the bridge contains 4 atoms. In certain embodiments, the bridge contains 5 atoms. In certain embodiments, the bridge contains 6 atoms. In certain embodiments, the bridge contains 7 atoms. In certain embodiments, the bridge contains 8 atoms. In certain embodiments, the bridge contains more than 8 atoms.

In certain embodiments, the bicyclic sugar moiety is a substituted furanosyl comprising a bridge that connects the 2'-carbon and the 4'-carbon of the furanosyl to form the second ring. In certain embodiments, the bicyclic nucleotide has the structure of Formula I

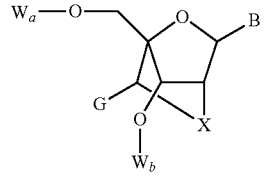

Formula I wherein B is a nucleobase;

wherein G is H, OH, NH$_2$, C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol, or substituted thio;

wherein X is O, S, or NR$_1$, wherein R$_1$ is H, C$_1$-C$_6$ alkyl, C$_1$-C$_6$ alkoxy, benzene or pyrene; and wherein W$_a$ and W$_b$ are each independently, H, OH, a hydroxyl protecting group, a phosphorous moiety, or an internucleotide linking group attaching the nucleotide represented by Formula I to another nucleotide or to an oligonucleotide and wherein at least one of W$_a$ or W$_b$ is an internucleotide linking group attaching the nucleotide represented by Formula I to an oligonucleotide.

In certain embodiments of Formula I, G is H and X is NR$_1$, wherein R$_1$ is benzene or pyrene. In certain embodiments, of Formula I, G is H and X is S.

In certain embodiments of Formula I, G is H and X is O:

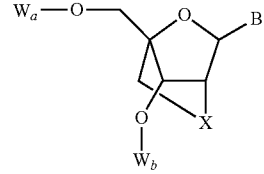

Formula Ia

In certain embodiments of Formula I, G is H and X is NR$_1$, wherein R$_1$ is H, CH$_3$, or OCH$_3$:

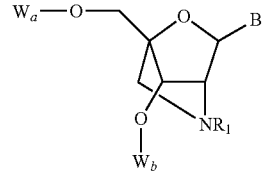

Formula Ib

In certain embodiments of Formula I, G is OH or NH$_2$ and X is O.

In certain embodiments of Formula I, G is OH and X is O:

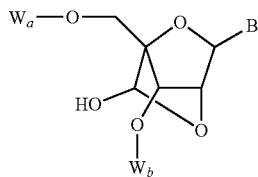

Formula Ic

In certain embodiments of Formula I, G is NH$_2$ and X is O:

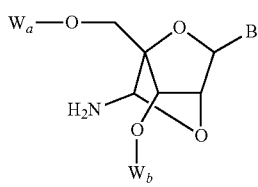

Formula Id

In certain embodiments, of Formula I, G is CH$_3$ or CH$_2$OCH$_3$ and X is O. In certain embodiments, of Formula I, G is CH$_3$ and X is O:

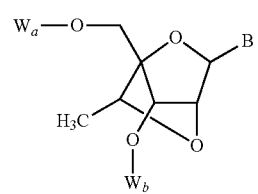

Formula Ie

In certain embodiments, of Formula I, G is CH$_2$OCH$_3$ and X is O:

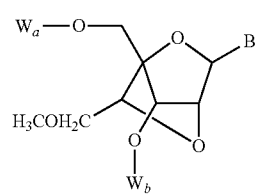

Formula If

In certain embodiments, the bicyclic nucleotide has the structure of Formula II:

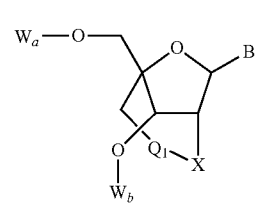

Formula II wherein B is a nucleobase;
wherein Q$_1$ is CH$_2$ or O;
wherein X is CH$_2$, O, S, or NR$_1$, wherein R$_1$ is H, C$_1$-C$_6$ alkyl, C$_1$-C$_6$ alkoxy, benzene or pyrene;
wherein if Q$_1$ is O, X is CH$_2$;
wherein if Q$_1$ is CH$_2$, X is CH$_2$, O, S, or NR$_1$, wherein R$_1$ is H, C$_1$-C$_6$ alkyl, C$_1$-C$_6$ alkoxy, benzene or pyrene;
wherein W$_a$ and W$_b$ are each independently, H, OH, a hydroxyl protecting group, a phosphorous moiety, or an internucleotide linking group attaching the nucleotide represented by Formula II to another nucleotide or to an oligonucleotide and wherein at least one of W$_a$ or W$_b$ is an internucleotide linking group attaching the nucleotide represented by Formula II to an oligonucleotide.

In certain embodiments of Formula II, Q$_1$ is O and X is C$_H$2:

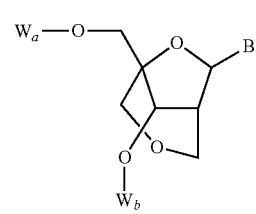

Formula IIa

In certain embodiments of Formula II, Q$_1$ is CH$_2$ and X is O:

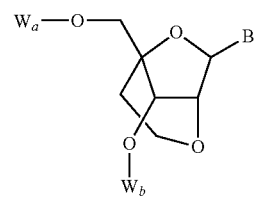

Formula IIb

In certain embodiments of Formula II, Q$_1$ is CH$_2$ and X is NR$_1$, wherein R$_1$ is H, CH$_3$ or OCH$_3$:

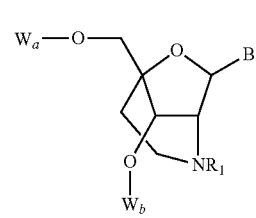

Formula IIc

In certain embodiments of Formula II, Q$_1$ is CH$_2$ and X is NH:

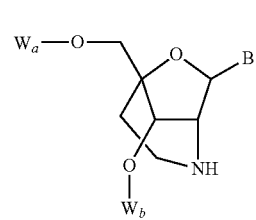

Formula IId

In certain embodiments, the bicyclic nucleotide has the structure of Formula III:

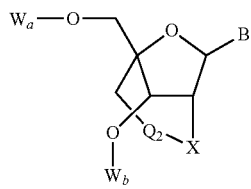

Formula III wherein B is a nucleobase;

wherein $Q_2$ is O or $NR_1$, wherein $R_1$ is H, $C_1$-$C_6$ alkyl, $C_1$-$C_6$ alkoxy, benzene or pyrene;

wherein X is $CH_2$, O, S, or $NR_1$, wherein $R_1$ is H, $C_1$-$C_6$ alkyl, $C_1$-$C_6$ alkoxy, benzene or pyrene;

wherein if $Q_2$ is O, X is $NR_1$;

wherein if $Q_2$ is $NR_1$, X is O or S;

wherein $W_a$ and $W_b$ are each independently, H, OH, a hydroxyl protecting group, a phosphorous moiety, or an internucleotide linking group attaching the nucleotide represented by Formula III to another nucleotide or to an oligonucleotide and wherein at least one of $W_a$ or $W_b$ is an internucleotide linking group attaching the nucleotide represented by Formula III to an oligonucleotide.

In certain embodiments of Formula III, $Q_2$ is O and X is $NR_1$. In certain embodiments of Formula III, $Q_2$ is O and X is $NR_1$, wherein $R_1$ is $C_1$-$C_6$ alkyl. In certain embodiments of Formula III, $Q_2$ is O and X is $NR_1$ and $R_1$ is H or $CH_3$.

In certain embodiments of Formula III, $Q_2$ is O and X is $NR_1$ and $R_1$ is $CH_3$:

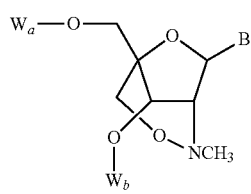

Formula IIIa

In certain embodiments of Formula III, $Q_2$ is $NR_1$ and X is O. In certain embodiments of Formula III, $Q_2$ is $NR_1$, wherein $R_1$ is $C_1$-$C_6$ alkyl and X is O.

In certain embodiments of Formula III, $Q_2$ is $NCH_3$ and X is O:

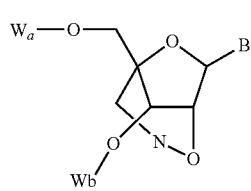

Formula IIIb

In certain embodiments, the bicyclic nucleotide has the structure of Formula IV:

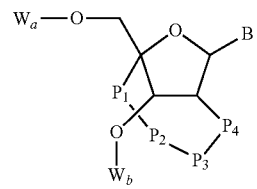

Formula IV wherein B is a nucleobase;

wherein $P_1$ and $P_3$ are $CH_2$, $P_2$ is $CH_2$ or O and $P_4$ is O; and wherein $W_a$ and $W_b$ are each independently, H, OH, a hydroxyl protecting group, a phosphorous moiety, or an internucleotide linking group attaching the nucleotide represented by Formula IV to another nucleotide or to an oligonucleotide and wherein at least one of $W_a$ or $W_b$ is an internucleotide linking group attaching the nucleotide represented by Formula IV to an oligonucleotide.

In certain embodiments of Formula IV, $P_1$, $P_2$, and $P_3$ are $CH_2$, and $P_4$ is O:

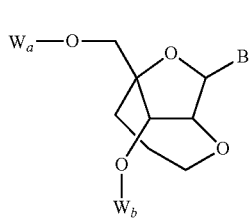

Formula IVa

In certain embodiments of Formula IV, $P_1$ and $P_3$ are $CH_2$, $P_2$ is O and $P_4$ is O:

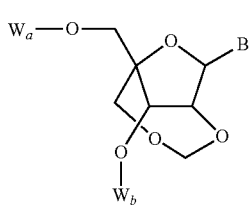

Formula IVb

In certain embodiments, the bicyclic nucleotide has the structure of Formula Va or Vb:

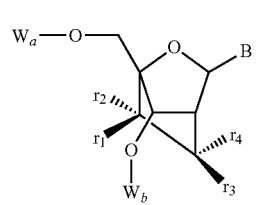

Formula Va

Formula Vb

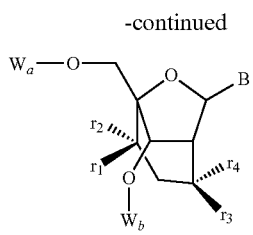

wherein B is a nucleobase;

wherein r1, r2, r3, and r4 are each independently H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl; substituted $C_2$-$C_{12}$ alkynyl; $C_1$-$C_{12}$ alkoxy; substituted $C_1$-$C_{12}$ alkoxy, $OT_1$, $ST_1$, $SOT_1$, $SO_2T_1$, $NT_1T_2$, N3, CN, C(=O)$OT_1$, C(=O)$NT_1T_2$, C(=O)$T_1$, O—C(=O)$NT_1T_2$, N(H)C(=NH)$NT_1T_2$, N(H)C(=O)$NT_1T_2$ or N(H)C(=S)$NT_1T_2$, wherein each of T1 and T2 is independently H, $C_1$-$C_6$ alkyl, or substituted $C_1$-$C_{16}$ alkyl; or r1 and r2 or r3 and r4 together are =C(r5)(r6), wherein r5 and r6 are each independently H, halogen, $C_1$-$C_{12}$ alkyl, or substituted $C_1$-$C_{12}$ alkyl; and wherein $W_a$ and $W_b$ are each independently, H, OH, a hydroxyl protecting group, a phosphorous moiety, or an internucleotide linking group attaching the nucleotide represented by Formula V to another nucleotide or to an oligonucleotide and wherein at least one of $W_a$ or $W_b$ is an internucleotide linking group attaching the nucleotide represented by Formula V to an oligonucleotide.

In certain embodiments, the bicyclic sugar moiety is a substituted furanosyl comprising a bridge that connects the 2'-carbon and the 4'-carbon of the furanosyl to form the second ring, wherein the bridge that connects the 2'-carbon and the 4'-carbon of the furanosyl includes, but is not limited to:

a) 4'-$CH_2$—O—N(R)-2' and 4'-$CH_2$—N(R)—O-2', wherein R is H, $C_1$-$C_{12}$ alkyl, or a protecting group, including, for example, 4'-$CH_2$—NH—O-2' (also known as $BNA^{NC}$) 4'-$CH_2$—N($CH_3$)—O-2' (also known as $BNA^{NC}$[NMe]), (as described in U.S. Pat. No. 7,427,672, which is hereby incorporated by reference in its entirety);

b) 4'-$CH_2$-2'; 4'-$(CH_2)_2$-2'; 4'-$(CH_2)_3$-2'; 4'-$(CH_2)$—O-2' (also known as LNA); 4'-$(CH_2)$—S-2'; 4'-$(CH_2)_2$-O-2' (also known as ENA); 4'-CH($CH_3$)—O-2' (also known as cEt); and 4'-CH($CH_2OCH_3$)—O-2' (also known as cMOE), and analogs thereof (as described in U.S. Pat. No. 7,399,845, which is hereby incorporated by reference in its entirety);

c) 4'-C($CH_3$)($CH_3$)—O-2' and analogs thereof (as described in U.S. Pat. No. 8,278,283, which is hereby incorporated by reference in its entirety);

d) 4'-$CH_2$—N($OCH_3$)-2' and analogs thereof (as described in U.S. Pat. No. 8,278,425, which is hereby incorporated by reference in its entirety);

e) 4'-$CH_2$—O—N($CH_3$)-2' and analogs thereof (as described in U.S. Patent Publication No. 2004/0171570, which is hereby incorporated by reference in its entirety);

f) 4'-$CH_2$—C(H)($CH_3$)-2' and analogs thereof (as described in Chattopadhyaya et al., *J. Org. Chem.*, 2009, 74, 118-34, which is hereby incorporated by reference in its entirety); and g) 4'-$CH_2$—C(=$CH_2$)-2' and analogs thereof as described in U.S. Pat. No. 8,278,426, which is hereby incorporated by reference in its entirety).

In certain embodiments, the bicyclic nucleotide (BN) is one or more of the following: (a) methyleneoxy BN, (b) ethyleneoxy BN, (c) aminooxy BN; (d) oxyamino BN, (e) methyl(methyleneoxy) BN (also known as constrained ethyl or cET), (f) methylene-thio BN, (g) methylene amino BN, (h) methyl carbocyclic BN, and (i) propylene carbocyclic BN, as shown below.

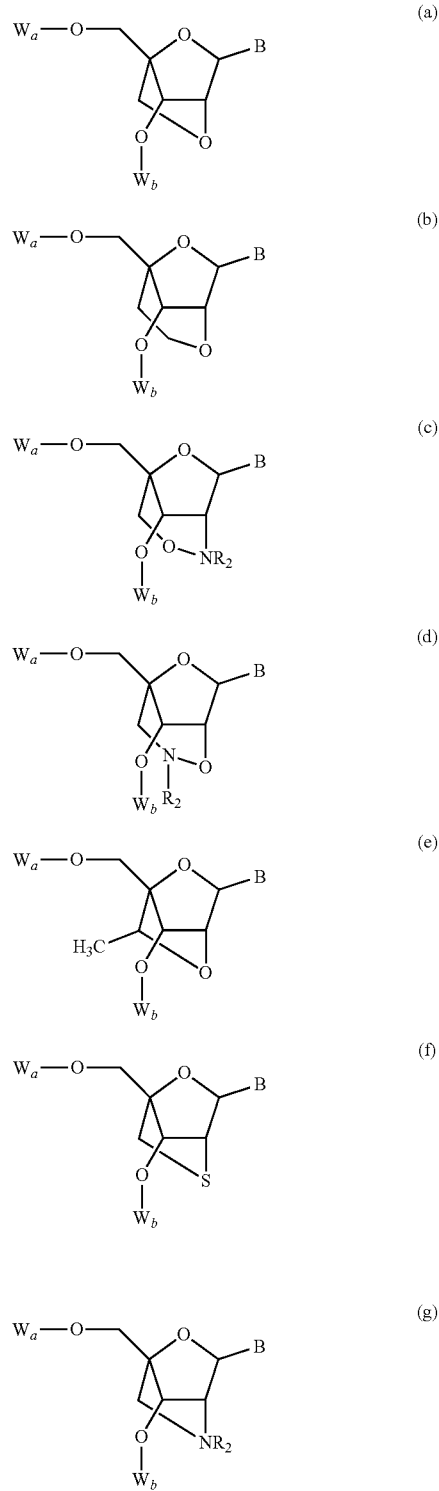

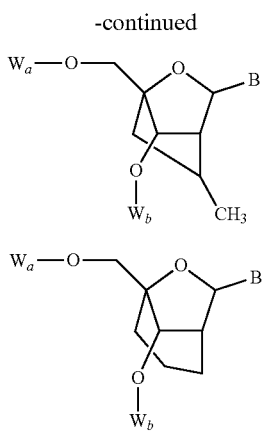

In the bicyclic nucleotides of (a) to (i) above, B is a nucleobase, R2 is H or CH$_3$ and W$_a$ and W$_b$ are each independently, H, OH, a hydroxyl protecting group, a phosphorous moiety, or an internucleotide linking group attaching the bicyclic nucleotide to another nucleotide or to an oligonucleotide and wherein at least one of W$_a$ or W$_b$ is an internucleotide linking group attaching the bicyclic nucleotide to an oligonucleotide.

In one embodiment of the oxyamino BN (d), R2 is CH$_3$, as follows (also known as BNA$^{NC}$[NMe]):

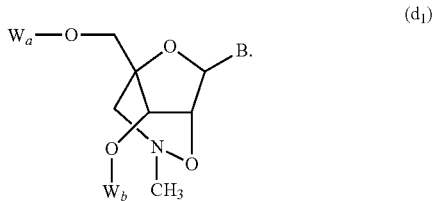

In certain embodiments, bicyclic sugar moieties and bicyclic nucleotides incorporating such bicyclic sugar moieties are further defined by isomeric configuration. In certain embodiments, the bicyclic sugar moiety or nucleotide is in the α-L configuration. In certain embodiments, the bicyclic sugar moiety or nucleotide is in the β-D configuration. For example, in certain embodiments, the bicyclic sugar moiety or nucleotide comprises a 2'O,4'-C-methylene bridge (2'-O—CH$_2$-4') in the α-L configuration (α-L LNA). In certain embodiments, the bicyclic sugar moiety or nucleotide is in the R configuration. In certain embodiments, the bicyclic sugar moiety or nucleotide is in the S configuration. For example, in certain embodiments, the bicyclic sugar moiety or nucleotide comprises a 4'-C$_H$(CH$_3$)—O-2' bridge (i.e., cEt) in the S-configuration.

β-Catenin Nucleic Acid Inhibitor

As disclosed herein, a β-catenin nucleic acid inhibitor molecule can be combined with an IDO inhibitor and immunotherapy for treating certain diseases or disorders, such as a Wnt activated cancer.

β-catenin nucleic acid inhibitor molecules are known, as disclosed, for example, in PCT International Application No. PCT/US2018/056317; U.S. Published Application Nos. 2015/0291954 and 2015/0291956; and U.S. Pat. Nos. 6,066,500; 8,198,427; 8,835,623; or 9,243,244, all of which are incorporated by reference for their disclosure of these β-catenin nucleic acid inhibitor molecules. In certain embodiments, the β-catenin nucleic acid inhibitor molecule is a molecule disclosed in U.S. Pat. No. 9,243,244. In certain embodiments, the β-catenin nucleic acid inhibitor molecule is a molecule disclosed in PCT International Application No. PCT/US2018/056317, which is hereby incorporated by reference in its entirety.

In certain embodiments, the β-catenin nucleic acid inhibitor molecules of the invention are dsRNAi inhibitor molecules where the double-stranded region of the molecule is between 15-40 nucleotides in length. In certain of those embodiments, the double-stranded region is between 19-30, 19-23, or 19-21 nucleotides in length. In certain of those embodiments, the double-stranded region is 19, 20, 21, 22, 23, 24, 25, or 26 nucleotides in length.

In certain embodiments, the β-catenin nucleic acid inhibitor molecules of the invention are dsRNAi inhibitor molecules where the sense strand is between 18 and 66 nucleotides in length. In certain embodiments, the sense strand is between 18 and 25 nucleotides in length. In certain embodiments, the sense strand is 18, 19, 20, 21, 22, 23, or 24 nucleotides in length. In certain of those embodiments, the sense strand is between 25 and 45 nucleotides in length. In certain of those embodiments, the sense strand is between 26 and 30 nucleotides in length. In certain of those embodiments, the sense strand is between 27 and 29 nucleotides in length. In certain embodiments, the sense strand is between 30 and 40 nucleotides in length. In certain embodiments, the sense strand is 36, 37, 38, 39, or 40 nucleotides in length. In certain embodiments, the sense strand is between 25 and 30 nucleotides in length. In certain of those embodiments, the sense strand is 25, 26, or 27 nucleotides in length.

In certain embodiments, the β-catenin nucleic acid inhibitor molecules are dsRNAi inhibitor molecules where the antisense strand is between 18 and 66 nucleotides in length. Typically, the antisense strand comprises a sequence that is sufficiently complementary to a sequence in the target gene mRNA to direct the effect of the nucleic acid inhibitor molecule to the target gene. In certain embodiments, the antisense strand comprises a sequence that is fully complementary with a sequence contained in the target gene mRNA where the fully complementary sequence is between 18 and 40 nucleotides long. In certain of those embodiments, the antisense strand is between 20 and 50 nucleotides in length. In certain embodiments, the antisense strand is between 20 and 30 nucleotides in length. In certain embodiments, the antisense strand is 21, 22, 23, 24, 25, 26, 27, or 28 nucleotides in length. In certain embodiments, the antisense strand is between 35 and 40 nucleotides in length. In certain of those embodiments, the antisense strand is 36, 37, 38, or 39 nucleotides in length.

In certain embodiments, the β-catenin nucleic acid inhibitor molecule is a dsRNAi inhibitor molecule comprising a sense and an antisense strand and a duplex region of between 18-34 nucleotides, wherein the sense strand is 25-34 nucleotides in length and the antisense strand is 26-38 nucleotides in length and comprises 1-5 single-stranded nucleotides at its 3'-terminus. In certain embodiments, the sense strand is 26 nucleotides, the antisense strand is 38 nucleotides and has a single-stranded overhang of 2 nucleotides at its 3'-terminus and a single-stranded overhang of 10 nucleotides at its 5'-terminus, and the sense strand and antisense strand form a duplex region of 26 nucleotides. In certain embodiments, the sense strand is 25 nucleotides, the antisense strand is 27 nucleotides and has a single-stranded overhang of 2 nucleotides at its 3'-terminus, and the sense strand and antisense strand form a duplex region of 25 nucleotides.

In certain embodiments, the β-catenin nucleic acid inhibitor molecule is a dsRNAi inhibitor molecule comprising a sense and an antisense strand and a duplex region of between 19-21 nucleotides, wherein the sense strand is 19-21 nucleotides in length and the antisense strand is 21-23 nucleotides in length and comprises a single-stranded overhang of 1-2 nucleotides at its 3'-terminus. In certain embodiments, the sense strand is 21 nucleotides and has a single-stranded overhang of 2 nucleotides at its 3'-end, the antisense strand is 21 nucleotides and has a single-stranded overhang of 2 nucleotides at its 3'-end, and sense strand and antisense strand form a duplex region of 19 nucleotides. In certain embodiments, the sense strand is 21 nucleotides, the antisense strand is 23 nucleotides and has a single-stranded overhang of 2 nucleotides at its 3'-end, and sense strand and antisense strand form a duplex region of 21 nucleotides.

In some embodiments, the β-catenin nucleic acid inhibitor molecule is a dsRNAi inhibitor molecule comprising a stem and tetraloop or triloop. In certain embodiments, the sense strand of the dsRNAi inhibitor molecule contains the stem and tetraloop and is between 34-40, 26-36, 26-30, or 34-36 nucleotides in length and the antisense strand of the dsRNAi inhibitor molecule contains between 20-24 nucleotides, wherein the sense strand and antisense strand form a duplex region of 18-24 nucleotides. In certain embodiments, the sense strand of the dsRNAi inhibitor molecule contains the stem and triloop and is between 33-39, 27-29, or 33-35 nucleotides in length and the antisense strand of the dsRNAi inhibitor molecule contains between 20-24 nucleotides, wherein the sense strand and antisense strand form a duplex region of 18-24 nucleotides.

In certain embodiments, the dsRNAi inhibitor molecule comprises (a) a sense strand that contains a stem and tetraloop and is 36 nucleotides in length, wherein the first 20 nucleotides of the sense strand from the 5'-end are complementary to the antisense strand and the following 16 nucleotides of the sense strand form the stem and tetraloop and (b) an antisense strand that is 22 nucleotides in length and has a single-stranded overhang of two nucleotides at its 3'-end, wherein the antisense and sense strands are separate strands that do not form a contiguous oligonucleotide. In certain embodiments, the sense strand contains a stem and tetraloop and is 26, 28, or 30 nucleotides in length, and the stem contains one or more bicyclic nucleotides and is 1, 2 or 3 base pairs in length.

In certain embodiments, the dsRNAi inhibitor molecule comprises (a) a sense strand that contains a stem and triloop and is 35 nucleotides in length, wherein the first 20 nucleotides of the sense strand from the 5'-end are complementary to the antisense strand and the following 15 nucleotides of the sense strand form the stem and triloop and (b) an antisense strand that is 22 nucleotides in length and has a single-stranded overhang of two nucleotides at its 3'-end, wherein the antisense and sense strands are separate strands that do not form a contiguous oligonucleotide. In certain embodiments, the sense strand contains a stem and triloop and is 27 or 29 nucleotides in length, and the stem contains one or more bicyclic nucleotides and is 2 or 3 base pairs in length.

In certain embodiments, the β-catenin nucleic acid inhibitor molecule is a conventional antisense oligonucleotide that has a sequence in the 5' to 3' direction that comprises the reverse complement of a segment of a target nucleic acid (e.g., β-catenin). In certain embodiments, the antisense oligonucleotide comprises 12-30, 12-25, 12-22, 14-20, 16-20, or 18-22 nucleotides. In certain embodiments, the antisense oligonucleotide comprises 16-18 nucleotides. In certain embodiments, the antisense oligonucleotide comprises 18-20 nucleotides. In other embodiment, the antisense oligonucleotide has 8-80 or 12-50 nucleotides. In certain embodiments, the antisense oligonucleotide or a portion thereof is fully complementary to a target nucleic acid (e.g., β-catenin) or a specific portion thereof. In certain embodiments, the antisense oligonucleotide or a portion thereof is complementary to at least 12, 13, 14, 15, 16, 17, 18, 19, 20, or more contiguous nucleotides of the target nucleic acid (e.g., β-catenin). In certain embodiments, the antisense oligonucleotide contains no more than 5, 4, 3, 2, or 1 non-complementary nucleotides relative to the target nucleic acid (e.g., β-catenin) or portion thereof. It is possible to decrease the length of the antisense oligonucleotide and/or introduce mismatch bases without eliminating activity.

In certain embodiments, the β-catenin nucleic acid inhibitor molecules of the invention are ssRNAi inhibitor molecules.

In certain embodiments, the antisense strand of the β-catenin nucleic acid inhibitor molecule comprises the sequence of SEQ ID NO: 2. In certain embodiments, the antisense strand of the β-catenin nucleic acid inhibitor molecule consists of the sequence of SEQ ID NO: 2. In certain embodiments, the β-catenin nucleic acid inhibitor molecule is a dsRNAi inhibitor molecule and the sense strand comprises the sequence of SEQ ID NO: 1. In certain embodiments, the β-catenin nucleic acid inhibitor molecule is a dsRNAi inhibitor molecule and the sense strand consists of the sequence of SEQ ID NO: 1. In certain embodiments, the β-catenin nucleic acid inhibitor molecule is a dsRNAi inhibitor molecule and the sense strand comprises the sequence of SEQ ID NO: 1 and the antisense strand comprises the sequence of SEQ ID NO: 2. In certain embodiments, the β-catenin nucleic acid inhibitor molecule is a dsRNAi inhibitor molecule where the sense strand consists of the sequence of SEQ ID NO: 1 and the antisense strand consists of the sequence of SEQ ID NO: 2.

The level or activity of a β-catenin RNA can be determined by a suitable method now known in the art or that is later developed. It can be appreciated that the method used to measure a target RNA and/or the "expression" of a target gene can depend upon the nature of the target gene and its encoded RNA. For example, where the target β-catenin RNA sequence encodes a protein, the term "expression" can refer to a protein or the β-catenin RNA/transcript derived from the β-catenin gene (either genomic or of exogenous origin). In such instances the expression of the target β-catenin RNA can be determined by measuring the amount of β-catenin RNA/transcript directly or by measuring the amount of β-catenin protein. Protein can be measured in protein assays such as by staining or immunoblotting or, if the protein catalyzes a reaction that can be measured, by measuring reaction rates. All such methods are known in the art and can be used. Where target β-catenin RNA levels are to be measured, art-recognized methods for detecting RNA levels can be used (e.g., RT-PCR, Northern Blotting, etc.). In targeting β-catenin RNAs, measurement of the efficacy of the nucleic acid inhibitor molecule in reducing levels of β-catenin RNA or protein in a subject, tissue, in cells, either in vitro or in vivo, or in cell extracts can also be used to determine the extent of reduction of β-catenin-associated phenotypes (e.g., disease or disorders, e.g., cancer or tumor formation, growth, metastasis, spread, etc.), as disclosed, for example, in International Application No. PCT/US2017/022510, which is published as WO/2017/160983. The above measurements can be made on cells, cell extracts, tissues, tissue extracts or other suitable source material.

IDO Inhibitors

Indoleamine 2,3-dioxygenase (IDO) is an intracellular enzyme with two isoforms, IDO1 and IDO2, that is involved in the metabolic pathway that converts the essential amino acid tryptophan to kynurenine. IDO1 is expressed in many human cancers and overexpression of IDO1 is associated with advanced stages of cancer and cancer metastasis in a variety of tumor types. Munn, Front. Biosci., 2012, (Elite Ed.) 4:734-45. IDO1 overexpression is also associated with an immunosuppressive tumor microenvironment that reduces T cell infiltration, resulting in non-inflamed or cold tumors that are resistant to immunotherapy. IDO2 is overexpressed in certain solid tumors and has also been implicated in immunomodulation, as has tryptophan 2,3-dioxygenase (TDO), which is another tryptophan catabolic enzyme, like IDO1 and IDO2. Pendergast et al., Cancer Research, 2017, 77(24):6795-6811. Thus, inhibiting TDO, like inhibiting IDO, provides another immunomodulatory strategy that can be used in combination with β-catenin and IDO inhibition to enhance anti-tumor activity.

In recent years, the IDO pathway has emerged as a leading target for the development of new anti-cancer drugs. Therefore, a number of IDO inhibitors are known in the art, including, for example, those disclosed in U.S. Pat. Nos. 9,850,249; 9,789,094; 9,790,169; 9,771,370; 9,765,018; 9,758,492; 9,675,571; 9,624,188; 9,617,272; 9,598,422; 9,499,497; 9,174,942; 9,073,875; 8,951,536; 8,846,726; and 8,748,469; U.S. Published Application Nos. 2006/0258719 and 2007/0185165, and PCT International Publication No. WO2004/094409, and Pendergast et al., Cancer Research, 2017, 77(24):6795-6811, all of which are incorporated by reference in their entireties.

Any IDO inhibitor can be used in the methods and compositions disclosed in this application, including those known in the art. In certain embodiments, the IDO inhibitor includes, but is not limited to, epacadostat (INCB24360), indoximod (NLG8189, aka 1-methyl-D-tryptophan), BMS-986205, NLG802, HTI-1090, navoximod (NLG919), PF-06840003, IOM2983, RG-70099, a phenyl benzenesulfonylhydrazide (see e.g., Cheng et al., Bioorg Med Chem Lett, 2014, 24:3403-06), β-(3-benzofuranyl)-alanine, β-[3-benzo(b)thienyl]-alanine, and 6-nitro-D-tryptophan.

In certain embodiments, the IDO inhibitor is epacadostat. In certain embodiments, the IDO inhibitor is indoximod. In certain embodiments, the IDO inhibitor is BMS-986205. In certain embodiments, the IDO inhibitor is NLG802. In certain embodiments, the IDO inhibitor is HTI-1090. In certain embodiments, the IDO inhibitor is navoximod. In certain embodiments, the IDO inhibitor is PF-06840003. In certain embodiments, the IDO inhibitor is IOM2983. In certain embodiments, the IDO inhibitor is RG-70099. In certain embodiments, the IDO inhibitor is a phenyl benzenesulfonylhydrazide.

Typically, the IDO inhibitor selectively inhibits IDO1. For example, epacadostat, BMS-986205, PF-06840003, and IOM2983 selectively target IDO1. In other embodiments, the IDO inhibitor inhibits IDO2. For example, indoximod has been reported to indirectly inhibit IDO2. Pendergast et al., *Cancer Research*, 2017, 77(24):6795-6811. In certain embodiments, the IDO inhibitor inhibits IDO1 and one or more of IDO2 and/or TDO. Navoximod, for example, inhibits both IDO1 and TDO, although it is about 20-fold more selective for IDO1 than TDO. Pendergast et al., Cancer Research, 2017, 77(24):6795-6811. In other embodiments of the methods and compositions disclosed herein, the IDO inhibitor is replaced by a TDO inhibitor.

Immunotherapy

The methods and compositions disclosed herein relate to combination therapy with a β-catenin inhibitor, an IDO inhibitor, and immunotherapy (or an immunotherapeutic agent). Immunotherapy refers to methods of enhancing an immune response. Typically, in the methods disclosed herein an anti-tumor immune response is enhanced. In certain embodiments, immunotherapy refers to methods of enhancing a T cell response against a tumor or cancer.

In certain embodiments, the immunotherapy or immunotherapeutic agent targets an immune checkpoint molecule. Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain embodiments, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory immune checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain embodiments, the inhibitory immune checkpoint molecule is CTLA4 or PD-1. In other embodiments, the inhibitory immune checkpoint molecule is a ligand for PD-1, such as PD-L1 or PD-L2. In other embodiments, the inhibitory immune checkpoint molecule is a ligand for CTLA4, such as CD80 or CD86. In other embodiments, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine A2a receptor (A2aR).

Antagonists that target these inhibitory immune checkpoint molecules can be used to enhance antigen-specific T cell responses against certain cancers. Accordingly, in certain embodiments, the immunotherapy or immunotherapeutic agent is an antagonist of an inhibitory immune checkpoint molecule. In certain embodiments, the inhibitory immune checkpoint molecule is PD-1. In certain embodiments, the inhibitory immune checkpoint molecule is PD-L1. In certain embodiments, the antagonist of the inhibitory immune checkpoint molecule is an antibody and preferably is a monoclonal antibody. In certain embodiments, the antibody or monoclonal antibody is an anti-CTLA4, anti-PD-1, anti-PD-L1, or anti-PD-L2 antibody. In certain embodiments, the antibody is a monoclonal anti-PD-1 antibody. In certain embodiments, the antibody is a monoclonal anti-PD-L1 antibody. In certain embodiments, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain embodiments, the anti-PD-1 antibody is one or more of pembrolizumab (Keytruda®) or nivolumab (Opdivo®). In certain embodiments, the anti-CTLA4 antibody is ipilimumab (Yervoy®). In certain embodiments, the anti-PD-L1 antibody is one or more of atezolizumab (Tecentriq®), avelumab (Bavencio®), or durvalumab (Imfinzi®).

In certain embodiments, the immunotherapy or immunotherapeutic agent is an antagonist (e.g. antibody) against CD80, CD86, LAG3, KIR, TIM3, GAL9, or A2aR. In other embodiments, the antagonist is a soluble version of the inhibitory immune checkpoint molecule, such as a soluble fusion protein comprising the extracellular domain of the inhibitory immune checkpoint molecule and an Fc domain of an antibody. In certain embodiments, the soluble fusion protein comprises the extracellular domain of CTLA4, PD-1, PD-L1, or PD-L2. In certain embodiments, the soluble fusion protein comprises the extracellular domain of CD80, CD86, LAG3, KIR, TIM3, GAL9, or A2aR. In one embodiment, the soluble fusion protein comprises the extracellular domain of PD-L2 or LAG3.

In certain embodiments, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain embodiments, the immune checkpoint molecule is a co-stimulatory molecule selected from CD28, inducible T cell co-stimulator (ICOS), CD137, OX40, or CD27. In other embodiments, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain embodiments, the immunotherapy or immunotherapeutic agent is an agonist of a co-stimulatory checkpoint molecule. In certain embodiments, the agonist of the co-stimulatory checkpoint molecule is an agonist antibody and preferably is a monoclonal antibody. In certain embodiments, the agonist antibody or monoclonal antibody is an anti-CD28 antibody. In other embodiments, the agonist antibody or monoclonal antibody is an anti-ICOS, anti-CD137, anti-OX40, or anti-CD27 antibody. In other embodiments, the agonist antibody or monoclonal antibody is an anti-CD80, anti-CD86, anti-B7RP1, anti-B7-H3, anti-B7-H4, anti-CD137L, anti-OX40L, or anti-CD70 antibody.

Pharmaceutical Compositions

The present disclosure provides pharmaceutical compositions comprising a therapeutically effective amount of a β-catenin nucleic acid inhibitor molecule and a pharmaceutically acceptable excipient. Typically, the β-catenin nucleic acid inhibitor molecule is not included in the same pharmaceutical composition as the IDO inhibitor or the immunotherapeutic agent. However, in certain embodiments, the pharmaceutical composition comprising the β-catenin nucleic acid inhibitor molecule and the pharmaceutically acceptable excipient further comprises a therapeutically effective amount of an IDO inhibitor (e.g., one or more of epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan), and/or a therapeutically effective amount of an immunotherapeutic agent, such as an antagonist of an inhibitory immune checkpoint molecule (e.g., one or more of an anti-CTLA-4, anti-PD-1, or anti-PD-L1 antibody) or an agonist of a co-stimulatory checkpoint molecule.

These pharmaceutical compositions may be sterilized by conventional sterilization techniques, or may be sterile filtered. The resulting aqueous solutions may be packaged for use as is, or lyophilized, the lyophilized preparation being combined with a sterile aqueous excipient prior to administration. The pH of the preparations typically will be between 3 and 11, more preferably between 5 and 9 or between 6 and 8, and most preferably between 7 and 8, such as 7 to 7.5.

The pharmaceutical compositions of the present disclosure are applied for therapeutic use. Thus, one aspect of the disclosure provides a pharmaceutical composition, which may be used to treat a subject including, but not limited to, a human suffering from a disease or condition by administering to said subject a therapeutically effective amount of a pharmaceutical composition of the present disclosure. Typically, the disease or condition is cancer, as described herein.

In certain embodiments, the present disclosure features the use of a therapeutically effective amount of a pharmaceutical composition as described herein for the manufacture of a medicament for treatment of a subject in need thereof. Typically, the subject has cancer, as described herein.

Pharmaceutically-Acceptable Excipients

Typically, the pharmaceutically-acceptable excipients useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; malt; gelatin; excipients, such as cocoa butter and suppository waxes; oils, such as peanut oil, cottonseed oil, safflower oil, sesame oil, olive oil, corn oil and soybean oil; buffering agents, such as magnesium hydroxide and aluminum hydroxide; (isotonic saline; Ringer's solution); ethyl alcohol; pH buffered solutions; polyols, such as glycerol, propylene glycol, polyethylene glycol, and the like; and other non-toxic compatible substances employed in pharmaceutical formulations.

Dosage Forms

The pharmaceutical compositions may be formulated with conventional excipients for any intended route of administration.

Typically, the pharmaceutical compositions of the present disclosure that contain nucleic acid inhibitor molecules are formulated in liquid form for parenteral administration, for example, by subcutaneous, intramuscular, intravenous or epidural injection.

Typically, the pharmaceutical compositions of the present disclosure that contain an immunotherapeutic agent, such as an antagonist of an inhibitory immune checkpoint molecule (e.g., one or more of an anti-CTLA-4, anti-PD-1, or anti-PD-L1 antibody) or an agonist of a co-stimulatory checkpoint molecule, are formulated in liquid form for parenteral administration, for example, by subcutaneous, intramuscular, intravenous or epidural injection.

Typically, the pharmaceutical compositions of the present disclosure that contain an IDO inhibitor, such as epacadostat, indoximod, or BMS-986205, are formulated for enteral administration, including, for example, oral administration.

Dosage forms suitable for parenteral administration typically include one or more suitable vehicles for parenteral administration including, by way of example, sterile aqueous solutions, saline, low molecular weight alcohols such as propylene glycol, polyethylene glycol, vegetable oils, gelatin, fatty acid esters such as ethyl oleate, and the like. The parenteral formulations may contain sugars, alcohols, antioxidants, buffers, bacteriostats, solutes which render the formulation isotonic with the blood of the intended recipient or suspending or thickening agents. Proper fluidity can be maintained, for example, by the use of surfactants. Liquid formulations can be lyophilized and stored for later use upon reconstitution with a sterile injectable solution.

The pharmaceutical compositions may also be formulated for other routes of administration including topical or transdermal administration, rectal or vaginal administration, ocular administration, nasal administration, buccal administration, or sublingual administration.

Delivery Agents

The β-catenin nucleic acid inhibitor molecule may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the β-catenin nucleic acid inhibitor molecule is formulated in a lipid nanoparticle (LNP). Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as LIPEX® Extruder (Northern Lipids, Inc). To prepare a lipid nanoparticle for therapeutic use, it may desirable to remove solvent (e.g., ethanol) used to form the nanoparticle and/or exchange buffer, which can be accomplished by, for example, dialysis or tangential flow filtration. Methods of making lipid nanoparticles containing nucleic acid interference molecules are known in the art, as disclosed, for example in U.S. Published Patent Application Nos. 2015/0374842 and 2014/0107178.

In certain embodiments, the LNP comprises a core lipid component comprising a cationic liposome and a pegylated lipid. The LNP can further comprise one or more envelope lipids, such as a cationic lipid, a structural or neutral lipid, a sterol, a pegylated lipid, or mixtures thereof.

Figure 13:
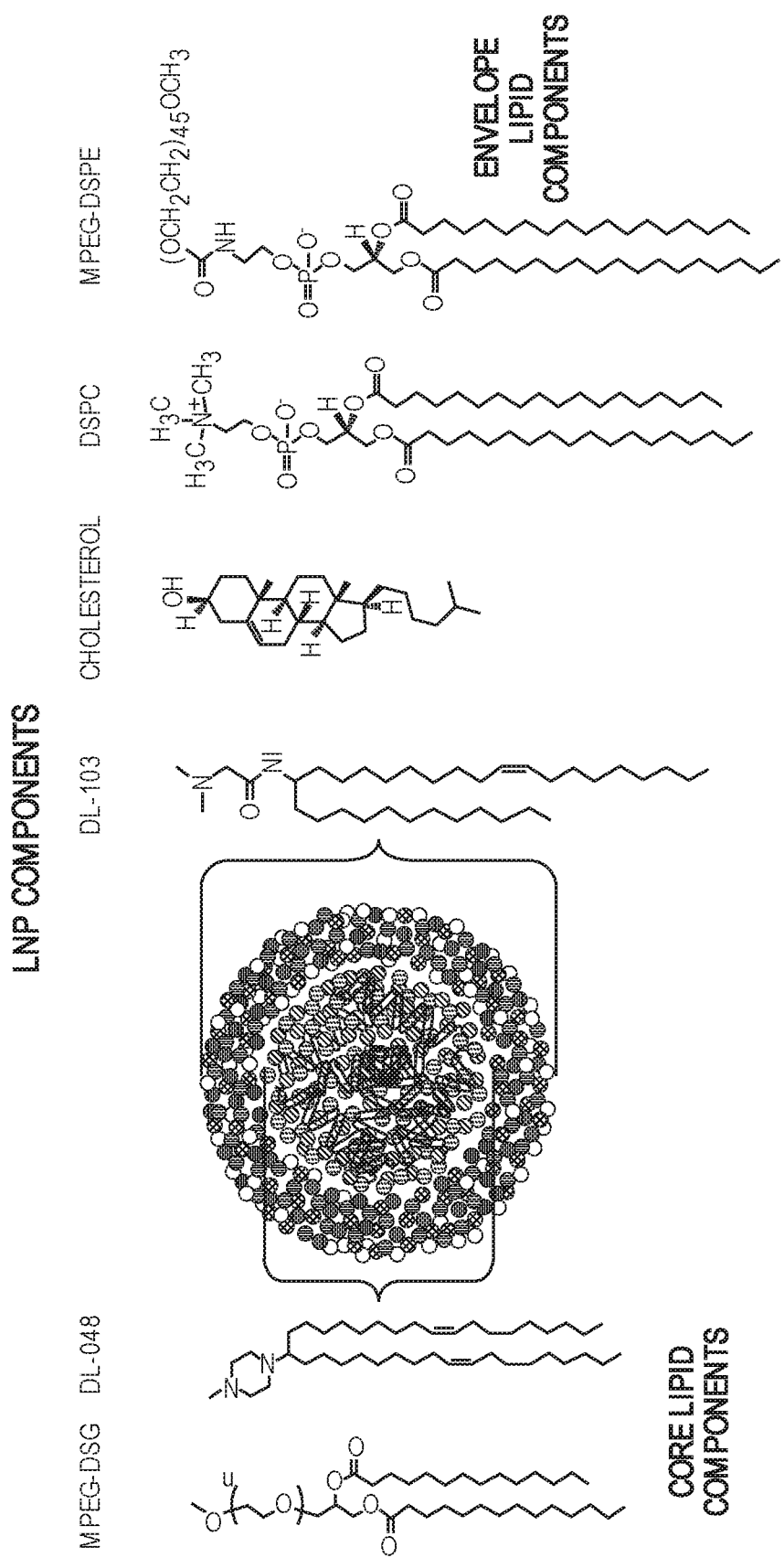
FIG. 13 shows one non-limiting embodiment of a lipid nanoparticle (LNP) that can be used to formulate the β-catenin nucleic acid inhibitor molecule. The LNP includes the following core lipids: DL-048 (cationic lipid) and DSG-MPEG (pegylated lipid), and the following envelope lipids: DL-103 (cationic lipid), DSPC, cholesterol, and DSPE-MPEG (pegylated lipid).

Cationic lipids for use in LNPs are known in the art, as discussed for example in U.S. Published Patent Application Nos. 2015/0374842 and 2014/0107178. Typically, the cationic lipid is a lipid having a net positive charge at physiological pH. In certain embodiments, the cationic liposome is DODMA, DOTMA, DL-048, or DL-103. In certain embodiments the structural lipid is DSPC, DPPC or DOPC. In certain embodiments, the sterol is cholesterol. In certain embodiments, the pegylated lipid is DMPE-PEG, DSPE-PEG, DSG-PEG, DMPE-PEG2K, DSPE-PEG2K, DSG-PEG2K, or DSG-MPEG. In one embodiment, the cationic lipid is DL-048, the pegylated lipid is DSG-MPEG and the one or more envelope lipids are DL-103, DSPC, cholesterol, and DSPE-MPEG. See e.g., FIG. 13, showing one non-limiting embodiment of a LNP that can used to formulate the β-catenin nucleic acid inhibitor molecule.

In certain embodiments, the β-catenin nucleic acid inhibitor molecule is covalently conjugated to a ligand that directs delivery of the oligonucleotide to a tissue of interest. Many such ligands have been explored. See, e.g., Winkler, Ther. Deliv. 4(7): 791-809 (2013). For example, the β-catenin nucleic acid inhibitor molecule can be conjugated to one or more sugar ligand moieties (e.g., N-acetylgalactosamine (GaNAc)) to direct uptake of the oligonucleotide into the liver. See, e.g., WO 2016/100401. Typically, the β-catenin nucleic acid inhibitor molecule is conjugated to three or four sugar ligand moieties. Other ligands that can be used include, but are not limited to, mannose-6-phosphate, cholesterol, folate, transferrin, and galactose (for other specific exemplary ligands see, e.g., WO 2012/089352). Typically, when an oligonucleotide is conjugated to a ligand, the oligonucleotide is administered as a naked oligonucleotide, wherein the oligonucleotide is not also formulated in an LNP or other protective coating. In certain embodiments, each nucleotide within the naked oligonucleotide is modified at the 2'-position of the sugar moiety, typically with 2'-F, 2'-OMe, and/or 2'-MOE.

Methods of Administration/Treatment

The pharmaceutical compositions described herein that contain a β-catenin nucleic acid inhibitor molecule or an immunotherapeutic agent are typically administered parenterally. Pharmaceutical compositions containing the β-catenin nucleic acid inhibitor molecule are typically administered intravenously or subcutaneously. Pharmaceutical compositions containing the immunotherapeutic agent are typically administered intravenously. Pharmaceutical compositions containing an IDO inhibitor, such as epacadostat, indoximod, or BMS-986205, are typically administered orally. However, the pharmaceutical compositions disclosed herein may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the pharmaceutical compositions disclosed herein may be useful for the treatment or prevention of symptoms related to a Wnt activated disease or disorder, such as cancer. In other embodiments, the pharmaceutical compositions disclosed herein may be useful for the treatment or prevention of symptoms related to a non-Wnt activated disease or disorder, such as cancer.

One embodiment is directed to a method of treating cancer, comprising administering to a subject a first pharmaceutical composition comprising a therapeutically effective amount of a β-catenin nucleic acid inhibitor molecule, a second pharmaceutical composition comprising a therapeutically effective amount of an IDO inhibitor, and a third pharmaceutical composition comprising a therapeutically effective amount of an immunotherapeutic agent. In some embodiments, the β-catenin nucleic acid inhibitor molecule is an RNAi inhibitor molecule, including a ssRNAi inhibitor molecule or a dsRNAi inhibitor molecule. In some embodiments, the IDO inhibitor is one or more of epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo (b)thienyl]-alanine, or 6-nitro-D-tryptophan. In one embodiment, the IDO inhibitor is epacadostat. In some embodiments, the immunotherapeutic agent is as an antagonist of an inhibitory immune checkpoint molecule or an agonist of a co-stimulatory checkpoint molecule. In certain embodiments, the antagonist of an inhibitory immune checkpoint molecule is an anti-CTLA-4, anti-PD-1, anti-PD-L1 antibody, or a combination of thereof.

Another embodiment is directed to a method of treating cancer, comprising administering to a subject a first pharmaceutical composition comprising a therapeutically effective amount of a β-catenin nucleic acid inhibitor molecule and a second pharmaceutical composition comprising a therapeutically effective amount of an IDO inhibitor. In some embodiments, the β-catenin nucleic acid inhibitor molecule is an RNAi inhibitor molecule, including a ssRNAi inhibitor molecule or a dsRNAi inhibitor molecule. In some embodiments, the IDO inhibitor is one or more of epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan. In one embodiment, the IDO inhibitor is epacadostat.

Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. In certain embodiments, the present disclosure features methods of treating liver cancer, liver carcinoma, hepatoma, hepatocellular carcinoma, cholangiocarcinoma and hepatoblastoma. In certain embodiments of the treatment methods, the cancer is colorectal cancer, hepatocellular carcinoma, or melanoma.

In certain embodiments of the treatment methods, prior to the administration of the β-catenin nucleic acid inhibitor molecule and IDO inhibitor, the cancer is not responsive to immunotherapy, such as an antagonist of an inhibitory immune checkpoint molecule (e.g., one or more of an anti-CTLA-4, anti-PD-1, or anti-PD-L1 antibody) or an agonist of a co-stimulatory checkpoint molecule, such as an anti-CD28 antibody.

In certain embodiments of the treatment methods, the cancer is a metastatic cancer. In certain embodiments of the treatment methods, the cancer is melanoma. In certain embodiments, the melanoma is Stage III or Stage IV melanoma. In certain embodiments, the cancer is non-small cell lung cancer. In certain embodiments, the cancer is bladder cancer. In certain embodiments, the cancer is metastatic or recurrent squamous cell carcinoma of the head and neck. In certain embodiments, the cancer is advanced urothelial cell carcinoma. In certain embodiments, the cancer is metastatic pancreatic cancer. In certain embodiments, the cancer is an advanced solid tumor.

In some embodiments, the cancer is associated with an activated Wnt/β-catenin pathway. In other embodiments, the cancer is a non-Wnt activated cancer. In certain embodiments, the cancer overexpresses IDO1. In certain embodiments, the subject has been identified as having a Wnt activated cancer or overexpression of IDO before administering the 0-catenin nucleic acid inhibitor molecule. The subject may be identified as having a Wnt activated cancer or overexpression of IDO using any method available to the skilled artisan. Typically, however, a sample from the subject is analyzed to determine if the subject has a Wnt activated cancer or overexpression of IDO. In certain embodiments, the sample comprises tissue, cells, blood, or urine. In certain embodiments, the sample is analyzed for one or more biomarkers associated with an activated Wnt/β-catenin pathway, an inactive Wnt/β-catenin pathway and/or a non-T cell inflamed phenotype. Any appropriate biomarker can be analyzed, including, but not limited to nucleic acids (e.g., mRNA), proteins, and peptides using any suitable assay or technique. In certain embodiments, the biomarker is a gene mutation that is associated with an activated Wnt/β-catenin pathway, such as a mutation in a gene encoding β-catenin or APC or one or more other components involved in the Wnt/β-catenin pathway, such as, Axin, LEF, and ICAT.

In certain embodiments, the Wnt activated cancer is resistant to immunotherapy, but the resistance to immunotherapy can be reversed by administering the immunotherapy in combination with the β-catenin nucleic acid inhibitor molecule and the IDO inhibitor.

In some embodiments, the present disclosure provides a method of potentiating an in vivo immune response against a cancer, comprising administering to a subject having cancer a β-catenin nucleic acid inhibitor molecule and an IDO inhibitor in an amount sufficient to potentiate the therapeutic effect of immunotherapy against the cancer or otherwise render the cancer susceptible to the immunotherapy. Typically, prior to administering the β-catenin nucleic acid inhibitor molecule and IDO inhibitor, the cancer is associated with a non-T cell inflamed phenotype that is resistant to immunotherapy and administering the β-catenin nucleic acid inhibitor molecule and IDO inhibitor converts the non-T cell inflamed phenotype into a T cell-inflamed phenotype, such that the cancer becomes responsive to immunotherapy. In certain embodiments, the subject experiences tumor regression following treatment with the β-catenin nucleic acid inhibitor molecule, the IDO inhibitor, and the immunotherapy. In certain embodiments, the cancer that is resistant to immunotherapy is a Wnt activated cancer. In certain embodiments, the cancer that is resistant to immunotherapy overexpresses IDO1.

Typically, the subject begins taking the immunotherapeutic agent after the initiation of administration of the β-catenin nucleic acid inhibitor molecule and the IDO inhibitor. In other embodiments, the subject may already be taking the immunotherapeutic agent at the initiation of the administration of the β-catenin nucleic acid inhibitor molecule and/or the IDO inhibitor. In yet other embodiments, the subject may begin administration of the immunotherapeutic agent and the β-catenin nucleic acid inhibitor molecule and/or the IDO inhibitor at about the same time.

Dosing and Schedule

Typically, the β-catenin nucleic acid inhibitor molecule and IDO inhibitor are administered separately from, and on different schedules than, the immunotherapeutic agent. For example, when used as a single agent, ipilimumab (anti-CTLA-4 antibody) is administered intravenously over 90 minutes at a recommended dose of 3 mg/kg every 3 weeks for a total of 4 doses. Similarly, when used as a single agent, nivolumab (anti-PD-1 antibody), is administered intravenously at a recommended dose of 240 mg (or 3 mg/kg) over 60 minutes every 2 weeks. When nivolumab is administered in combination with ipilimumab, the recommended dose of nivolumab is 1 mg/kg administered intravenously over 60 minutes, followed by ipilimumab on the same day at a recommended dose of 3 mg/kg every 3 weeks for a total of 4 doses, and then nivolumab at a recommended dose of 240 mg every 2 weeks. When pembrolizumab is used as a single agent, it is typically administered intravenously over 30 minutes at a recommended dosage of 200 mg every 3 weeks until disease progression, unacceptable toxicity, or up to 24 months without disease progression.

Typically, the β-catenin nucleic acid inhibitor molecule is administered parenterally (such as via intravenous, intramuscular, or subcutaneous administration). In certain embodiments, the β-catenin nucleic acid inhibitor molecule is administered at a dosage of 20 micrograms to 10 milligrams per kilogram body weight of the recipient per day, 100 micrograms to 5 milligrams per kilogram, 0.25 milligrams to 5.0 milligrams per kilogram, or 0.5 to 3.0 milligrams per kilogram. Typically, the β-catenin nucleic acid inhibitor molecule is administered at a dosage of about 0.25 to 2.0 milligrams per kilogram body weight of the recipient per day.

The β-catenin nucleic acid inhibitor molecule may be administered every day or intermittently. For example, intermittent administration of the β-catenin nucleic acid inhibitor molecule may be administration one to six days per week, one to six days per month, once weekly, once every other week, once monthly, once every other month, or once or twice per year or divided into multiple yearly, monthly, weekly, or daily doses. Typically, the β-catenin nucleic acid inhibitor molecule is administered every week or every two weeks. In some embodiments, intermittent dosing may mean administration in cycles with the initial optimized β-catenin nucleic acid inhibitor molecule or immunotherapeutic agent administration followed by a rest period with no administration for up to one week, up to one month, up to two months, up to three months or up to six months or more) or it may mean administration on alternate days, weeks, months, or years.

The IDO inhibitor may be administered according to its recommended dosage schedule and route of administration. Typically, epacadostat, indoximod, and BMS-986205 are administered orally. Epacadostat is typically administered twice daily at a dose of about 50-300 mg, and more typically at a dose of about 100 mg. Indoximod is typically administered twice daily at a dose of about 600-1500 mg, and more typically at a dose of about 1000-1200 mg. BMS-986205 is typically administered once daily at a dose of about 50-100 mg, and more typically at a dose of about 100 mg.

The β-catenin nucleic acid inhibitor molecule is typically administered separately from, and on a different schedule than, the immunotherapeutic agent and/or the IDO inhibitor.

The therapeutically effective amount of the β-catenin nucleic acid inhibitor molecule, IDO inhibitor, or immunotherapeutic agent may depend on the route of administration and the physical characteristics of the patient, such as the size and weight of the subject, the extent of the disease progression or penetration, the age, health, and sex of the subject and can be adjusted as necessary depending on these and other factors.

EXAMPLES

Example 1: BCAT1 Construct

Figure 12:
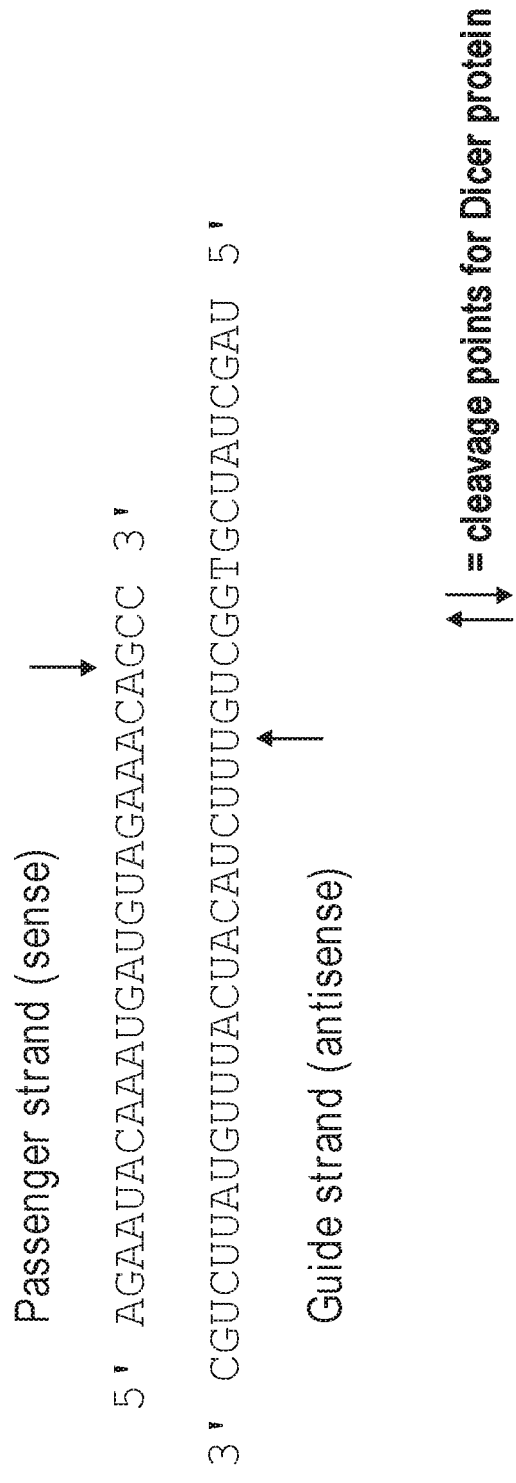
FIG. 12 shows one non-limiting embodiment of a double-stranded β-catenin nucleic acid inhibitor molecule, having of a sense (or passenger) strand (SEQ ID NO: 1) and an antisense (guide) strand (SEQ ID NO: 2). This β-catenin nucleic acid inhibitor molecule is referred to herein as BCAT1.

A nucleic acid inhibitor molecule that targets the β-catenin gene was constructed ("BCAT1"). BCAT1 has a 26 base pair passenger strand and a 38 base pair guide strand that form a duplex region consisting of 26 base pairs. FIG. 12. The 5'-end of the guide strand consists of a 10-base pair, single stranded overhang, and the 3'-end of the guide strand consists of a two-base pair single-stranded, overhang. FIG. 12.

The BCAT1 construct was formulated in EnCore lipid nanoparticles (LNP). The LNP formulated BCAT1 has been shown to effectively deliver the nucleic acid payload to multiple tumor types (see Table I below), including subcutaneous, orthotopic, disseminated and metastatic xenograft tumors, patient-derived xenografts (PDX), and genetically engineered models (GEM).

TABLE I

Delivery of BCAT1 to Various Tumor Types

| Tumor type | Description | Tumor location in model |
| --- | --- | --- |
| Acute lymphoblastic leukemia | ALL697 | disseminated/spleen |
| Acute lymphoblastic leukemia | NALM-6 | disseminated/spleen |
| Acute myelogenous leukemia | KG1 | disseminated/spleen, liver |
| Breast | MMTV-Wnt1 | Spontaneous/mammary |
| Breast | 4T1 | Subcutaneous/flank |
| Colorectal | LS411N CLDX | metastases/liver, primary/spleen |
| Colorectal | SW403 CLDX | metastases/liver |
| Colorectal | LS174T CLDX | metastases/liver, primary/spleen |
| Colorectal | SW1116 CLDX | primary/spleen |
| Colorectal | LS411N CLDX | subcutaneous/flank |
| Colorectal | SW403 CLDX | subcutaneous/flank |
| Colorectal | LS174T CLDX | subcutaneous/flank |
| Colorectal | PDX | subcutaneous/flank |
| Hepatoblastoma | liver-specific GEMM/CTNNB1-YAP | spontaneous/liver |
| Hepatoblastoma | HepG2 CLDX | subcutaneous/flank |
| Hepatoblastoma | HepG2 CLDX | orthotopic/liver |
| Hepatocellular Carcinoma | Hep3B CLDX | subcutaneous/flank |
| Hepatocellular Carcinoma | Hep3B CLDX | orthotopic/liver |
| Hepatocellular Carcinoma | PDX | orthotopic/liver |
| Hepatocellular Carcinoma | GEMM/Mst1 | spontaneous/liver |
| Hepatocellular Carcinoma | liver-specific GEMM/CTNNB1-KRAS | spontaneous/liver |
| Hepatocellular Carcinoma | liver-specific GEMM/Myc | spontaneous/liver |
| Lung | Lewis Lung Carcinoma | subcutaneous/flank |
| Melanoma | B16F10 CLDX | subcutaneous/flank |
| Melanoma | B16F10 CLDX | disseminated/lung, liver |
| Melanoma | A2058 | Subcutaneous/flank |
| Multiple Myeloma | KMS11 | subcutaneous/flank |
| Neuroblastoma | Neuro2A | Subcutaneous/flank |
| NSCLC | PDX | subcutaneous/flank |

TABLE I-continued

Delivery of BCAT1 to Various Tumor Types

| Tumor type | Description | Tumor location in model |
|---|---|---|
| Osteosarcoma | PDX | subcutaneous/flank |
| Ovarian | PDX | subcutaneous/flank |
| Pancreatic | MiaPaca2 | subcutaneous/flank |
| Pancreatic | PDX | subcutaneous/flank |
| Renal Cell Carcinoma | 786/0 | subcutaneous/flank |

Negative: HCT116, DLD1, HL60

Example 2: Tumor Studies 6-8-week-old immunocompetent mice ($C_{57}BL/6$ or Balb/C) were injected subcutaneously with $1.5 \times 10^6$ B16F10 or $1.5 \times 10^6$ 4T1 tumor cells under the right shoulder. Tumor volume was measured every 2-3 days a week to monitor tumor growth. Dosing was initiated when the tumors reached about 150-200 mm$^3$. For tumor growth inhibition studies, animals were randomized and assigned to different cohorts and subjected to dosing cycles. BCAT1 formulated LNP or Placebo (scrambled CTNNB1 dsRNAi) formulated LNP was given intravenously via lateral tail vein at a total volume of 10 ml/kg. Immunotherapy treatments (anti-PD-1 antibody) were given intraperitoneally at a volume of 10 ml/kg. Epacadostat (IDO1 inhibitor) was given orally at a total volume of 10 ml/kg.

Mouse cell lines B16F10 and 4T1 cells were obtained from ATCC (Manassas, Va.) and grown in RPMI/DMEM medium supplemented with 10% FBS. B16F10 cells is a murine melanoma cell line with no Wnt activation or IDO1 activation. 4T1 is a murine breast cell line with Wnt activation and constitutive activation of IDO1.

In the MMTV-Wnt mouse model, mammary gland specific overexpression of Wnt1 with MMTV-LTR leads to spontaneous breast tumors with activated Wnt/β-catenin signaling. MMTV-Wnt mammary tumors spontaneously grow in mice in 3-6 months from the time of birth with Wnt pathway activation.

Example 3: Inhibiting β-Catenin in Wnt Active 4T1 Tumors

Balb/C mice were implanted with 4T1 tumors. At six days post 4T1 tumor cell implantation, with the average tumor size of 150-200 mm$^3$, mice were sorted into two groups and were treated with either placebo or BCAT1 at 3 mg/kg on days 6 and 7 and days 12 and 13 post-implant, as shown in FIG. 1A. 48 hours after the last dose, tumors were collected and assayed by immunohistochemistry for β-catenin, CD8 and IDO1 protein levels. As shown in FIG. 1B, BCAT1 treatment decreased β-catenin levels and increased CD8 levels but did not reduce the IDO1 levels significantly after two rounds of treatment.

In another study, 4T1 tumor cells were implanted in Balb/C mice and 4 days post-implant, the mice were randomized into two groups and treated with placebo or BCAT1. Mice were administered two doses of placebo or BCAT1 at 3 mg/kg on days 4 and 5, as shown in FIG. 1C. This dosing cycle was then repeated on days 9 and 10. Tumor growth was monitored by measuring the tumor sizes over the course of the treatment period. Treating mice with BCAT1 alone resulted in tumor growth inhibition of about 40%. FIG. 1C.

Figure 2B:
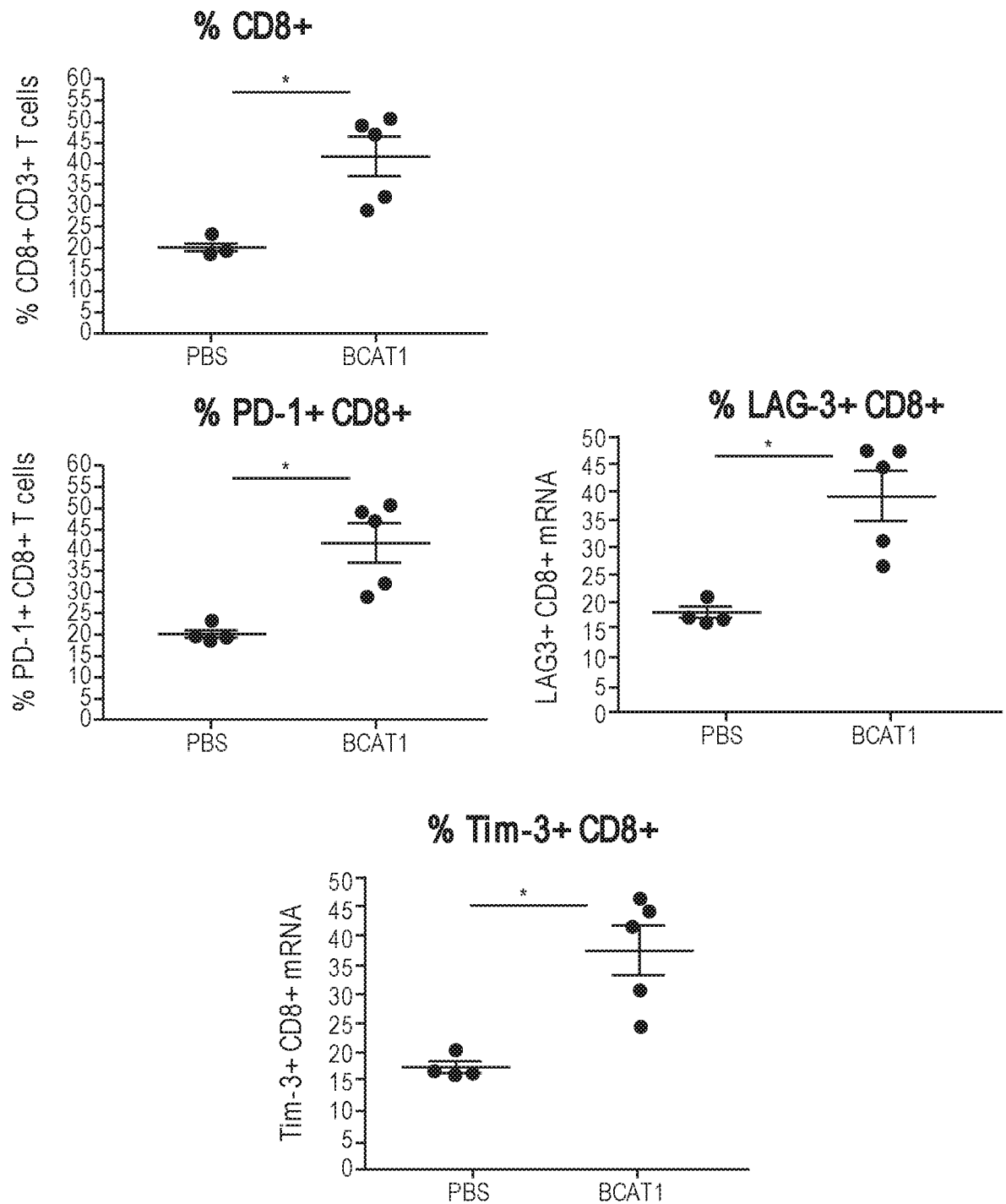
FIG. 2B shows by flow cytometry analysis that BCAT1 treatment of 4T1 tumors increases CD8+ T cells, increases multiple checkpoint molecules (PD-1, LAG-3+, and Tim-3+), and increases regulator T cells (Tregs) but does not significantly alter the number of myeloid derived suppressor cells (MDSC) in the tumor microenvironment.
Figure 2B:
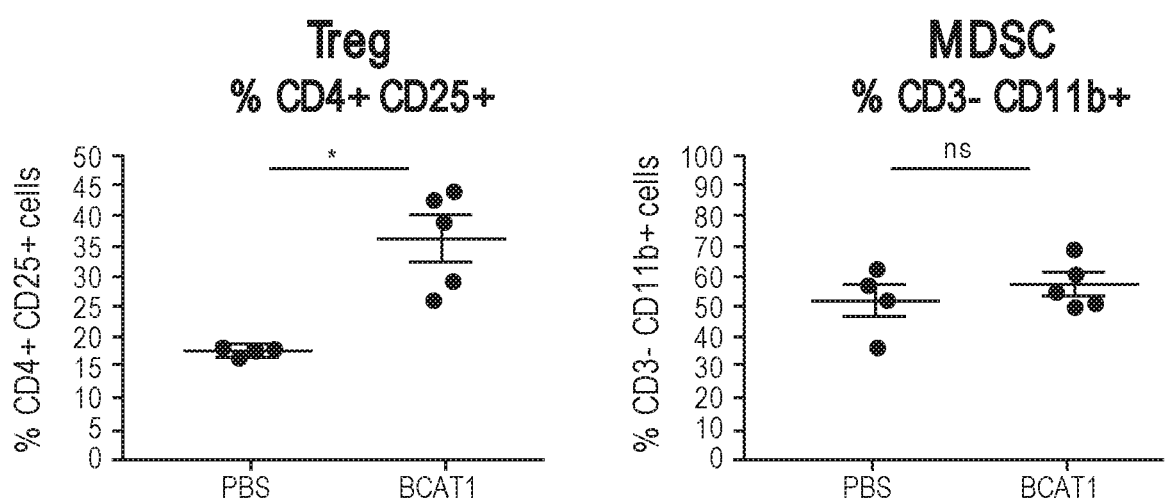

In another similar study, mice bearing 4T1 tumors were treated with PBS or BCAT1 at 3 mg/kg on days 6 and 7 and days 12 and 13 post-implant, as shown in FIG. 2A. Tumors were collected 24 hours after the last dose and subjected to flow cytometry to measure surface markers on single-cell suspensions prepared from the extracted tumors. While the PBS control had no significant effect on the tumor immune microenvironment, BCAT1 treatment resulted in significant increases in cytotoxic T-cells (CD8), and multiple checkpoints (PD-1, LAG-3 and Tim-3). FIG. 2B. BCAT1 treatment significantly increased Regulatory T cells (Tregs), which play an important role in regulating or suppressing other cells of the immune system. FIG. 2B. No effect was observed on the immunosuppressive MDSC cells. FIG. 2B.

Example 4: Inhibiting IDO1 in Wnt Active 4T1 Tumors

Another efficacy study was performed in 4T1 tumors with the IDO1 inhibitor, Epacadostat (IDOi). 4T1 tumor-bearing mice were randomized into two groups and treated orally with vehicle or IDOi twice daily at 100 mg/kg per dose on days 6 and 8 post-implant, as shown in FIG. 3A. Tumors were collected 48 hours after the last dose and were subjected to immunohistochemistry to look at β-catenin, CD8 and IDO1 levels. IDOi at 100 mg/kg reduced the IDO1 levels almost completely but β-catenin and CD8 levels were only modestly altered. FIG. 3B. FIG. 3B. In a related study, mice bearing 4T1 tumors were administered placebo or IDOi twice daily at 100 mg/kg per day on days 6 and 8 post-implant, as shown in FIG. 3C. Tumor growth was monitored by measuring the tumor sizes over the course of the treatment period. Treating mice with IDOi alone led to tumor growth inhibition, suggesting that, in addition to β-catenin, the 4T1 tumors also depend on IDO1 for tumor growth. FIG. 3C.

Figure 4A:
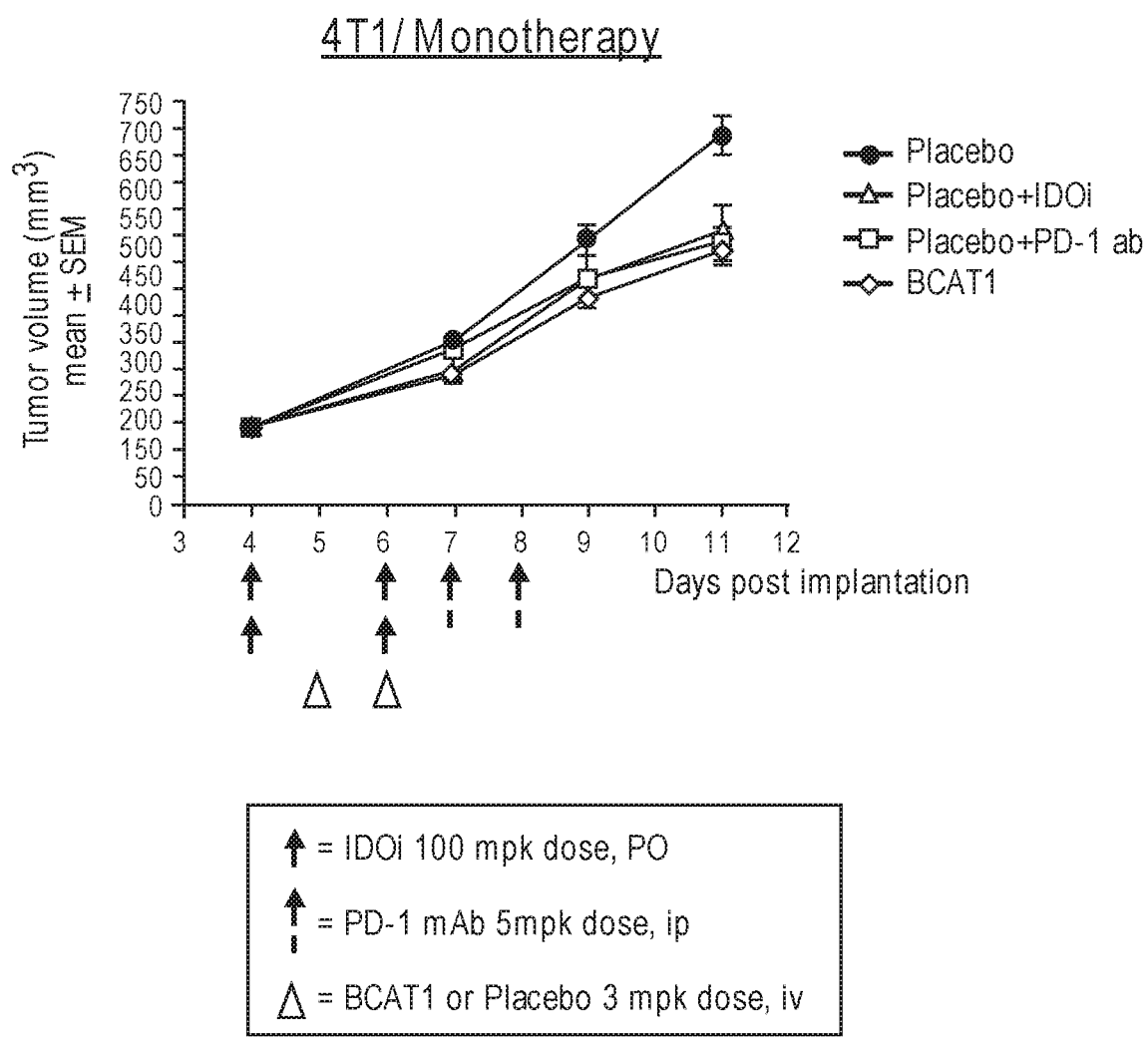
FIGS. 4A-C shows the efficacy of IDOi (epacadostat), an anti-PD-1 antibody (PD-1), and BCAT administered as single agents (FIG. 4A), combinations of two agents (FIG. 4B), or combinations of three agents (FIG. 4C) in Balb/C mice implanted with 4T1 tumors, with the combination of all three agents showing tumor regression, as described in Example 5.
Figure 4B:
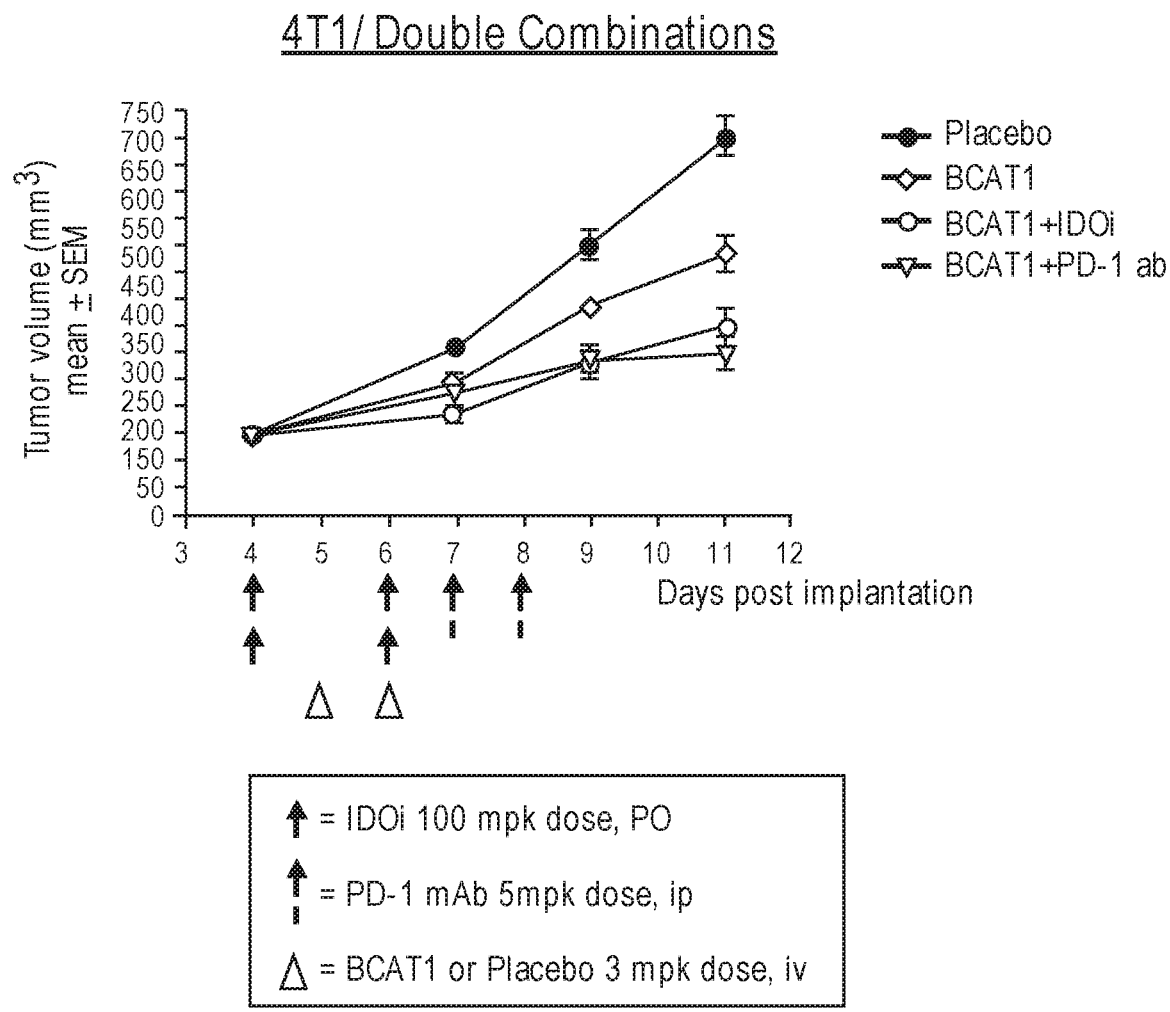
Figure 4C:
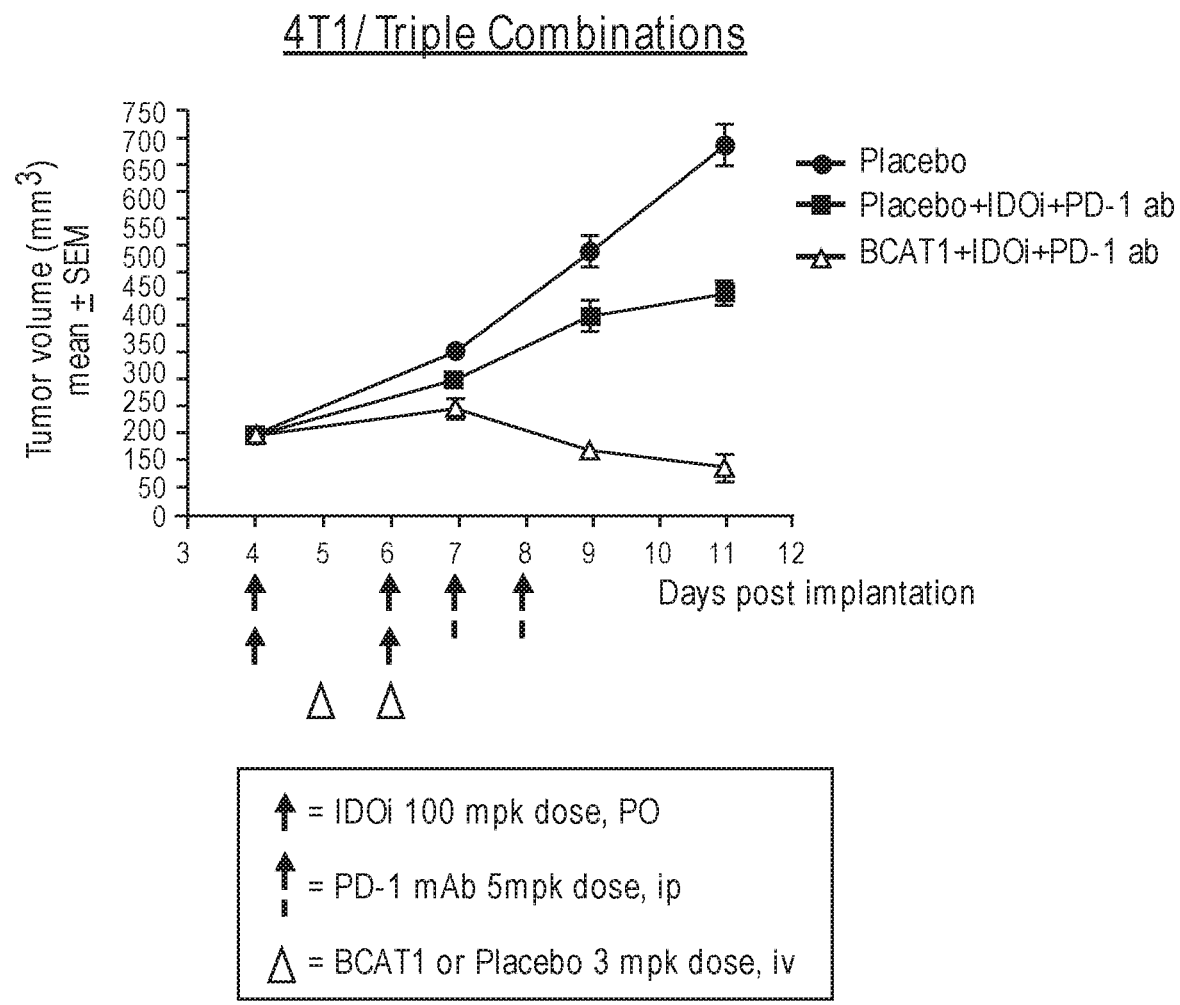

Example 5: Inhibiting IDO1 in Wnt Active 4T1 Tumors in Combination with β-Catenin Inhibition and/or a Checkpoint Inhibitor Next, combination therapy in 4T1 tumors with BCAT1 and IDOi or BCAT and a checkpoint inhibitor (anti PD-1 antibody) or triple combination therapy with BCAT1, IDO1, and an anti-PD-1 antibody was assessed. 4T1 tumor-bearing mice were sorted into 8 groups (n=5) and pre-treated twice daily with IDOi (orally at 100 mg/kg per dose) on days 4 and 6 post-implant and BCAT1 or placebo (iv at 3 mg/kg per dose) on days 5 and 6 post-implant, followed by anti-PD-1 antibody (ip at 5 mg/kg per dose) on days 7 and 8 post-implant, as shown in FIG. 4C. Mice also received BCAT1, IDOi and PD-1 antibody as single agents (FIG. 4A) and combinations of two agents (FIG. 4B). Mice receiving BCAT1, IDOi, or anti-PD1 antibody as monotherapy showed modest anti-tumor efficacy. FIG. 4A. The mice that received combination therapy with BCAT1 and anti-PD-1 antibody or BCAT1 and IDOi demonstrated tumor stasis, reducing the rate of tumor growth. FIG. 4B. Remarkably, mice that were treated with all three agents (BCAT1, IDOi and anti-PD-1 antibody) demonstrated tumor regression, as shown in FIG. 4C, with pronounced reduction of the tumor volume starting after administration of all three agents. Notably, as shown in FIG. 4C, the anti-tumor effect of the triple combination of BCAT1, epacadostat (IDOi), and the anti-PD-1 antibody was markedly superior to the effect observed with the double combination of epacadostat (IDOi) and the anti-PD-1, which is currently being evaluated in Phase I/II studies.

Figure 5A:
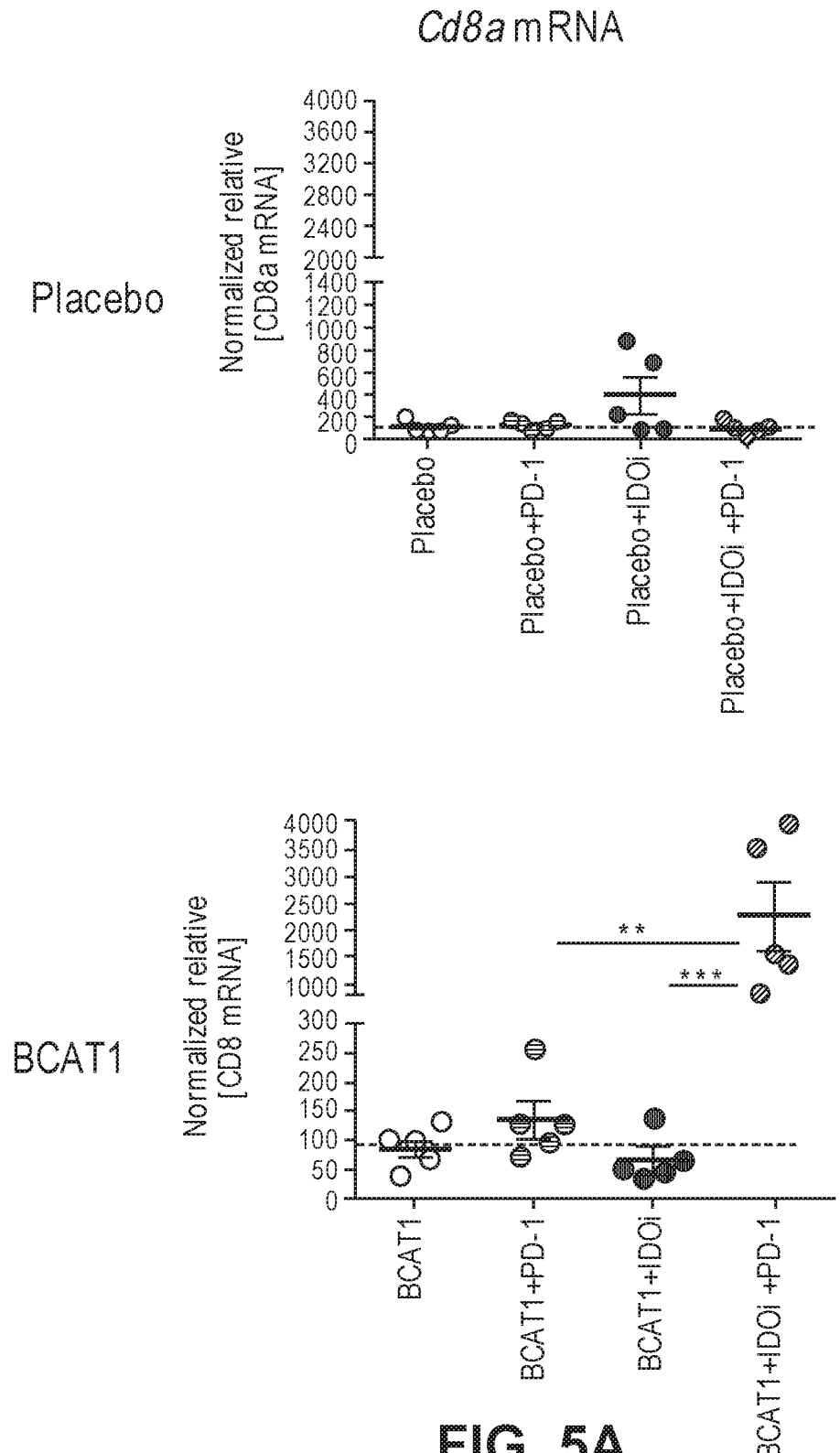
FIGS. 5A-B shows the mRNA levels of CD8 (FIG. 5A) and Foxp3 (FIG. 5B) in 4T1 tumors treated with IDOi, anti-PD-1 antibody and/or BCAT1 and demonstrates that only the combination of all three agents significantly increased CD8 mRNA levels and significantly decreased Foxp3 mRNA levels.
Figure 5B:
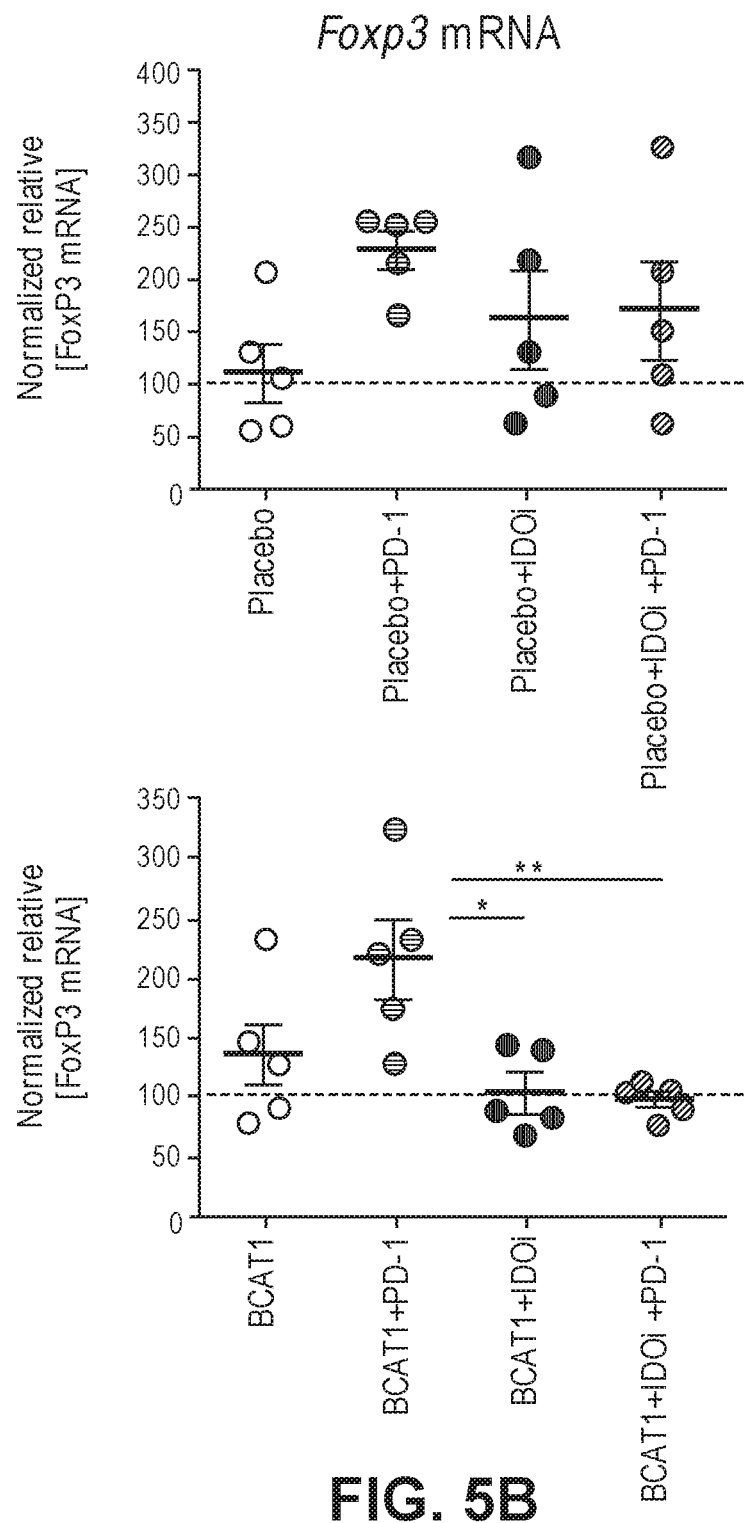

At the end of the study (72 hours after the last anti-PD-1 antibody treatment), tumors were collected and subjected to qPCR to analyze certain T cell markers. There was a substantial increase in CD8 mRNA observed in the mice that received the triple combination treatment as compared to the other groups. FIG. 5A. FoxP3 is a marker for immunosuppressive T cells called Tregs. Foxp3 mRNA levels were increased when the anti-PD-1 antibody was added to either placebo or BCAT1 treatment. FIG. 5B. These levels were returned to background levels with the addition of IDOi. FIG. 5B. Without intending to be bound by any theory, these mRNA data suggest that the triple combination of BCAT1, IDOi, and anti-PD-1 antibody resulted in both a substantial increase in CD8 T cells and reduced levels of the immunosuppressive Tregs, and that these changes in the T cell populations within the 4T1 tumor microenvironment likely contributed to the observed tumor regression.

Example 6: Inhibiting β-Catenin in Non-Wnt Active B16F10 Tumors

C57BL/6 mice were implanted with B16F10 tumors. At six days post B16F10 tumor cell implantation, with the average tumor size of 200 mm$^3$, mice were sorted into two groups and were treated with either placebo or BCAT1 at 3 mg/kg on days 6 and 7 post-implant and again on days 12 and 13 post-implant, as shown in FIG. 6A. 48 hours after the last dose, tumors were collected and assayed by immunohistochemistry for β-catenin, CD8 and IDO1 protein levels. BCAT1 treatment decreased the levels of β-catenin and increased the levels of CD8 levels (FIG. 6B), as observed with the 4T1 tumors. However, unlike the 4T1 tumors, BCAT1 treatment decreased the levels of IDO1 in B16F10 tumors. FIG. 6B.

In a similar study, B16F10 tumor cells were implanted in C57BL/6 mice and at day 5 post-implant, the mice were randomized into two groups and treated with placebo or BCAT1. Mice were administered placebo or BCAT1 at 3 mg/kg on days 5 and 6, as shown in FIG. 6C. This dosing cycle was then repeated on days 11 and 12. Tumor growth was monitored by measuring the tumor sizes over the course of the treatment period. BCAT1, administered as a single agent, did not significantly inhibit tumor growth in these B16F10 tumors. FIG. 6C.

Figure 7A:
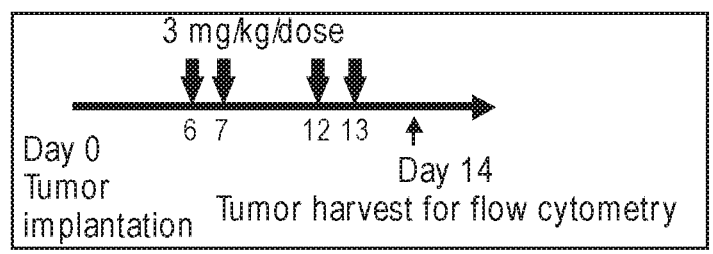
FIG. 7A shows the treatment schedule for C57BL/6 mice that were implanted with B16F10 tumors and treated with placebo or BCAT1, as described in Example 6.
Figure 7B:
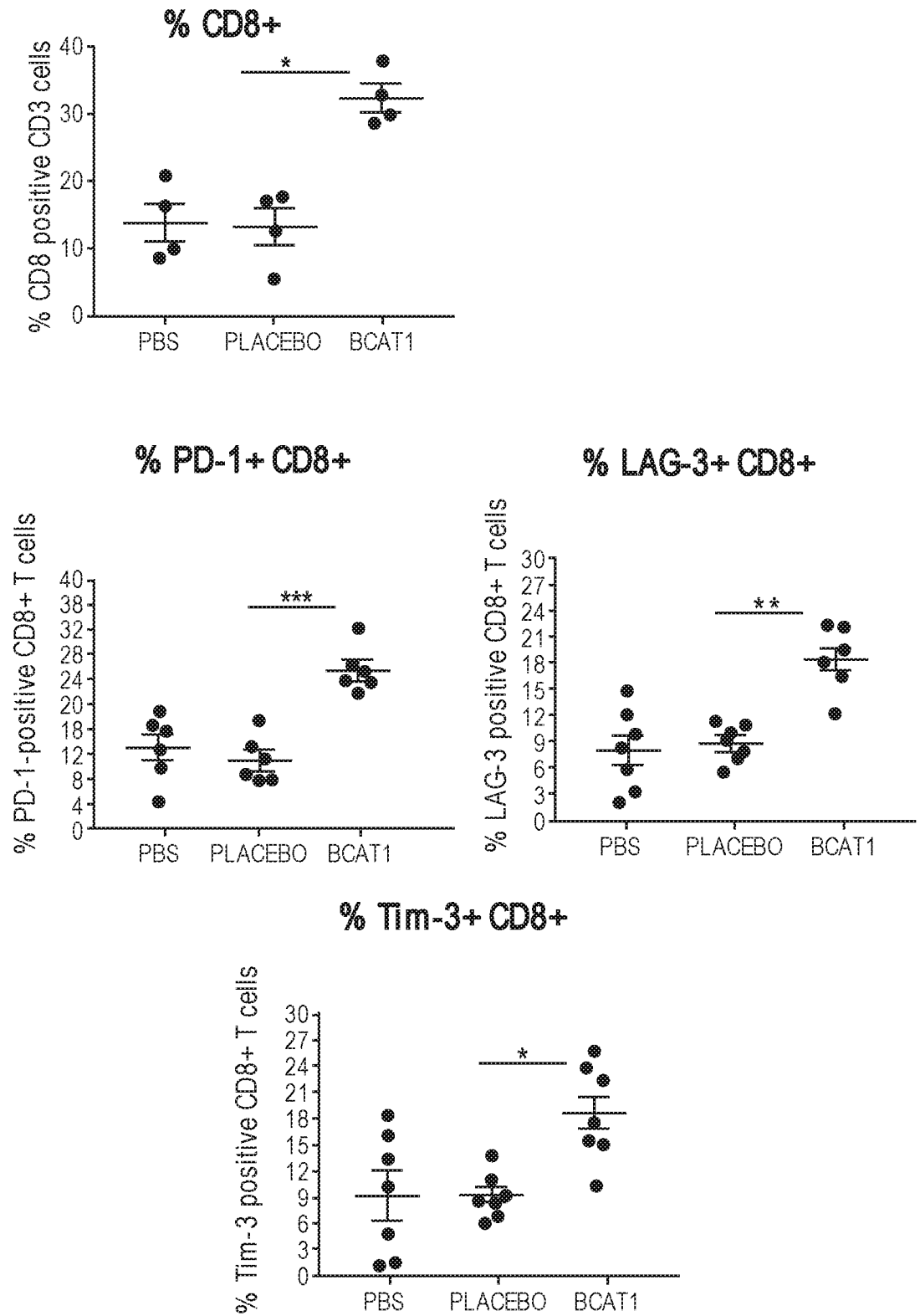
FIG. 7B shows by flow cytometry analysis that BCAT1 treatment of B16F10 tumors increases CD8+ T cells, increases multiple checkpoint molecules (PD-1, LAG-3+, and Tim-3+), but does not significantly alter the number of regulator T cells (Tregs) or myeloid derived suppressor cells (MDSC) in the tumor microenvironment.
Figure 7B:
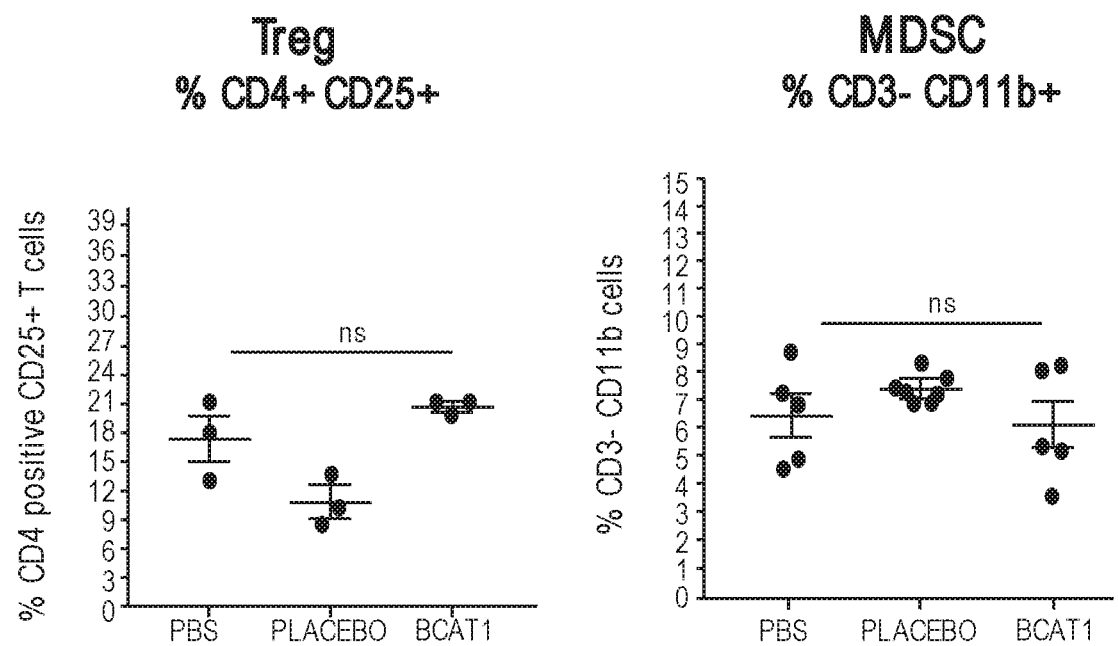

A similar study was run to monitor the levels of immune cell infiltrate after two rounds of BCAT1 treatment. B16F10 tumors were treated with PBS, placebo, or BCAT1 at 3 mg/kg on days 6 and 7 post-implant and again on days 12 and 13 post-implant, as shown in FIG. 7A. Tumors were collected 24 hours after the last dose and were subjected to flow cytometry. As shown in FIG. 7B, CD8 T cells and multiple checkpoints (PD-1, LAG-3, and Tim-3) were elevated following treatment with BCAT1. The MDSC cell population was not altered. FIG. 7B. Placebo treatment reduced the level of Tregs slightly, while BCAT1 treatment did not significantly change the level of Tregs as compared to PBS (FIG. 7B), suggesting that treatment of B16F10 tumors with BCAT1 did not significantly alter the immunosuppressive MDSC and Tregs cell populations.

Example 7: Inhibiting IDO1 in Non-Wnt Active B16F10 Tumors

Another efficacy study was performed in B16F10 tumors with the IDO inhibitor, Epacadostat (IDOi). B16F10 tumor-bearing mice were randomized into two groups and treated orally with vehicle or IDOi twice daily at 100 mg/kg per dose on days 7 and 9 post-implant as shown in FIG. 8A. Tumors were collected 48 hours after the last dose and were subjected to immunohistochemistry to analyze β-catenin, CD8 and IDO1 levels. IDOi at 100 mg/kg reduced the IDO1 levels almost completely. IDOi also decreased β-catenin levels and increased CD8 levels. FIG. 8B.

In a similar study, B16F10 tumor cells were implanted in C57BL/6 mice and at day 7 post-implant, the mice were randomized into two groups and treated with vehicle or IDOi twice daily at 100 mg/kg per dose on days 7 and 9, as shown in FIG. 8C. Tumor growth was monitored by measuring the tumor sizes over the course of the treatment period. Depletion of IDO1 did not result in any significant tumor growth inhibition. FIG. 8C.

Figure 9A:
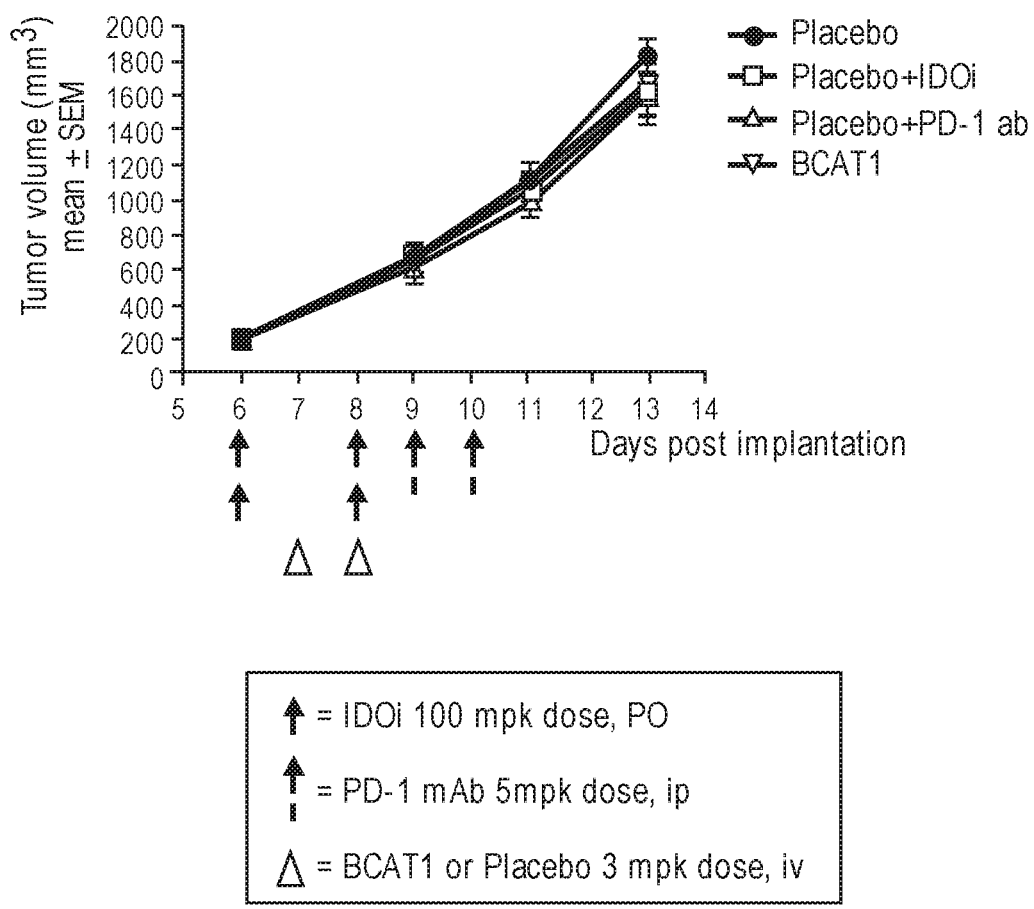
FIGS. 9A-C shows the efficacy of IDOi (epacadostat), an anti-PD-1 antibody (PD-1), and BCAT1 administered as single agents (FIG. 9A) or combinations of two or three agents (FIGS. 9B and 9C) in C57BL/6 mice implanted with B16F10 tumors, as described in Example 8.
Figure 9B:
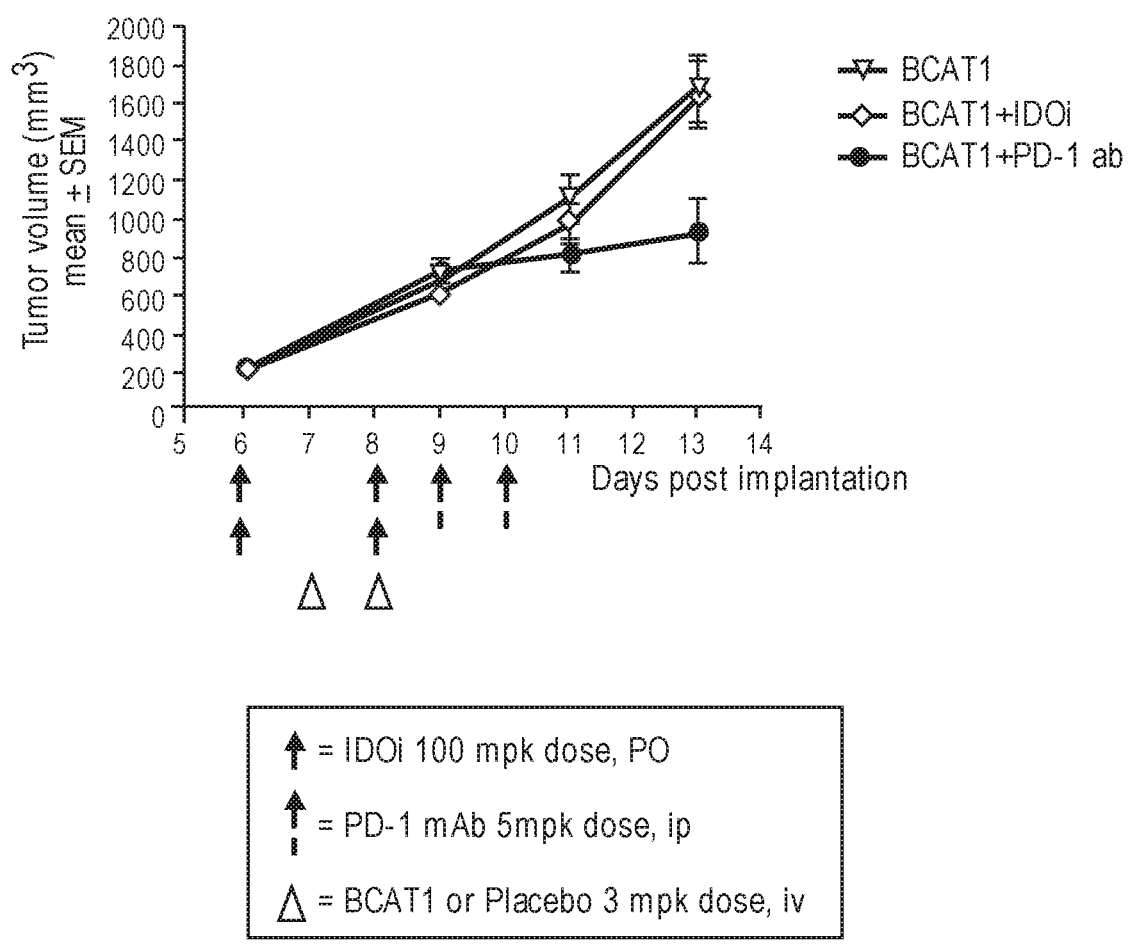
Figure 9C:
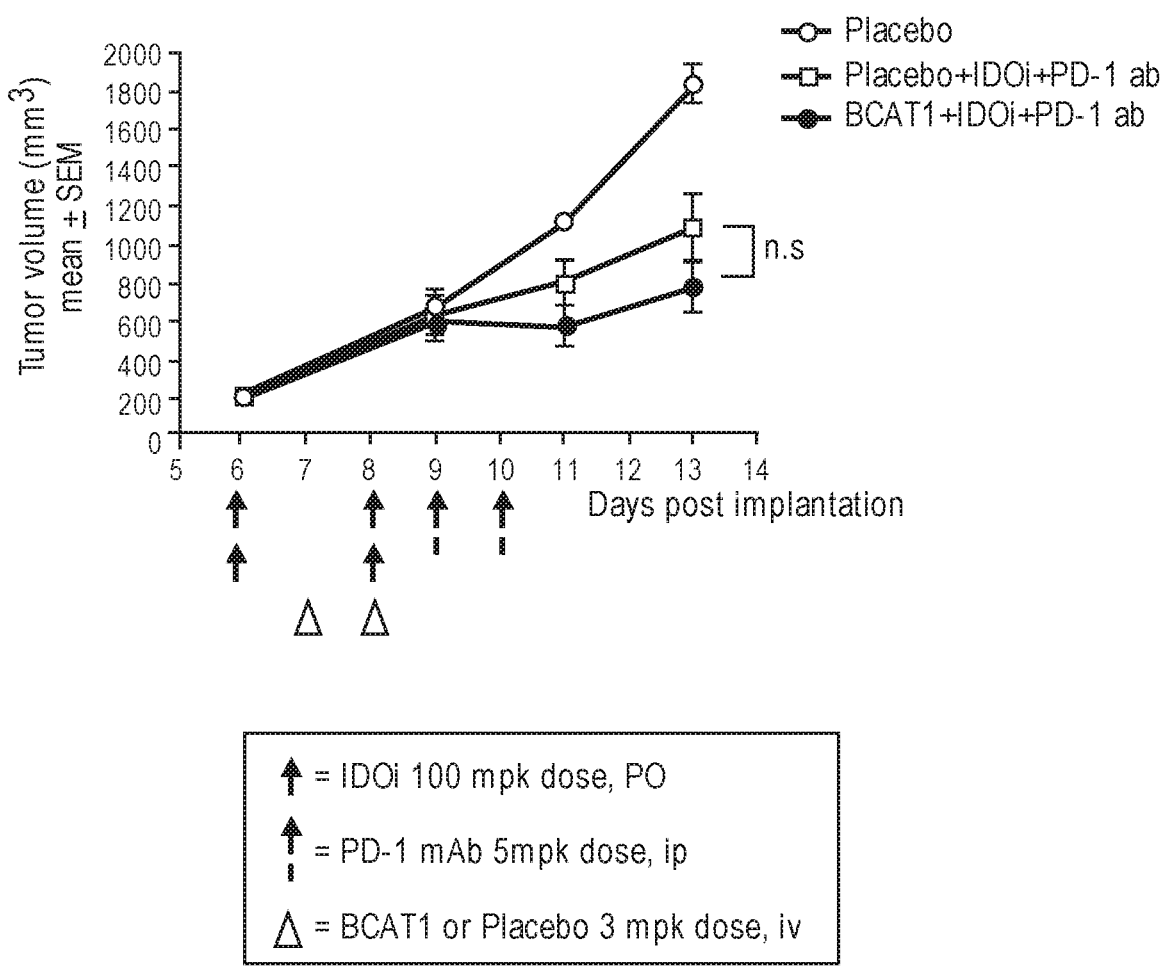

Example 8: Inhibiting IDO1 in B16F10 Tumors, in Combination with β-Catenin Inhibition and/or a Checkpoint Inhibitor Next, combination therapy in B16F10 tumors with BCAT1 and IDOi or BCAT and a checkpoint inhibitor (anti PD-1 antibody) or triple combination therapy with BCAT1, IDOi, and an anti-PD-1 antibody was assessed. B16F10 tumor-bearing mice at 200 mm$^3$ were grouped and treated with either single agents or double agents or triple agents as shown in FIGS. 9A-C. In these studies, mice were treated twice daily with IDOi (orally at 100 mg/kg per dose) on days 6 and 8 post-implant, BCAT1 or placebo (iv at 3 mg/kg per dose) on days 7 and 8 post-implant, followed by anti-PD-1 antibody (ip at 5 mg/kg per dose) on days 9 and 10 post-implant, as shown in FIGS. 9A-C.

Single agents were ineffective in these B16F10 tumors, as was the combination of BCAT1 and IDO1 (FIGS. 9A-B). Tumors treated with a combination of BCAT1 and anti-PD-1 antibody or IDOi and anti-PD-1 antibody showed synergistic tumor growth inhibition, as compared to treatment with the single agents. FIGS. 9B-C. However, adding a third agent to the combination (i.e., BCAT, IDOi and anti-PD-1 antibody) did not appear to significantly improve B16F10 tumor growth inhibition as compared to BCAT1+anti-PD-1 antibody or IDOi+anti-PD1 antibody. FIGS. 9B-C. Since BCAT1 treatment of B16F10 tumors depleted IDO1 levels and did not alter the immune suppressive MDSC and Tregs, the inclusion of IDOi did not seem to contribute any additional benefit. Likewise, IDOi decreased IDO1 and β-catenin levels as a single agent. Consistent with this finding, IDOi in combination with anti-PD-1 antibody resulted in a similar efficacy as the BCAT1 and anti-PD-1 antibody combination.

Example 9: Inhibiting β-Catenin in Wnt Active MMTV Tumor Model

To see the effect of β-catenin inhibition on T cell infiltration and IDO1 levels in spontaneous tumors, the MMTV-Wnt1 model was used. MMTV-Wnt tumor-bearing mice were treated with BCAT1 at 5 mg/kg per dose on study days 1, 2, and 3 as shown in FIG. 10A. The tumors were collected 24 hours after the last dose and subjected to immunohistochemistry to determine β-catenin, CD8, and IDO1 levels. The results were very similar to what was observed in 4T1 tumors. β-catenin levels were decreased, CD8 levels were increased and the IDO1 levels were unchanged (FIG. 10B).

In another study, MMTV-Wnt tumor-bearing mice were treated with BCAT1 at 3 mg/kg on study days 1, 2, 6, and 7 and tumor growth was monitored. Treating mice with BCAT1 alone resulted in tumor growth inhibition of about 50% (FIG. 10C), similar to the tumor reduction observed in 4T1 tumors.

Example 10: Inhibiting IDO1 in Wnt Active MMTV Tumor Model

Figure 11B:
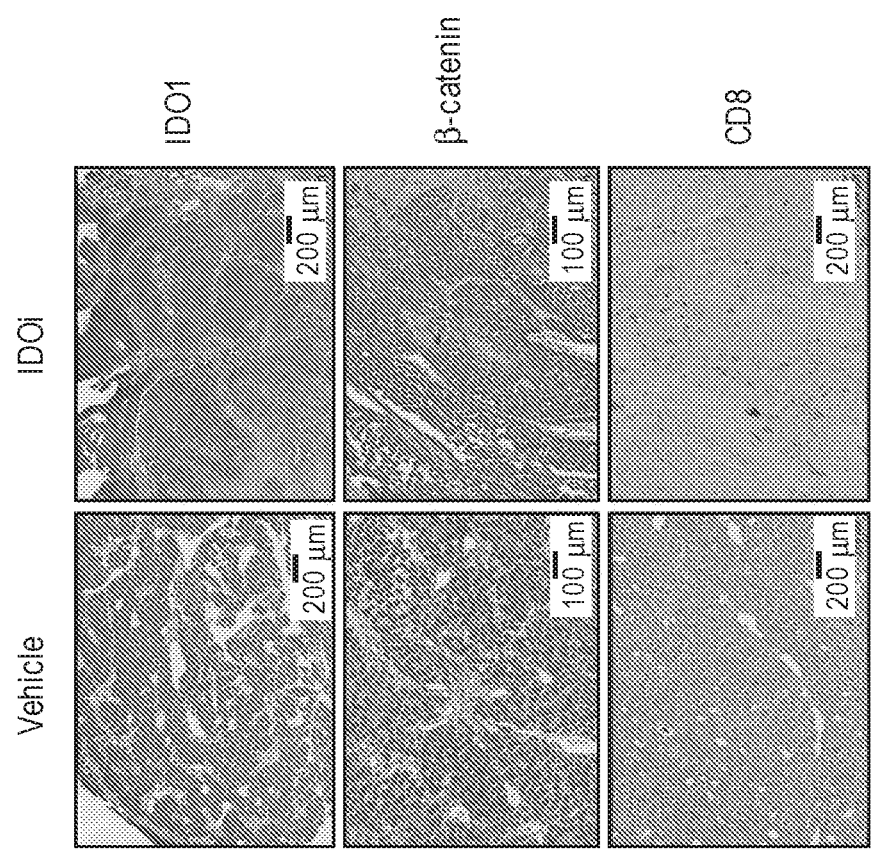
FIG. 11B shows by immunohistochemistry that IDOi treatment reduces IDO1 levels and increases β-catenin and CD8 levels.
Figure 11A:
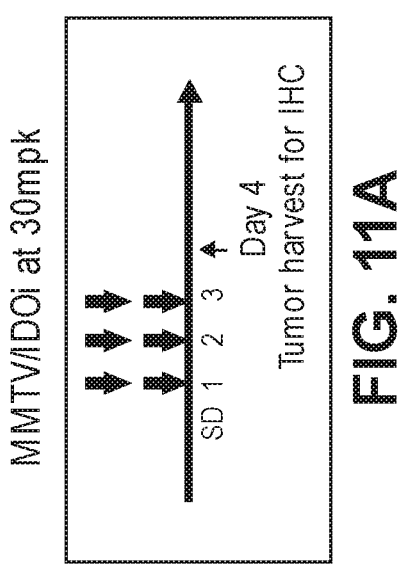
FIG. 11A shows the treatment schedule for MMTV-Wnt tumor-bearing mice that were treated with vehicle or an IDO inhibitor (IDOi) called epacadostat, as described in Example 10.

In a separate study, the MMTV tumor-bearing mice were treated with an IDO1 inhibitor (IDOi) at 30 mg/kg per dose twice a day for 3 consecutive days as shown in FIG. 11A. Tumors were collected 24 hours after the last dose and subjected to immunohistochemistry to determine β-catenin, CD8 and IDO1 levels. IDOi at 30 mg/kg reduced the IDO1 levels almost completely, however, the β-catenin and CD8 levels were increased upon IDOi treatment (FIG. 11B).

What is claimed is:

1. A method of treating cancer in a subject, comprising administering to the subject:
   a therapeutically effective amount of a β-catenin nucleic acid inhibitor molecule;
   a therapeutically effective amount of an indoleamine 2,3-dioxygenase ("IDO") inhibitor; and
   a therapeutically effective amount of an immunotherapeutic agent, wherein the subject experiences tumor regression following treatment.

2. The method of claim 1, wherein the subject is a human.

3. The method of claim 1, wherein the cancer is a Wnt-activated cancer.

4. The method of claim 1, wherein the IDO inhibitor comprises epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan.

5. The method of claim 1, wherein the IDO inhibitor is epacadostat.

6. The method claim 1, wherein the β-catenin nucleic acid inhibitor molecule is a double stranded RNAi inhibitor molecule.

7. The method of claim 1, wherein the β-catenin nucleic acid inhibitor molecule is a double stranded RNAi inhibitor molecule comprising a sense stand and an antisense strand and a region of complementarity between the sense strand and the antisense strand of about 15-45 nucleotides.

8. The method of claim 7, wherein
   a) the sense strand is 15-45, 18-26, or 19-21 nucleotides and the antisense strand is 15-45, 18-26, or 19-21 nucleotides;
   b) the sense strand is 15-66 nucleotides and the antisense strand is 15-66 nucleotides;

c) the sense strand is 25-40 nucleotides or 19-25 nucleotides;
d) the antisense strand is 25-40 nucleotides or 19-25 nucleotides;
e) the sense strand is 19-25 nucleotides and the antisense strand is 19-25 nucleotides;
f) the sense strand is 26-30 or 34-40 nucleotides and contains a stem and a tetraloop, the antisense strand is 18-24 nucleotides, wherein the sense strand and antisense strand form a duplex region of 18-24 nucleotides; or
g) the sense strand is 27-29 or 33-39 nucleotides and contains a stem and a triloop and the antisense strand is 18-24 nucleotides, wherein the sense strand and antisense strand form a duplex region of 18-24 nucleotides.

9. The method of claim 1, wherein the β-catenin nucleic acid inhibitor molecule is a double stranded RNAi inhibitor molecule comprising a sense and an antisense strand and a region of complementarity between the sense strand and the antisense strand of 18-34 nucleotides, wherein the sense strand is 25-36 nucleotides in length and the antisense strand is 26-38 nucleotides in length and includes a single-stranded overhang of 1-5 nucleotides at its 3'-terminus.

10. The method of claim 9, wherein the antisense strand of the double stranded RNAi inhibitor molecule further comprises a single-stranded overhang of 1-10 nucleotides at its 5'-terminus.

11. The method of claim 1, wherein the β-catenin nucleic acid inhibitor molecule is a double stranded RNAi inhibitor molecule comprising a sense and an antisense strand and a region of complementarity between the sense strand and the antisense strand of 20-30, 21-26, 19-24, or 19-21 nucleotides.

12. The method of claim 1, wherein the β-catenin nucleic acid inhibitor molecule is a double stranded RNAi inhibitor molecule comprising a sense and an antisense strand and a region of complementarity between the sense strand and the antisense strand of 19 nucleotides, wherein the sense strand is 21 nucleotides in length and includes a single-stranded overhang of 2 nucleotides at its 3'-terminus and wherein the antisense strand is 21 nucleotides in length and includes a single-stranded overhang of 2 nucleotides at its 3'-terminus.

13. The method of claim 1, wherein the β-catenin nucleic acid inhibitor molecule is a double stranded RNAi inhibitor molecule comprising a sense and an antisense strand and a region of complementarity between the sense strand and the antisense strand of 21 nucleotides, wherein the sense strand is 21 nucleotides in length and wherein the antisense strand is 23 nucleotides in length and includes a single-stranded overhang of 2 nucleotides at its 3'-terminus.

14. The method of claim 1, wherein the β-catenin nucleic acid inhibitor molecule is a double stranded RNAi inhibitor molecule comprising a sense and an antisense strand and a region of complementarity between the sense strand and the antisense strand of 26 nucleotides, wherein the sense strand is 26 nucleotides in length and wherein the antisense strand is 38 nucleotides in length and includes a single-stranded overhang of 2 nucleotides at its 3'-terminus and a single-stranded overhang of 10 nucleotides at its 5'-terminus.

15. The method of claim 14, wherein the sense strand comprises or consists of the sequence of SEQ ID NO: 1.

16. The method of claim 15, wherein the antisense strand comprises or consists of the sequence of SEQ ID NO: 2.

17. The method of claim 7, wherein the β-catenin nucleic acid inhibitor molecule contains a tetraloop or a triloop.

18. The method of claim 1, wherein the β-catenin nucleic acid inhibitor molecule is a conventional antisense oligonucleotide that has a nucleotide sequence in the 5' to 3' direction that comprises the reverse complement of a segment of a human β-catenin gene and is 12-30, 12-25, 12-22, 14-20, or 18-22 nucleotides in length.

19. The method of claim 18, wherein the conventional antisense oligonucleotide is 16-18 or 18-20 nucleotides in length.

20. The method of claim 1, wherein the immunotherapeutic agent is an antagonist of an inhibitory immune checkpoint molecule or an agonist of a co-stimulatory checkpoint molecule.

21. The method of claim 20, wherein the immunotherapeutic agent is an antagonist of an inhibitory check point, and the inhibitory check point is PD-1 or PD-L1.

22. The method of claim 21, wherein the antagonist of the inhibitory immune checkpoint molecule or the agonist of the co-stimulatory checkpoint molecule is a monoclonal antibody.

23. The method of claim 22, wherein the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

24. A method of treating cancer in a human subject, comprising administering to the human subject:
   a therapeutically effective amount of a β-catenin nucleic acid inhibitor molecule, wherein the β-catenin nucleic acid inhibitor molecule is a double stranded RNAi inhibitor molecule comprising a sense and an antisense strand and a region of complementarity between the sense strand and the antisense strand of 18-34 nucleotides, wherein the sense strand is 19-36 nucleotides in length and the antisense strand is 18-38 nucleotides in length and includes 1-5 single-stranded nucleotides at its 3'-terminus;
   a therapeutically effective amount of an IDO inhibitor, wherein the IDO inhibitor comprises epacadostat, indoximod, BMS-986205, NLG802, HTI-1090, navoximod, PF-06840003, IOM2983, RG-70099, a phenyl benzenesulfonylhydrazide, β-(3-benzofuranyl)-alanine, β-[3-benzo(b)thienyl]-alanine, or 6-nitro-D-tryptophan; and
   a therapeutically effective amount of an immunotherapeutic agent, wherein the immunotherapeutic agent comprises an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody, wherein the human subject experiences tumor regression following treatment.

25. The method of claim 24, wherein the IDO inhibitor is epacadostat.

26. The method of claim 24, wherein the cancer is a Wnt activated cancer.

27. The method of claim 26, wherein the cancer overexpresses IDO1.

28. The method of claim 24, wherein the region of complementarity between the sense strand and the antisense strand is 21-26 nucleotides, wherein the sense strand is 21-26 nucleotides in length and wherein the antisense strand is 23-38 nucleotides in length and includes a single-stranded overhang of 1-2 nucleotides at its 3'-terminus.

29. The method of claim 28, wherein the antisense strand further comprises a single-stranded overhang of 1-10 nucleotides at its 5'-terminus.

30. The method of claim 26, wherein the β-catenin nucleic acid inhibitor molecule is a double stranded RNAi inhibitor molecule comprising a sense and an antisense strand and a region of complementarity between the sense strand and the antisense strand of 26 nucleotides, wherein the sense strand is 26 nucleotides in length and wherein the antisense strand is 38 nucleotides in length and includes a single-stranded overhang of 2 nucleotides at its 3'-terminus and a single-stranded overhang of 10 nucleotides at its 5'-terminus.

31. The method of claim 24, wherein the sense strand comprises or consists of the sequence of SEQ ID NO: 1 and the antisense strand comprises of consists of the sequence of SEQ ID NO: 2.

32. The method of claim 24, wherein:
a) the sense strand is 34-36 nucleotides and contains a stem and a tetraloop, and the antisense strand is 18-24 nucleotides, wherein the sense strand and antisense strand form a duplex region of 18-24 nucleotides; or
b) the sense strand is 33-35 nucleotides and contains a stem and a triloop, and the antisense strand is 18-24 nucleotides, wherein the sense strand and antisense strand form a duplex region of 18-24 nucleotides.

33. The method of claim 24, wherein the region of complementarity between the sense strand and the antisense strand is 19 nucleotides, wherein the sense strand is 21 nucleotides in length and includes a single-stranded overhang of 2 nucleotides at its 3'-terminus and wherein the antisense strand is 21 nucleotides in length and includes a single-stranded overhang of 2 nucleotides at its 3'-terminus.

34. The method of claim 24, wherein the region of complementarity between the sense strand and the antisense strand is 21 nucleotides, wherein the sense strand is 21 nucleotides in length and wherein the antisense strand is 23 nucleotides in length and includes a single-stranded overhang of 2 nucleotides at its 3'-terminus.

35. The method of claim 1, wherein the β-catenin nucleic acid inhibitor molecule is formulated with a lipid nanoparticle.

36. The method of claim 35, wherein the lipid nanoparticle comprises a cationic lipid and a pegylated lipid.

37. The method of claim 1, wherein administering the β-catenin nucleic acid inhibitor molecule, the IDO inhibitor, and the immunotherapeutic agent reduces the amount of cancer in the subject.

38. The method of claim 1, wherein the subject has been identified as having a Wnt activated cancer and/or a cancer that overexpresses IDO1 before the administering step.

39. The method of claim 1, further comprising before the administering step, a step of analyzing a tumor sample from the subject to determine if the subject has a Wnt activated cancer or a cancer that overexpresses IDO1.

40. The method of claim 1, wherein the Wnt activated cancer is resistant to treatment with the immunotherapeutic agent when the immunotherapeutic agent is not administered in combination with the β-catenin nucleic acid inhibitor molecule and the IDO inhibitor.

\* \* \* \* \*

SEQUENCE LISTING

```
<160> NUMBER OF SEQ ID NOS: 3

<210> SEQ ID NO 1
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
agaauacaaa ugauguagaa acagcc                                          26

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uagcuaucgt ggcuguuucu acaucauuug uauucugc                             38

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15
```